United States Patent [19]

Schultz

[11] Patent Number: 5,302,516
[45] Date of Patent: *Apr. 12, 1994

[54] CATALYTIC AND REACTIVE POLYPEPTIDES AND METHODS FOR THEIR PREPARATION AND USE

[75] Inventor: Peter Schultz, Oakland, Calif.

[73] Assignee: Regents of the University of California, Berkeley, Calif.

[*] Notice: The portion of the term of this patent subsequent to Jun. 1, 2010 has been disclaimed.

[21] Appl. No.: 988,643

[22] Filed: Dec. 10, 1992

Related U.S. Application Data

[63] Continuation of Ser. No. 404,920, Sep. 8, 1989, which is a continuation-in-part of Ser. No. 273,455, Nov. 18, 1988, abandoned.

[51] Int. Cl.$^5$ .......................... C12N 9/00; C12P 1/00
[52] U.S. Cl. .................................. 435/41; 435/188.5
[58] Field of Search ............................ 435/188.5, 41

[56] References Cited

U.S. PATENT DOCUMENTS 4,764,464  8/1988  Zemel .
4,888,281  12/1989  Schochetman et al. .
4,900,674  2/1990  Benkovic et al. .
4,963,355  10/1990  Kim et al. .

FOREIGN PATENT DOCUMENTS 0305870  8/1989  European Pat. Off. .
85/02414  6/1985  PCT Int'l Appl. .

OTHER PUBLICATIONS

Paul, S., et al, (1991) J. Biol. Chem. 266(24), 16128-16134.
Van Brunt, J. (1986) Bio/technology 4, 928-930.
Pollack, et al., Science 234:1570-1573 (1986).
Pollack and Schultz, Cold Spring Harbor Symp. Quant. Biol. 52:97-104 (1987).
Jacobs, et al., J. Am. Chem. Soc. 109:2174-2176 (1987).
Tramontano, et al., Science 234:1566-1570 (1986).
Tramontano, et al., J. Am. Chem. Soc. 110:2282-2286 (1988).
Janda, et al., Science 241:1188-1191 (1988).
Napper, et al., Science 237:1041-1043 (1987).
Jackson, et al., J. Am. Chem. Soc. 110:4841-4842 (1988).
Janda, et al., J. Am. Chem. Soc. 110:4835-4837 (1988).
Hilvert, et al., Proc. Natl. Acad. Sci. USA 85:4953-4955 (1988).
Benkovic, et al., Proc. Natl. Acad. Sci. USA 85:5355-5358 (1988).
Raso and Stollar, Biochemistry 14(3):584-591 (1975).
Shokat, et al., Angew. Chem. 100:1227-1229 (1988).
Kohen, et al., FEBS Lett. 111(2):427-431 (1980).
Goetzl, et al., Biochemistry 9(5):1267-1278 (1970).
Givol, et al., Biochemistry 10:3461-3466 (1971).
Tabushi, Acc. Chem. Res. 15:66-72 (1982).
Breslow, Science 218:532-537 (1982).
Cram, et al., J. Am. Chem. Soc. 106:4987-5000 (1984).
Chao, et al., J. Am. Chem. Soc. 98:1015-1017 (1976).
Lehn and Sirlin, J.C.S. Chem. Comm. pp. 949-951 (1978).
Tabushi, et al., J. Am. Chem. Soc. 107:5545-5546 (1985).
Zimmerman, et al., J. Am. Chem. Soc. 105:1694-1695 (1983).
Breslow, et al., J. Am. Chem. Soc. 105:1390-1391 (1983), 102:421 (1980).

(List continued on next page.)

Primary Examiner—Charles L. Patterson, Jr.
Attorney, Agent, or Firm—Townsend and Townsend Khourie and Crew

[57] ABSTRACT

Catalytic and reactive polypeptides include a binding site specific for a reactant or reactive intermediate involved in a chemical reaction of interest. The polypeptides further include at least one active functionality proximate the binding site, where the active functionality is capable of catalyzing or chemically participating in the chemical reaction in such a way that the reaction rate is enhanced. Methods for preparing the catalytic peptides include chemical synthesis, site-directed mutagenesis of antibody and enzyme genes, covalent attachment of the functionalities through particular amino acid side chains, and the like.

7 Claims, 19 Drawing Sheets

OTHER PUBLICATIONS

Almog, et al., *J. Am. Chem. Soc.* 97:227 (1975).
Collman, *Acct. Chem. Res.* 10:265–272 (1977).
Chang, et al., *Proc. Natl. Acad. Sci. USA* 70(9):2647–2650 (1973).
Wilkinson, et al., *Nature* 307:187–188 (1984).
Craik, et al., *Science* 228:291–297 (1985).
Schultz, et al., *Biochemistry* 24:6840–6848 (1985).
Dalbadie-McFarland, *Proc. Natl. Acad. Sci. USA* 79:6409–6413 (1982).
Sigal, et al., *J. Biol. Chem.* 259:5327–5332 (1984).
Kaiser, et al., *Science* 226:505–510 (1984).
Corey, et al., *Science* 238:1401–1403 (1987).
Polgar, et al., *J. Am. Chem. Soc.* 88:3153–3154 (1966).
Neet, et al., *Proc. Natl. Acad. Sci. USA* 56:1606–1611 (1966).
Nisonoff, et al., "The Antibody Molecule," Academic Press, pp. 23–27 (1975).
Cochran, et al., *J. Am. Chem. Soc.* 110:7888–7890 (1988).
Webster, D. M., et al., *Int. J. Cancer Suppl.* 3:13–16 (1988).
*Webster's II New Riverside University Dictionary*, "enzyme," p. 437 (1984).
*Hackh's Chemical Dictionary*, "enzyme(s)," p. 242 (1969).
Lerner, R. A., *TIBS* 12, pp. 427–430 (1987).
Tramontano, A., et al., *Proc. Natl. Acad. Sci. USA* 83:6736–6740 (1986).
Schultz, P. G. *Science* 240:426–433 (1988).
Pollack, S. J. et al., *Science* 242:1038–1040 (1988).
Pollack, S. J., et al., *J. Am. Chem. Soc.* 111:1929–1931 (1989).
Lerner, et al., *BioEssays* 9:107–112 (1988).
Blair, et al., *J. Immuol. Meth.* 59:129–143 (1983).
Haimovich, et al., *Biochemistry* 11(13):2389–2398 (1972).
Leatherbarrow, R. J. *Nature* 338:206–207 (1989).
Shokat, K. M., et al., *Nature* 338:269–271 (1989).

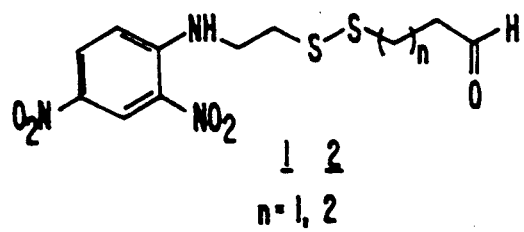
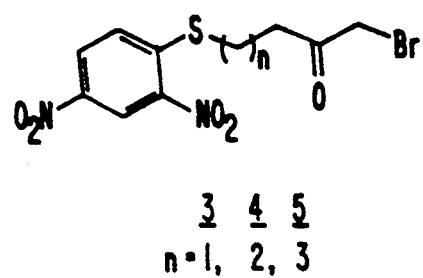
FIG._1.
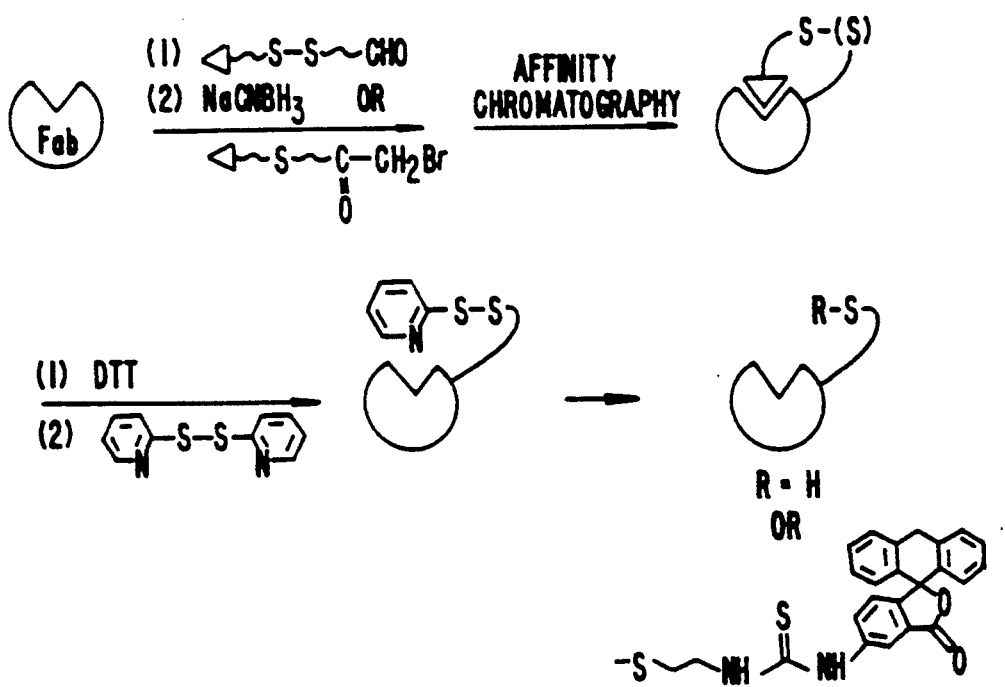
FIG._3.

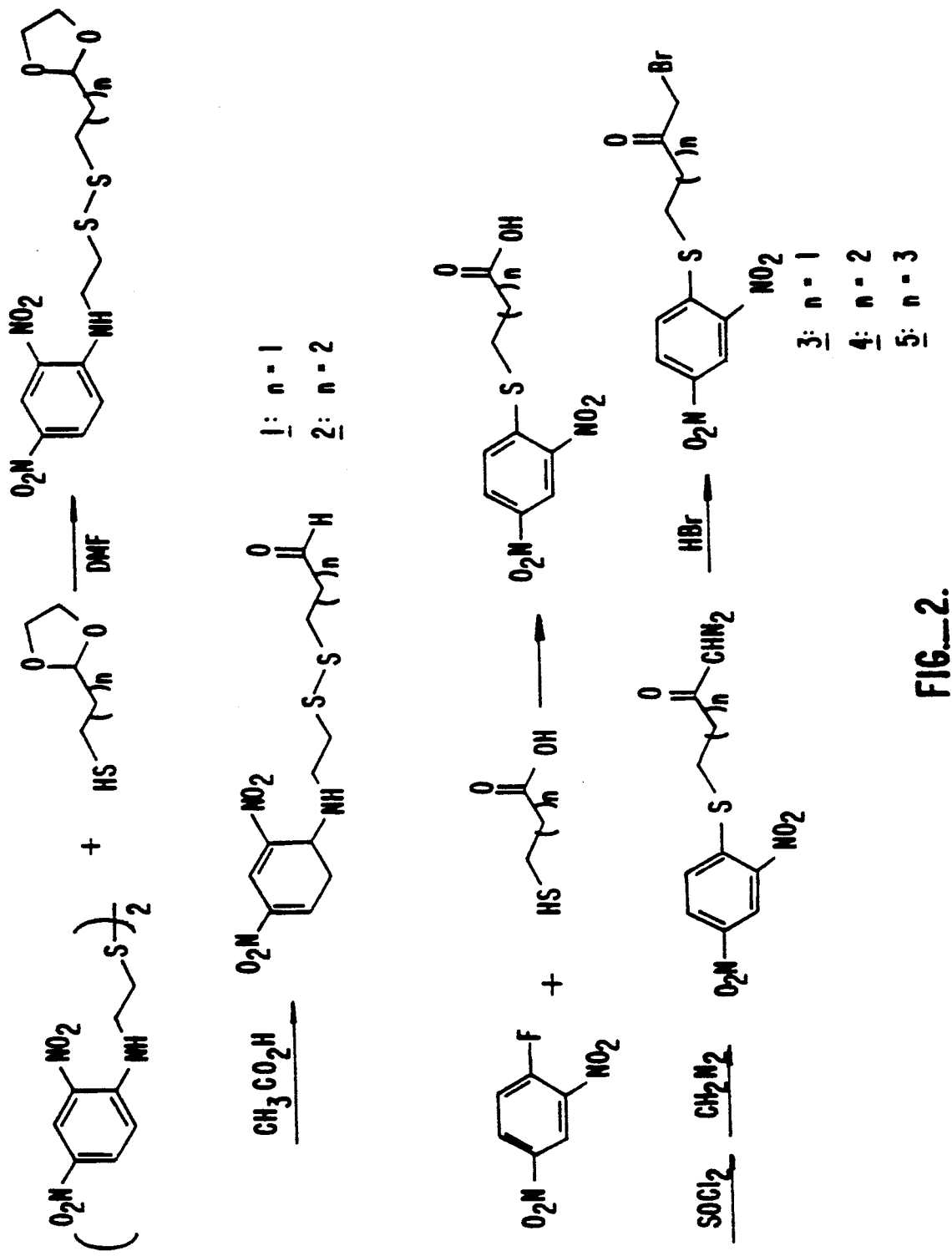
FIG_2.

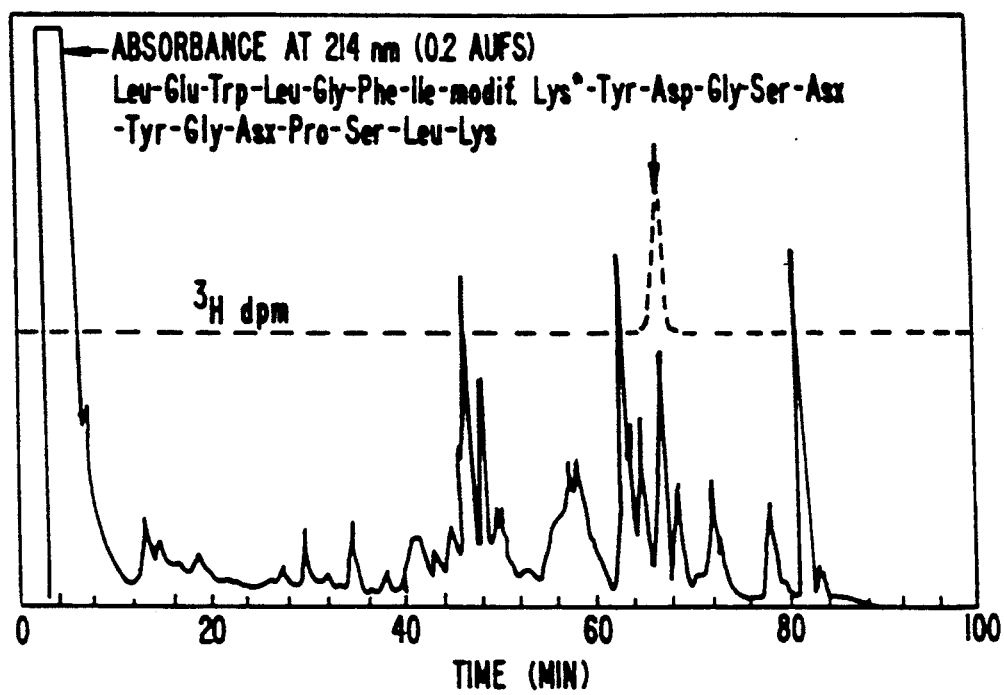
FIG._4.
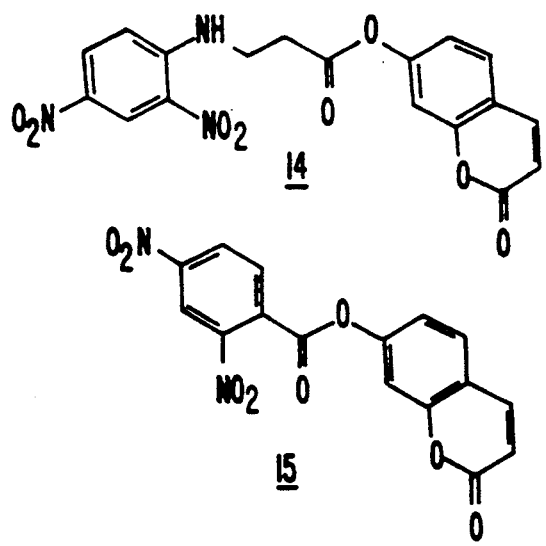
FIG._5.

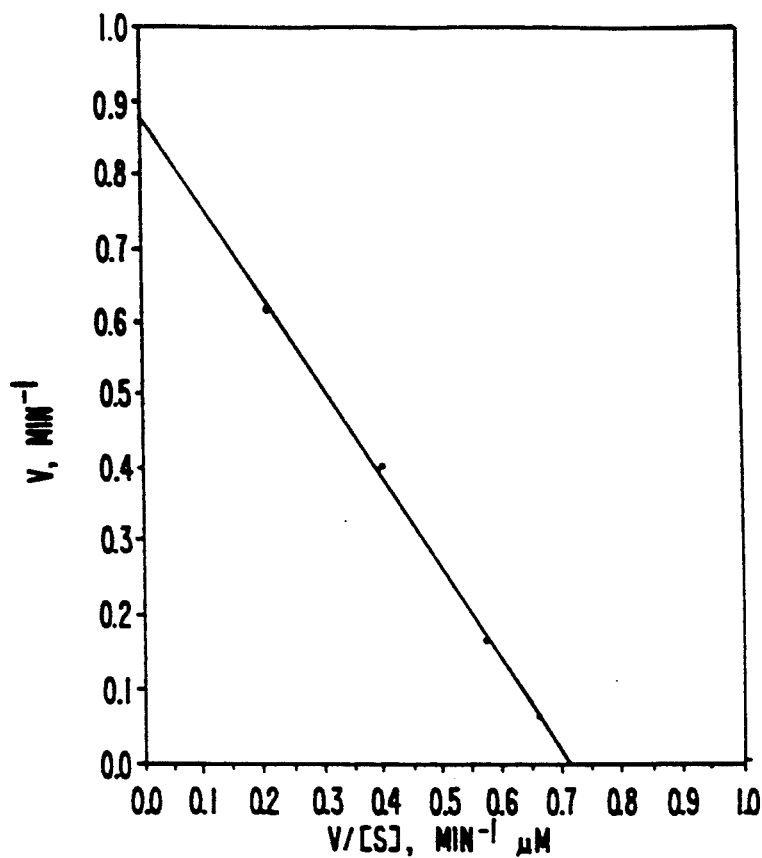
FIG._6.
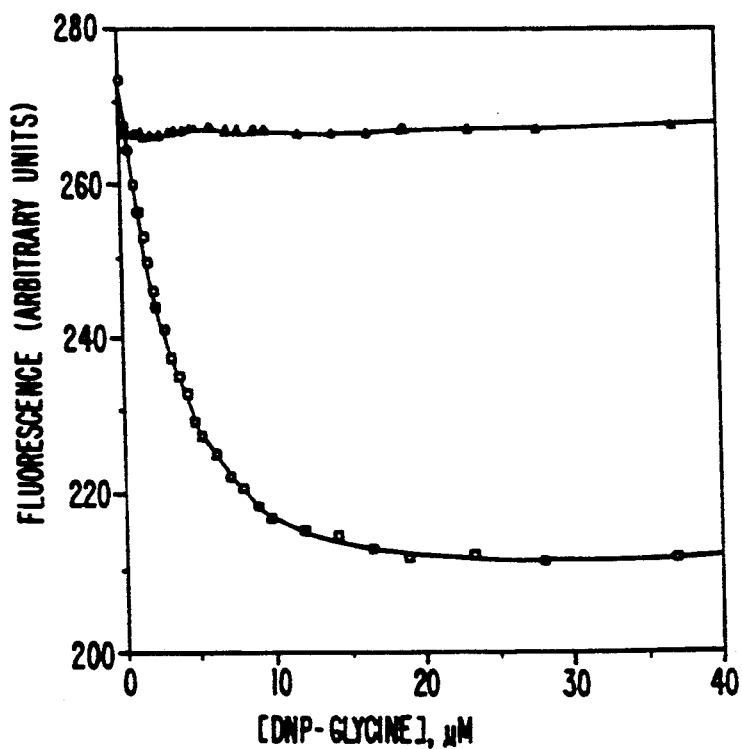
FIG._7.

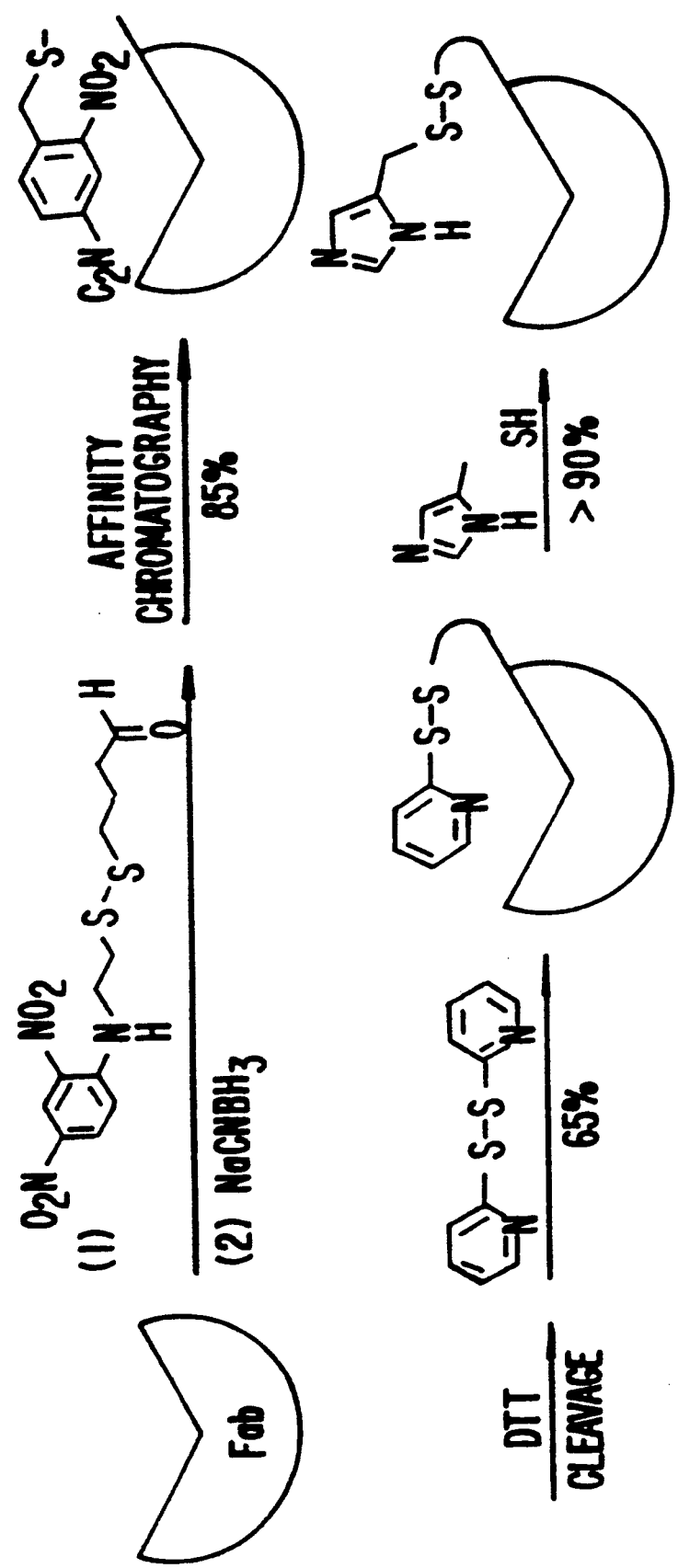
FIG._8.

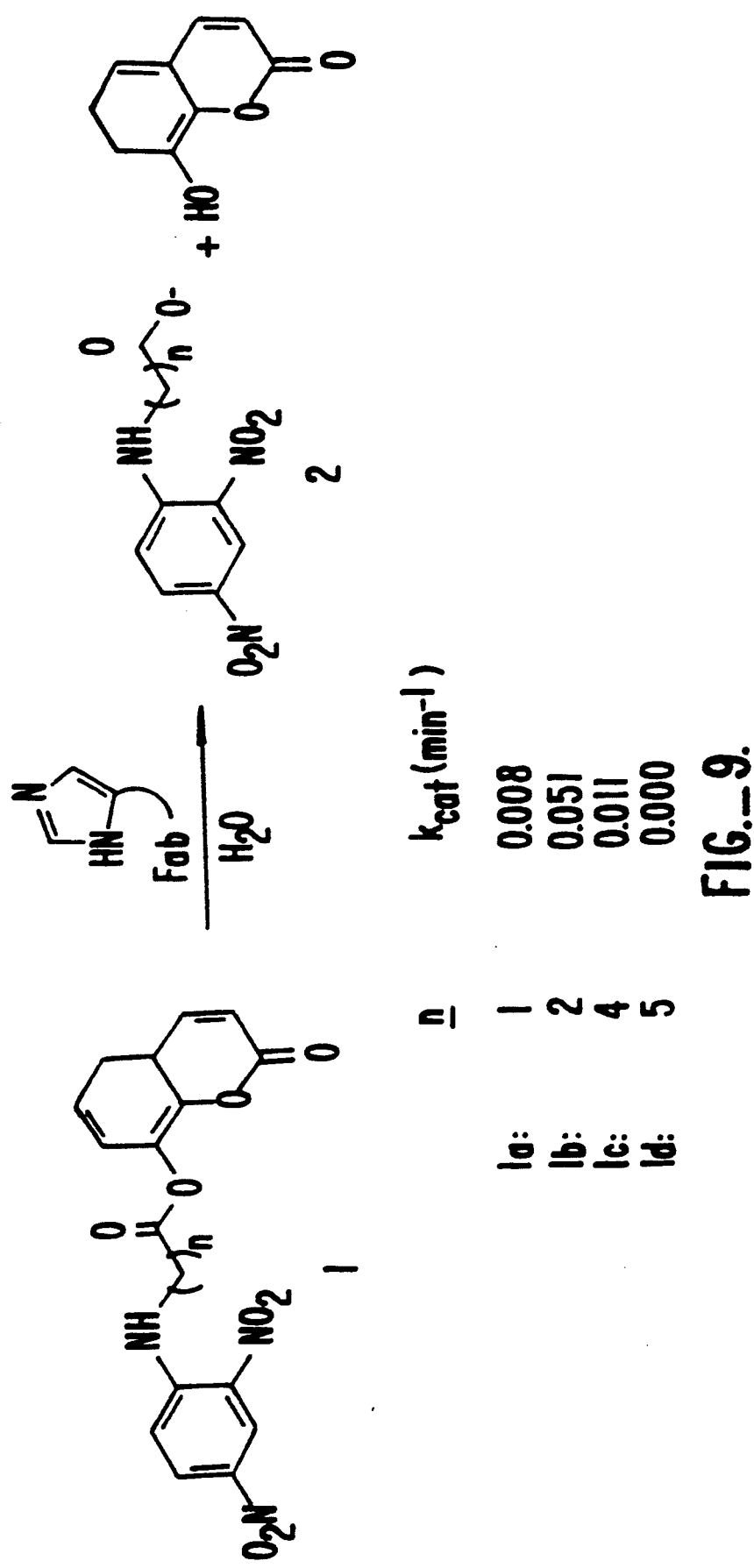
FIG._9.

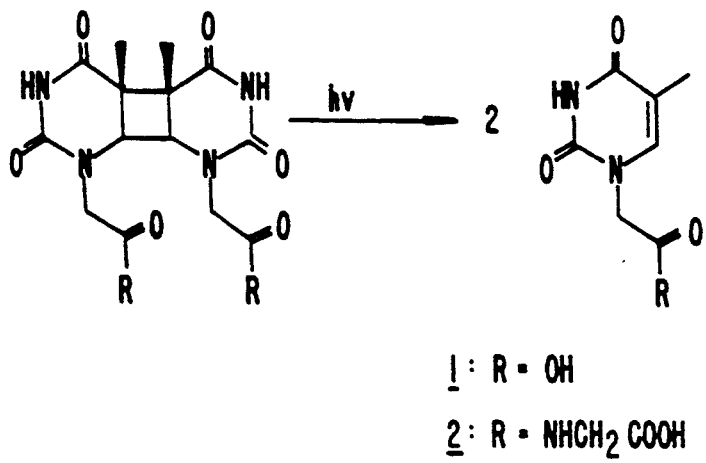
1: R = OH
2: R = NHCH₂COOH
FIG._10.
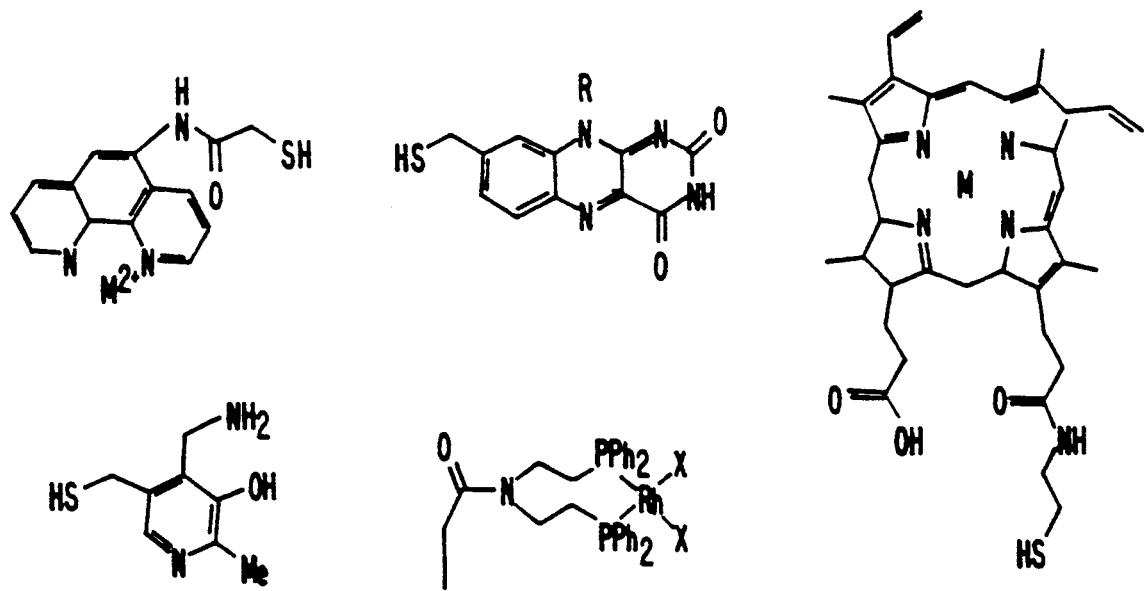
FIG._15.

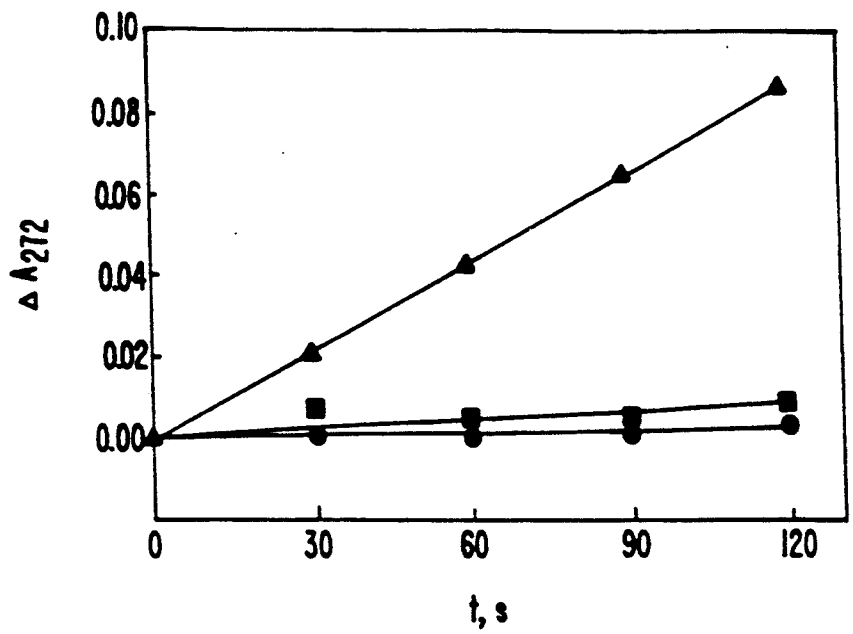
FIG._11a.
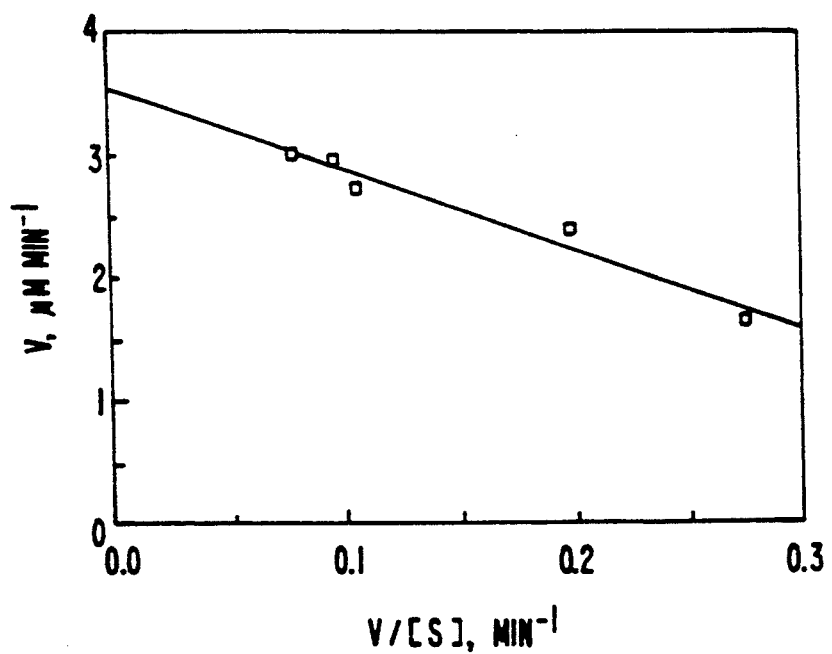
FIG._11b.

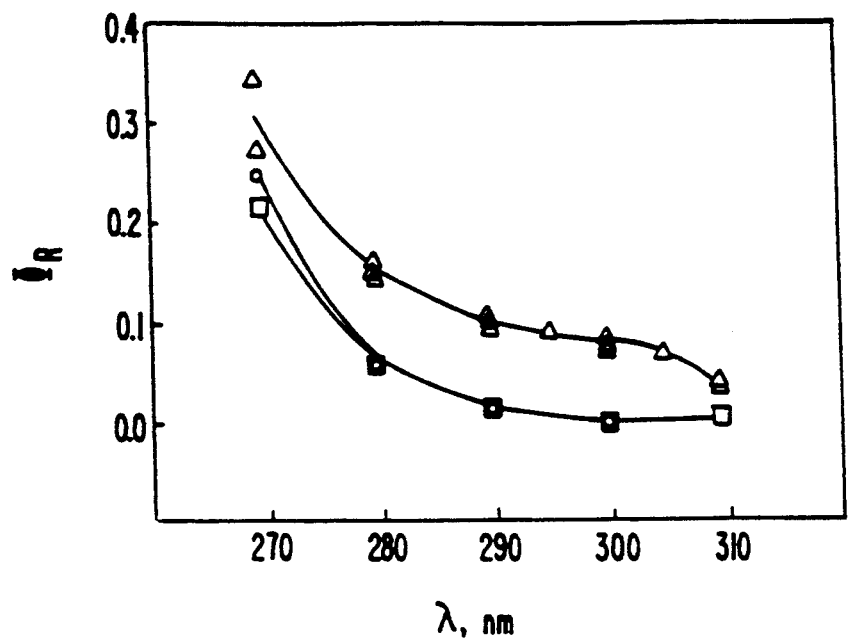
FIG._12a.
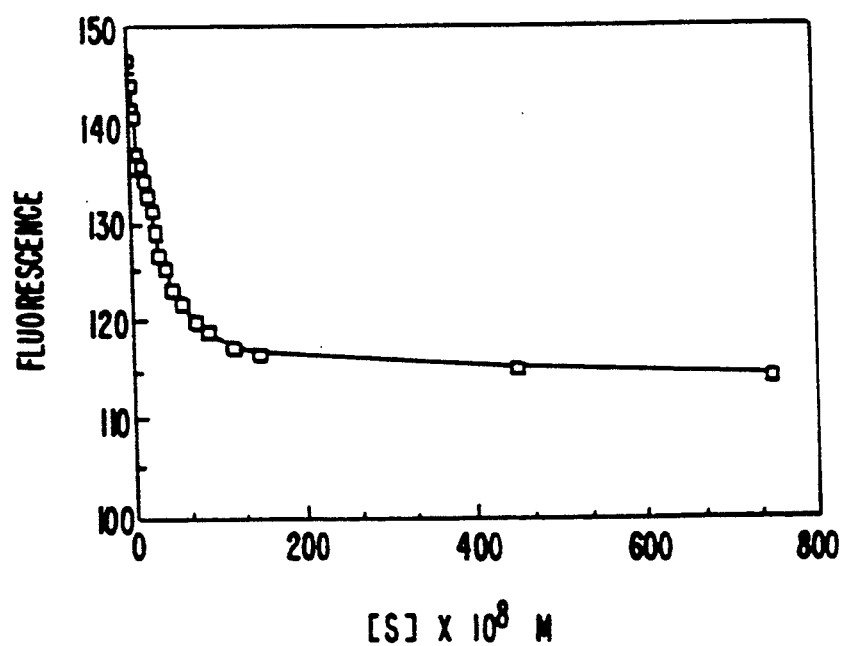
FIG._12b.

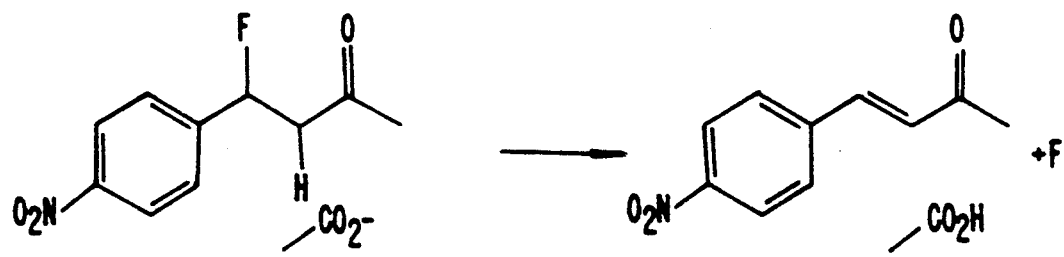
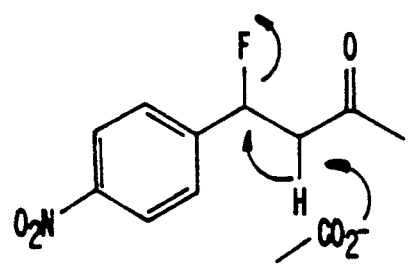
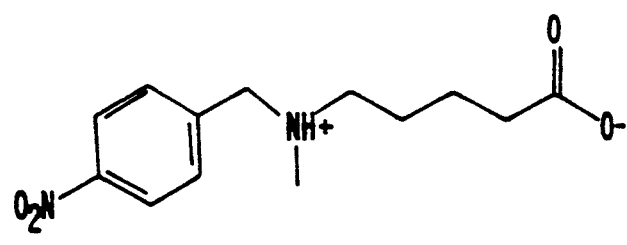
HAPTEN
FIG._13.

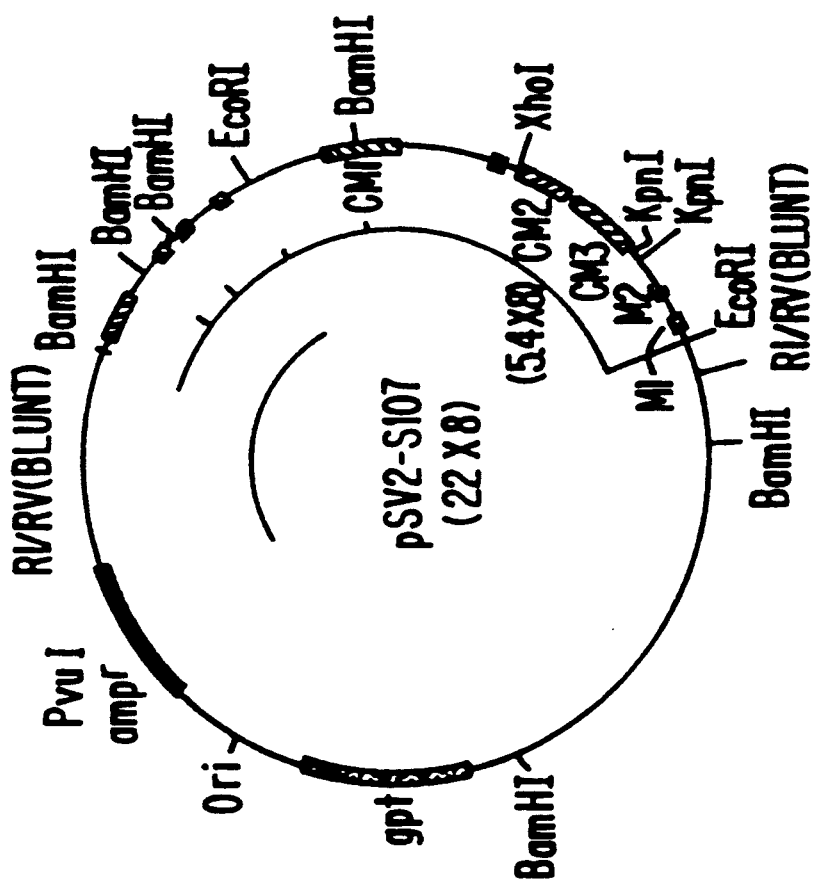
FIG._14A.

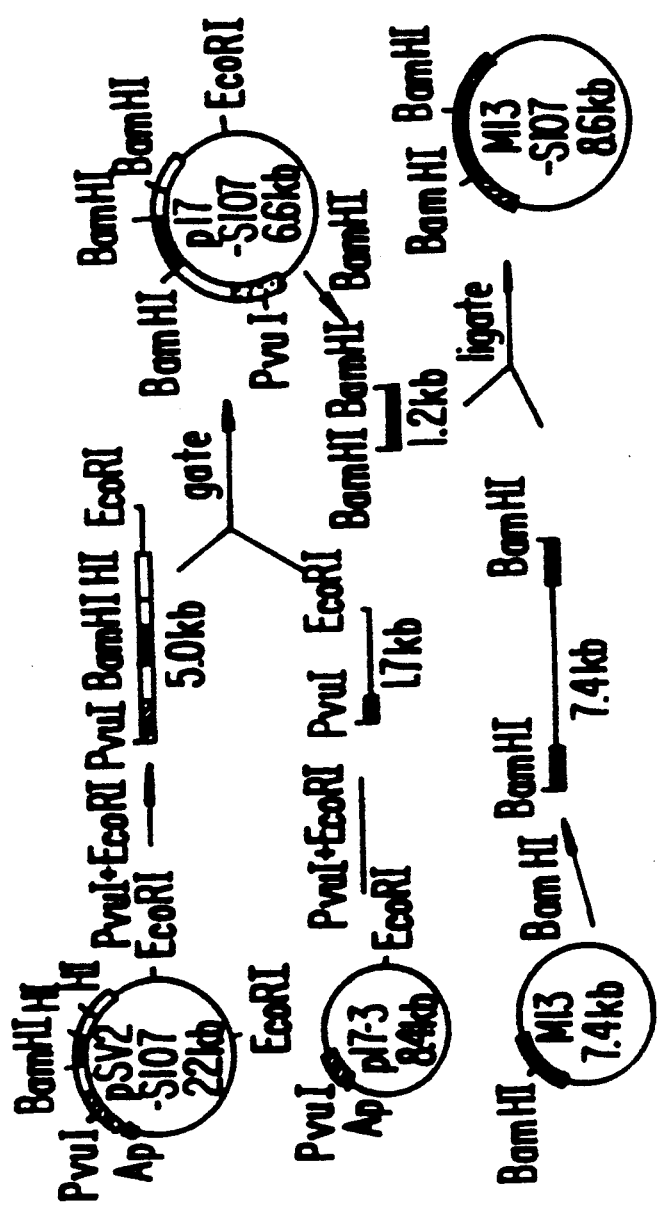
FIG._14B.

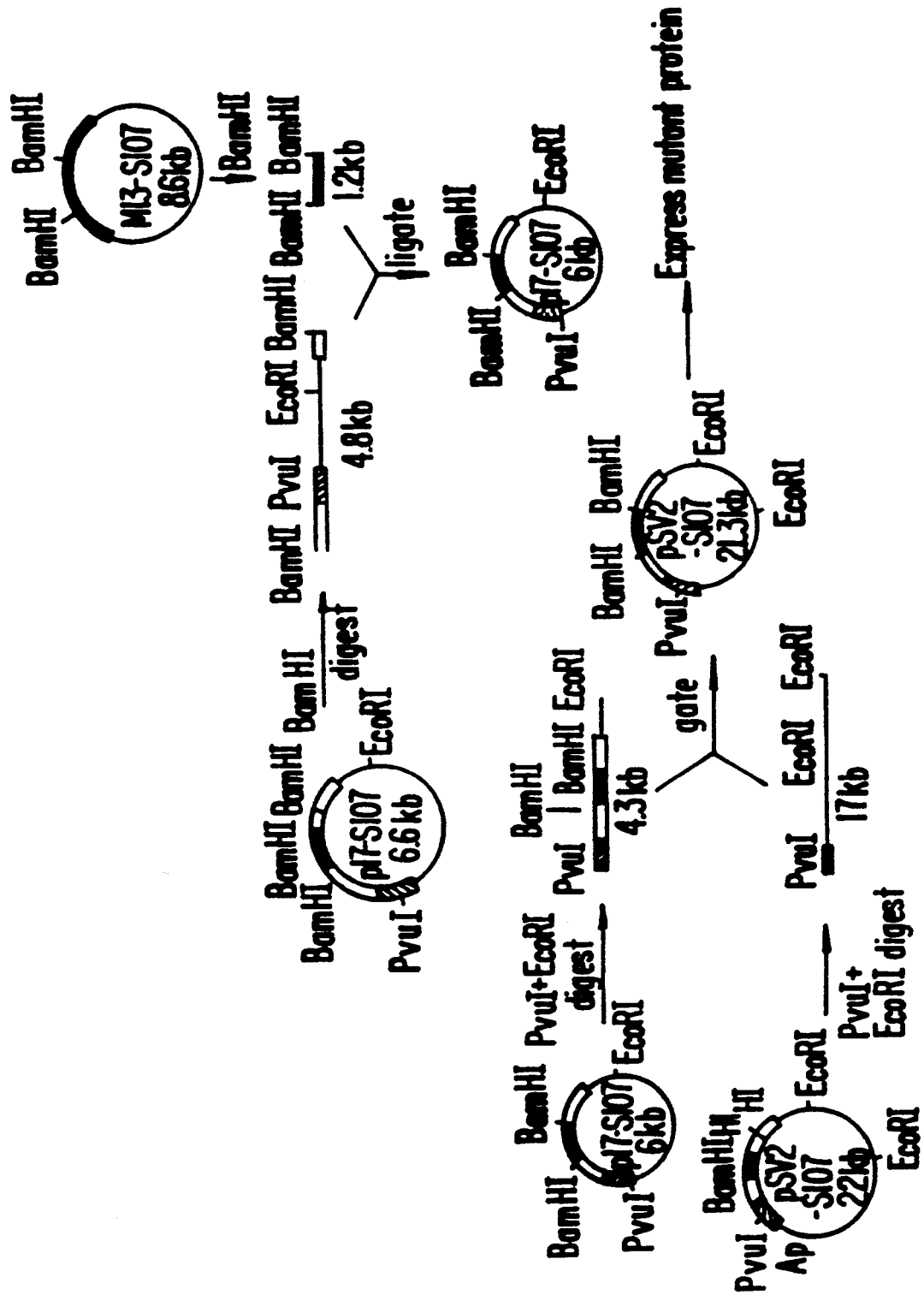
FIG._14C.

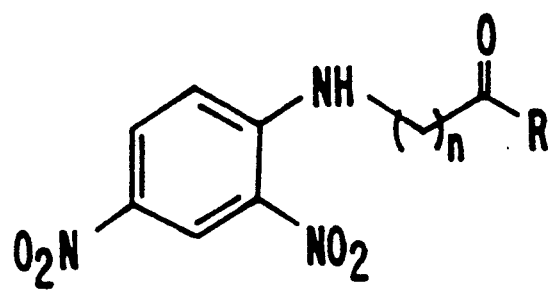
ESTER SUBSTRATES          CARBOXYLIC ACIDS
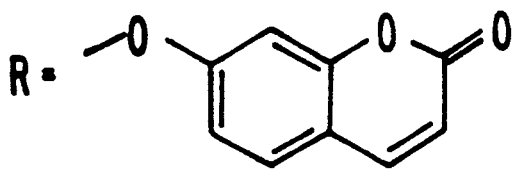     
1 n = 4                   6 n = 3
2 n = 5                   7 n = 4
3 n = 2                   8 n = 5
                          9 n = 6
4  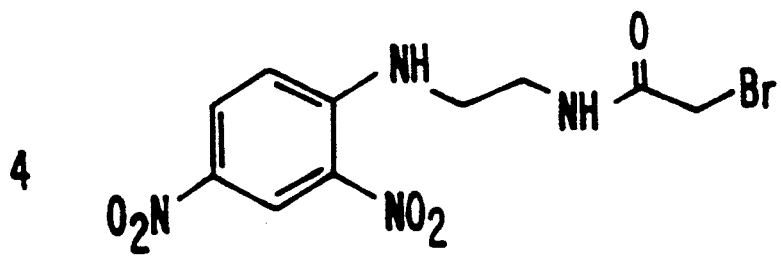
5  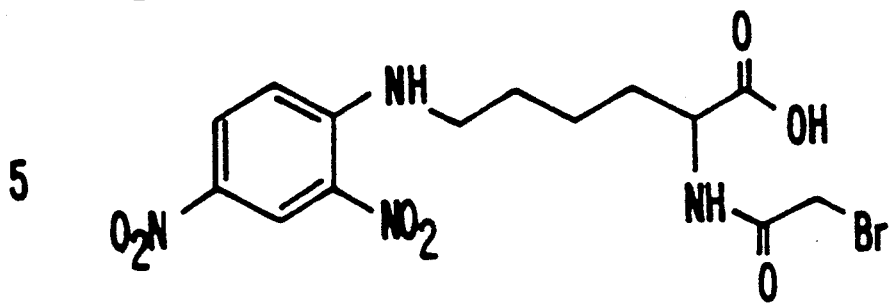
FIG._16.

```
                   20                    40                              60
                                       AatII  SmaI
GACGCGGTTGTAACTCAAGAATCTGCTCTGACGACGTCCCCGGGTGGTACTGTTATCCTG
AspAlaValValThrGlnGluSerAlaLeuThrThrSerProGlyGlyThrValIleLeu
                    5                                 15
                   80                   100                            120
                         BstEII                            BamHI
ACCTGCCGTTCCTCTACCGGTGCGGTAACCACCTCTAACTATGCGAACTGGATCCAGGAG
ThrCysArgSerSerThrGlyAlaValThrThrSerAsnTyrAlaAsnTrpIleGlnGlu
                   25                                 35
        BclI       140                   160                           180
AAACCTGATCATCTGTTTACCGGCCTGATCGGCGGTACTTCCAATCGTGCGCCGGGCGTC
LysProAspHisLeuPheThrGlyLeuIleGlyGlyThrSerAsnArgAlaProGlyVal
                   45                                 55
        AvaII      200                   220                    240
                                                                   NarI
CCGGTCCGTTTCTCTGGTTCCCTGATCGGTGATAAAGCGGCGCTGACCATCACTGGCGCC
ProValArgPheSerGlySerLeuIleGlyAspLysAlaAlaLeuThrIleThrGlyAla
                   65                                 75
                   260          BssHII    280                          300
CAGACCGAAGATGACGCGATGTACTTCTGCGCGCTGTGGTTCCGTAACCACTTCGTGTTT
GlnThrGluAspAspAlaMetTyrPheCysAlaLeuTrpPheArgAsnHisPheValPhe
                   85                                 95
                   320                   340
        KpnI                                     SalI   HindIII
GGTGGTGGTACCAAAGTGACCGTTCTGGGTCAGCCGAAGTCGACCTAAGCTT]
GlyGlyGlyThrLysValThrValLeuGlyGlnProLysSerThr
                  105                            115
```

FIG._17.

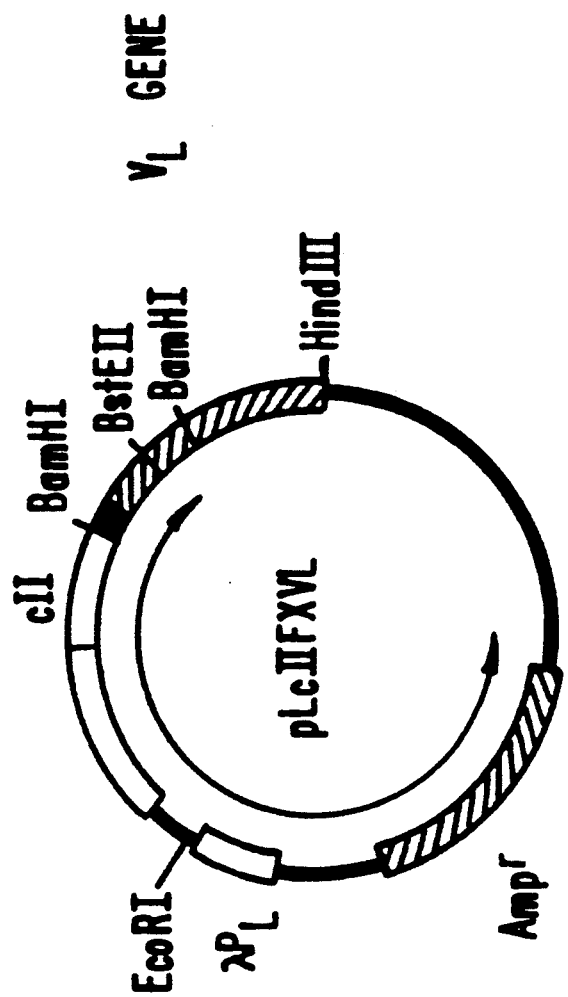
FIG._18.

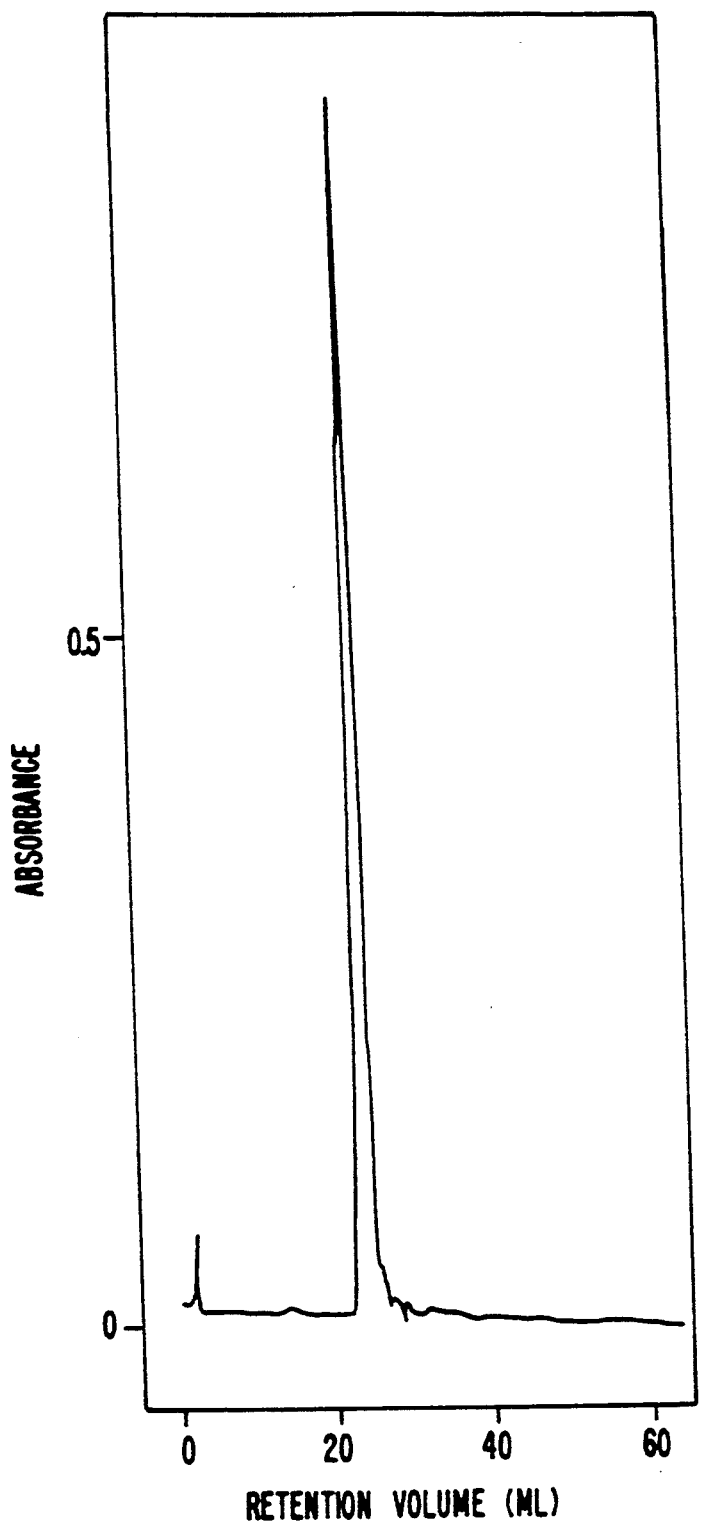
FIG._20.

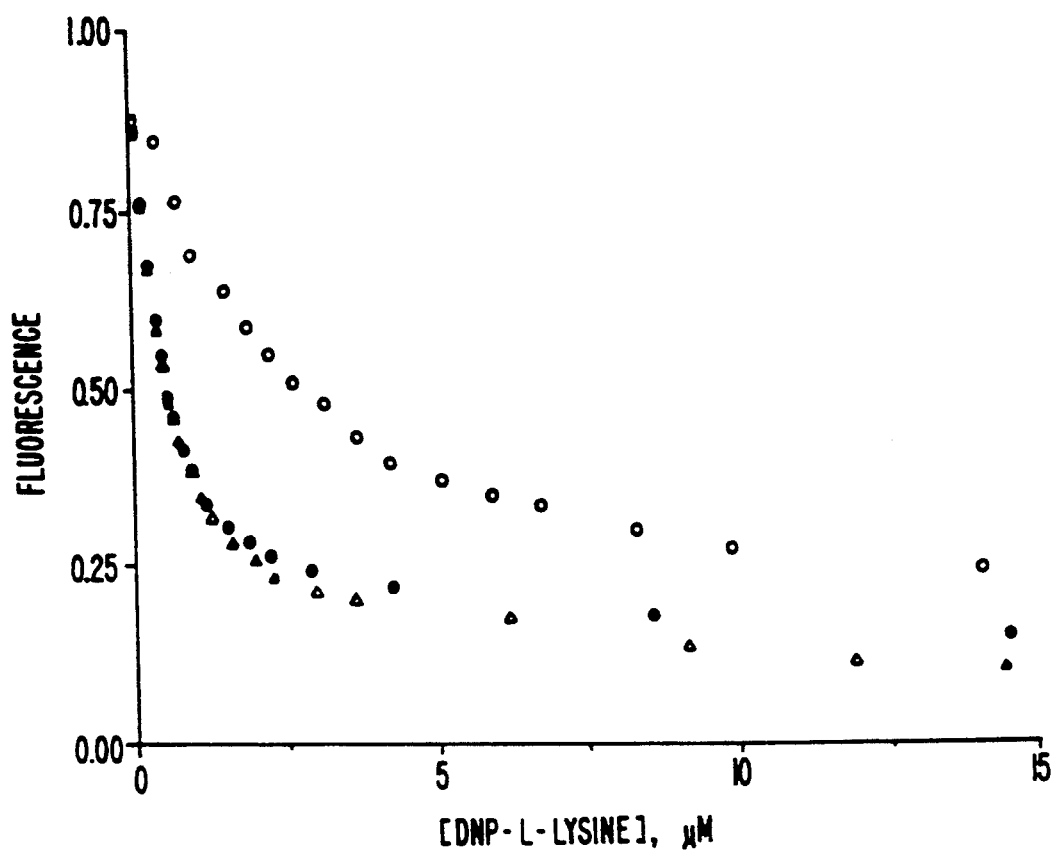
FIG._21.
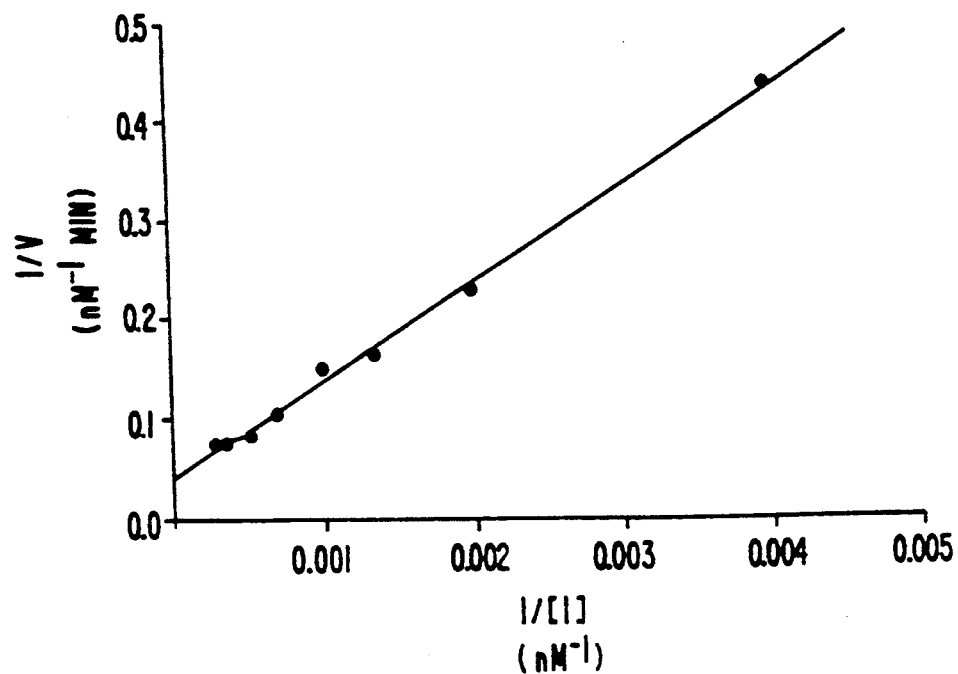
FIG._22.

CATALYTIC AND REACTIVE POLYPEPTIDES AND METHODS FOR THEIR PREPARATION AND USE

This invention was made with Government support under Grant Contract No. AI-24695 awarded by the Department of Health and Human Services, under Grant Contract No. N 00014-87-K-0256, awarded by the Office of Naval Research. The Government has certain rights in this invention, under Grant Contract CHE 8822412 awarded by the National Science Foundation, and under Grant Subcontract C87-101226 awarded by the Department of Energy.

This is a continuation of application Ser. No. 07/404,920, filed Sep. 8, 1989 (pending), which is a continuation-in-part of application Ser. No. 07/273,455, filed Nov. 18, 1988 (now abandoned).

CROSS REFERENCE TO RELATED APPLICATIONS

Application Ser. No. 07/273,786 filed on Nov. 18, 1988, and application Ser. No. 07/337,601, filed on Apr. 13, 1989, both of which name Peter Schultz as the sole inventor, contain related subject matter. The entire disclosures of these related applications are incorporated herein by reference.

BACKGROUND OF THE INVENTION

1. Field of the Invention

The present invention relates generally to methods and compositions producing novel polypeptides including antibodies capable of promoting chemical reactions. More particularly, the present invention relates to methods for modifying polypeptides to include active functionalities capable of promoting chemical reactions.

The ability to catalyze chemical reactions, such as the synthesis, modification, or cleavage of structurally complex molecules, including proteins, nucleic acids, carbohydrates, and the like, would be of great commercial and scientific benefit. To this end, antibodies have been prepared having catalytic activity resulting from the ability of the antibody combining site to selectively stabilize transition state intermediates and to overcome entropic barriers in orienting reactants in particular reactions.

Although significant catalytic activity has been observed with such antibodies, it would be desirable to provide catalytic antibodies and other polypeptides having enhanced catalytic activity and specificity. In particular, it would be desirable to be able to design catalytic antibodies and polypeptides having a combining site with a desired specificity and affinity for the reactant(s) of interest, which antibodies and polypeptides further provide catalytic or other reactive groups proximate the binding site. Such catalytic and reactive groups would be able to chemically participate in the reaction of interest.

2. Description of the Relevant Art

The preparation of catalytic antibodies against haptens that are transition state analogs is described in the following references: Pollack et al. (1986) Science 234:1570–1573; Pollack and Schultz (1987) Cold Spring Harbor Symp. Quant. Biol. 52:97–104; Jacobs et al. (1987) J. Am. Chem. Soc. 109:2174–2176; Tramontano et al. (1986) Science 234:1566–1570; Tramontano et al. (1988) J. Am. Chem. Soc. 110:2282–2286; and Janda et al. (1988) Science 241:1188–1191. The use of antibodies to overcome entropic barriers involved in orienting reaction partners is described in the following references: Napper et al. (1987) Science 237:1041–1043; Jackson et al. (1988) J. Am. Chem. Soc. 110:4841–4842; Janda et al. (1988) J. Am. Chem. Soc. 110:4835–4837; Hilvert et al. (1988) Proc. Natl. Acad. Sci. USA 85:4953–4955; and Berkovic et al. (1988) Proc. Natl. Acad. Sci. USA 85:5355–5358. Polyclonal antibodies have been generated with cofactor binding sites (Raso and Stollar (1975) Biochemistry 14:584–591). The generation of monoclonal antibodies having a cofactor binding site is described in Shokat et al. (1988) Angew. Chem. 100:1227–1229. The generation of affinity labels for antibody combining sites is described by Kohen et al. (1980) FEBS Lett. 111:427–431; Metzger et al. (1970) Biochemistry 9:1267–1278; and Givol et al. (1971) Biochemistry 10:3461–3466. Chemically derivatized hydrophobic and hydrophilic model systems have been shown to afford rate enhancements in hydrolytic and redox reactions by specific substrate binding (Bender et al. (1978) Cyclodextrin Chemistry, Springer-Verlag, Berlin; Tabushi (1982) Acet. Chem. Res. 15:66; Breslow (1982) Science 218:532; and Cram et al. (1978) J. Am. Chem. Soc. 106:4987). Both Cram et al. (1976) J. Am. Chem. Soc. 98:1015 and Lehn and Sirlin (1978) J.C.S. Chem. Comm. 949 have demonstrated that polyether macrocycles derivatized with thiol residues complex and accelerate acyl transfers by factors of $10^3$ to $10^4$ in thiolysis reactions of amino acid ester salts (relative to noncomplexing thiols). Furthermore, cyclodextrins derivatized with pyridoxamines have afforded 100-fold rate accelerations in transamination of pyruvic acid as well as greater than twenty-fold stereo-selectively in a-amino acid synthesis (Tabushi et al. (1985) J. Am. Chem. Soc. 107:5545; Zimmerman et al. (1983) J. Am. Chem. Soc. 105:1694; Breslow et al. (1983) J. Am. Chem. Soc. 105:1390; and Breslow et al. (1980) J. Am. Chem. Soc. 102:423). Baldwin et al. (1975) J. Am. Chem. Soc. 97:227, Collman (1977) Acet. Chem. Res. 10:265; and Traylor (1973) Proc. Natl. Acad. Sci. 78:2647 have shown that cavity containing porphyrins are also capable of mimicking the oxygen binding function of myoglobin as well as the oxidative chemistry of P-450 monoxygenase. Introduction of a free thiol into chiral macrocyclic ether has been shown to promote the transacylation of nitrophenyl glygly ester relative to uncomplexed dipeptide. Lehn and Sirlin (1978) supra. Site-directed mutagenesis has been used in conjunction with high resolution x-ray crystallography to analyze the structure of enzyme binding sites and the function of such sites in catalysis. Wilkinson et al. (1984) Nature 307:187–188; Craik et al. (1985) Science 228:291–297; Schultz et al. (1985) Biochemistry 24:6840–6848; Dalbadie-McFarland (1982) Proc. Natl. Acad. Sci. USA 79:6409–6413; and Sigal et al. (1984) J. Biol. Chem. 259:5327–5332. A cysteine in the active region of the enzyme papain has been modified with a flavin cofactor. Kaiser et al. (1984) Science 226:505–510. A thiol has been introduced into the enzymes staphylococcal nuclease and RNase S and subsequently derivatized with an oligonucleotide. Corey et al. (1987) Science 238:1401–1403. The active site serine of subtilisin has been chemically converted to a cysteine. Bender et al. (1966) J. Am. Chem. Soc. 88:3153–3154 and Koshland et al. (1966) Proc. Natl. Acad. Sci. USA 56:1606–1611. Antibodies generated against positively charged haptens contain complementary aspartate and glutamate residues (Nisonoff et al. (1975) The Antibody Molecule, Academic Press, pp. 23-27). The experimental data in Example 4 was published in Cochran et al. (1988) J. Am. Chem. Soc. 110:7888-7889.

SUMMARY OF THE INVENTION

Using the compositions and methods of the present invention, novel catalysts and promoters are provided to enhance the rate of chemical reactions. In some cases, reactions may be catalyzed where no natural catalysts exist. The compositions and methods of the present invention are particularly suitable for the synthesis, modification, and cleavage of structurally complex molecules such as proteins, nucleic acids, carbohydrates, and the like.

According to the present invention, polypeptides are provided which are capable of promoting a chemical reaction involving the conversion of one or more reactants to one or more products. Such polypeptides include a binding site specific for at least one reactant or reaction intermediate and an active functionality proximate the binding site which functionality is capable of chemically modifying the bound reactant. The active functionality may be provided by the side chain of an amino acid located proximate the binding site, where the side chain may be naturally-occurring or synthetic (other than naturally-occurring), or may be provided by a separate catalytic or reactive group covalently attached to an amino acid side chain. When the active functionality is a naturally-occurring amino acid side chain or a separate catalytic or reactive functionality covalently attached to a naturally-occurring amino acid side chain, the polypeptide will be other than an enzyme, usually having the structure of an antibody or antibody fragment. When the active functionality is a synthetic amino acid side chain, the polypeptide may be any polypeptide having the desired binding site, usually having the structure of an antibody, antibody fragment, enzyme, or enzyme fragment. Suitable catalytic and reactive functionalities include enzyme cofactors, metal complexes, electrophiles, nucleophiles, acidic groups, basic groups, photosynthesizers, alkylating agents, oxidizing agents, and reducing agents.

Methods for preparing catalytic and reactive polypeptides according to the present invention include both synthetic and recombinant production of polypeptides where a naturally-occurring amino acid sequence (e.g., an antibody or enzyme) is modified by the substitution and/or addition of natural and synthetic amino acids proximate the binding site, as well as post-translational modification of such polypeptides. Post-translational modification of the polypeptides may be accomplished by the covalent attachment of the active functionality to a suitable side chain of an amino acid proximate the binding site. In some cases, it will be desirable to prepare the polypeptides having a suitable amino acid for covalent linkage by recombinant techniques, typically by providing a cysteine, histidine, lysine, serine, tryptophan, or tyrosine, proximate the binding site. Alternatively, polypeptides which have not been sequenced may be modified by combining a ligand including the active functionality with the polypeptide, where the active functionality is cleavably attached to the polypeptide. After the ligand combines with the binding site, the cleavable active functionality is covalently attached to an amino acid proximate the binding site. The attachment of the active functionality to the ligand is then cleaved and the ligand removed from the polypeptide, leaving the active functionality covalently attached proximate the binding site. The active functionality may itself comprise the catalytic or reactive group of interest, or may be further selectively modified with another functionality which can act as the catalytic or reactive group of interest. In addition to all of these methods, catalytic and reactive antibodies may be prepared by eliciting them against a hapten having a particular structure which is chosen to yield antibodies having preselected amino acids proximate the binding site. Such antibodies will be able to bind reactants, reactive intermediates, or transition state analogs involved in the reaction of interest, and will further have specifically located amino acid side chains selected to enhance the reaction rate.

The catalytic and reactive polypeptides of the present invention are useful for promoting chemical reactions involving the conversion of one or more reactants to one or more products. A reaction mixture including the reactant(s) is exposed to the polypeptide, resulting in promotion of the reaction rate. In the case of catalytic functionalities, the polypeptide will be conserved, while in the case of reactive functionalities, the polypeptides will be consumed.

In the specific embodiments, the catalytic and reactive polypeptides may be prepared by first producing antibodies to a reactant or reactive intermediate analog, typically a transition state analog or multisubstrate analog, involved in the chemical reaction of interest. Conveniently, monoclonal antibody techniques will be utilized in order to obtain a source of homogeneous antibodies of uniform specificity. Once the antibodies are obtained, they will frequently display a certain level of catalytic activity based on their ability to stabilize a transition state or strain a ground state involved in a chemical reaction or their ability to reduce entropic barriers involved in positioning two or more reactants involved in the reaction. The present invention provides for the enhancement of such catalytic activity by modification of the antibody or a fragment thereof to provide an active functionality proximate the binding site defined by the antibody. The active functionality may be a naturally-occurring amino acid side chain which is positioned relative to the binding site so that it is able to interact with the reactant(s) or reaction intermediate in such a way to promote the reaction rate. Alternatively, the active functionality may be a synthetic amino acid side chain or be covalently attached to the side chain of an amino acid located in the proper position relative to the antibody binding site.

BRIEF DESCRIPTION OF THE DRAWINGS

FIG. 1 illustrates the cleavable affinity labels used in Example 1 of the Experimental section.

FIG. 2 outlines the methods for synthesizing the affinity labels of FIG. 1.

FIG. 3 illustrates the strategy for introducing a thiol functionality into the binding site of MOPC 315 in Example 1.

FIG. 4 is a high pressure liquid chromatography profile of the tryptic digest of the heavy chain of Fab labeled with 2 (FIG. 1) monitored by UV absorbents (solid line) and radioactivity (dashed line), as described in Example 1.

FIG. 5 illustrates the DNP-containing esters utilized as substrates for reaction with thiolated Fab in Example 1.

FIG. 6 is an Eadie-Hofstee plot of cleavage of ester 14 by thiolated Fab labeled with 2 in Example 1.

FIG. 7 illustrates the results of a fluorescence quenching binding assay for DNP-glycine with fluorescein-Fab adduct (□) versus control with fluorescein plus underivatized Fab (▲). Fluorescence quenching experiments were carried out at 10° C. using 492 nm for excitation and measuring emission at 521 nm. The fluorescein-Fab adduct was diluted with assay buffer (above) to 0.10 μM. Aliquots of 2,4-DNP-glycine were added and, after mixing, the fluorescence observed. Free N-fluoresceinthioureido-2-mercapthoethylamine and underivatized Fab, each at 0.10 μM, were treated in a similar experiment.

FIG. 8 illustrates the strategy for modifying the Fab fragment of MOPC 315 to introduce an imidazole at the binding site in Example 2.

FIG. 9 illustrates the hydrolysis reaction catalyzed by the imidazole-antibody adduct of Example 2.

FIG. 10 illustrates the cis, syn-thymine dimer utilized as a hapten in Example 3.

FIG. 11(a) illustrates the increase in absorbants at 272 nm (thymine monomer) as a function of irradiation time for reaction mixtures containing 25 AM dimer 1 and 3 μM antibody 15F1-3B 1[▲], 3 μM MOPC 315 (dinitrophenyl specific) [·], or no antibody [■]; and (b) Eadie-Hofstee plot for the antibody-sensitized cleavage dimer 1.

FIG. 12(a) is an action spectrum showing the dependence of the quantum yield for monomer formation on the wavelength of irradiation. The reaction mixtures containing 264 μM hapten 2 and 3 μM dimer-specific antibody 15F1-3B1 [Δ]or one of the non-specific antibodies MOPC 315 [□] and MOPC 167 [°]; and (b) fluorescence (arbitrary units:excitation:280 nm, emission:348 nm) of the antibody 15F1-3B1 as a function of added ligand 2. Fluorescence quenching experiments were performed with 0.2 μM antibody at 18° C. in the same buffer used for the photolysis experiments.

FIG. 13 illustrates the elimination reaction of HF from fluoroketone substrate 1 and hapten 2 of Example 4.

FIG. 14 (A, B and C) outline the preparation of the site-directed cysteine mutant of antibody S107 in Example 5.

FIG. 15 illustrates the reagents and substrates 1-5 utilized in Example 5. In this Figure, the symbol "M" represents a metal atom, the symbol "PPh$_2$" represents diphenyl phosphine, and the symbol "X" represents an additional ligand bonded to the rhodium atom.

FIG. 16 illustrates the structures of the ligands, substrates, and affinity labels employed in Example 6 in the Experimental section herein.

FIG. 17 illustrates the nucleotide and corresponding amino acid sequences for the synthetic MOPC315 V$_L$ described in Example 6 in the Experimental section herein.

FIG. 18 illustrates the expression vector pLcIIFXVL which was used to produce Y34FcII-V$_L$ fusion protein in Example 6 in the Experimental section herein.

FIG. 20 is a gel filtration analysis of Fv(Y34H$_L$) produced in Example 6 in the Experimental section herein.

FIG. 21 is a plot of Fv fluorescence titration with DNP-L-lysine as described in Example 6 of the Experimental section herein. Fv(315)(·),Fv(Y34F$_L$)(Δ), or Fv(Y34H$_L$) (o)(400 μl, 450-500 nM, $\epsilon_{280nm} = 37,500$ M$^{-1}$) in 100 mM potassium phosphate, pH 6.8 (buffer A), was titrated with solutions of 10-100 μM DNP-L-lysine ($\epsilon_{360nm} = 17,500$ M$^{-1}$) in buffer A while monitoring the protein fluorescence (excitation: 282 nm; emission: 343nm). Fluorescence was corrected for the change in volume. Dissociation constants (K$_D$) were determined by a modified Scatchard analysis.

FIG. 22 is a Lineweaver-Burke plot of initial rate data obtained for the hydrolysis of 1 as described in Example 6 of the Experimental section herein. Four μl of a 100-fold concentrated solution of substrate 1 in DMSO was added to the 400 μl of Fv (115 ra4) in buffer A while monitoring 7-hydroxycoumarin fluorescence at 25° C. (excitation:355 nm; emission: 457 nm). A standard of 7-hydroxycoumarin was added at the completion of each assay to assess quenching of coumarin fluorescence by DNP at high substrate concentrations. The buffer background rate was subtracted from the initial rates. Each point represents the average velocity of at least duplicate experiments. Factor X, Factor Xa, or Russell's viper venom had no hydrolytic activity towards 1.

DESCRIPTION OF THE SPECIFIC EMBODIMENTS

Figure 19:
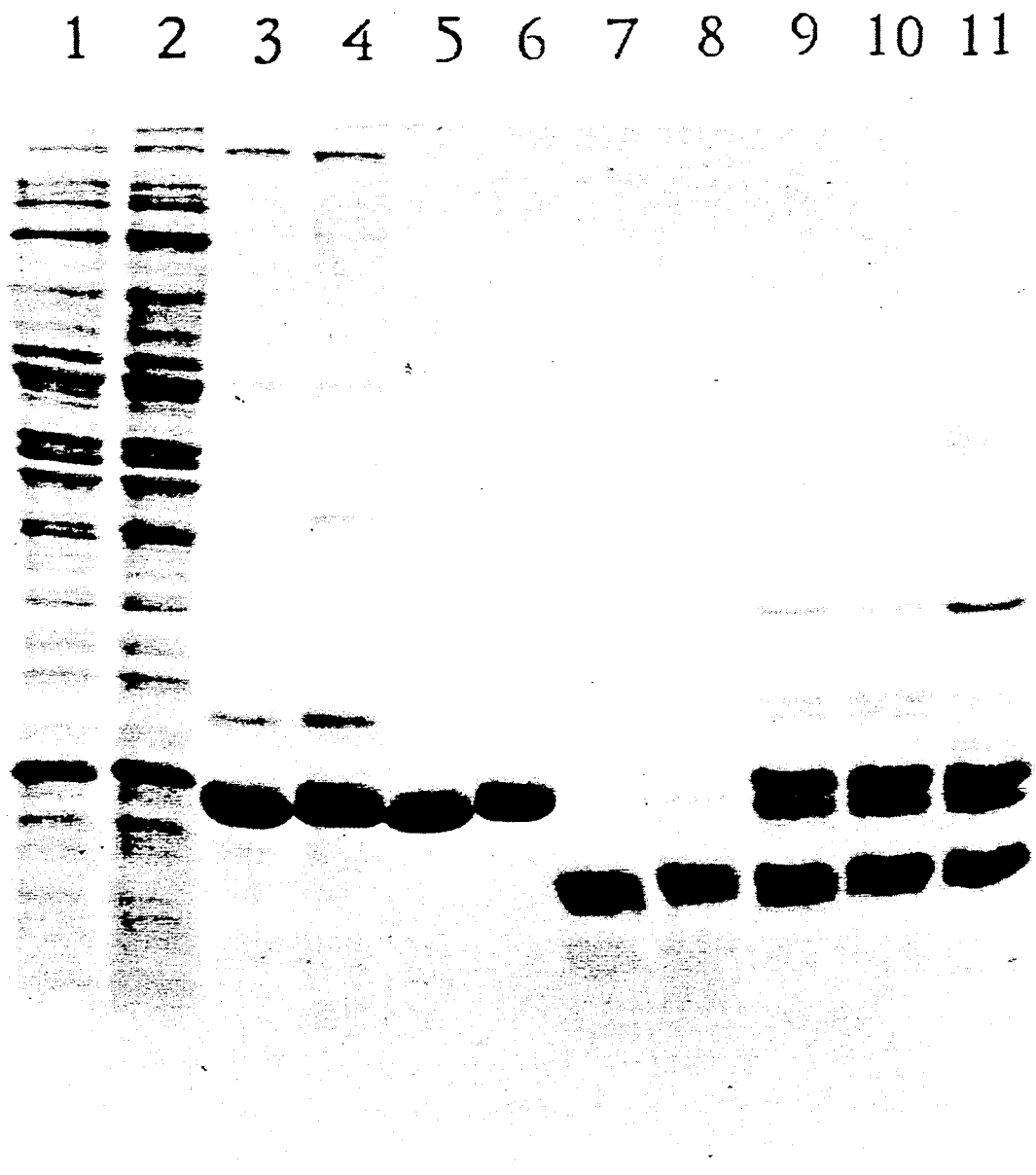
FIG. 19 is an SDS-PAGE analysis of various stages in the production of the mutant Fv proteins produced in Example 6 in the Experimental section herein.

Novel catalytic and reactive polypeptides are capable of promoting a chemical reaction involving the conversion of reactants to products. The polypeptides comprise a binding site capable of specifically attaching to the reactants or reactive intermediates and an active functionality located proximate the binding site. The active functionality will interact with the reactants or reactive intermediates after binding by the polypeptide in order to enhance the reaction rate, either by a catalytic or a reactive mechanism. The polypeptides are used by combining with reactants under conditions suitable for the desired reaction.

The polypeptides of the present invention may be natural or synthetic, with the term natural generally referring to polypeptides produced by and/or isolated from living biological organisms, e.g., cell culture, animal tissue, plant sources, and the like, and the term synthetic generally referring to polypeptides produced by recombinant DNA methods and by chemical synthesis techniques, e.g., solid phase synthesis techniques. The polypeptides may be a single chain, or include multiple chains, and may be glycosylated or free from glycosylation. The size of the polypeptide is not critical, with polypeptides being in the range from 10 kilodaltons (kD) to 1000 kD, usually being in the range from 20kD to 200 kD. The polypeptides may be in the form of natural biological proteins, such as antibodies, enzymes, hormones, lectins, cellular receptors, and fragments thereof, as well as other proteins capable of specifically binding target ligands which include reactants, reactive intermediates, and transition state analogs involved in the chemical reaction of interest. Usually, in the case of such known forms of biologic proteins, the structure of the protein will be modified in a predetermined matter in order to introduce the active functionality of interest. In some cases, however,, it will be possible to merely alter the amino acid sequence of the known structure in order to obtain proper placement of the active functionality of interest. Such modified proteins will generally retain the ability to mimic the naturally-occurring protein from which they have been derived and, in particular, will retain the ability to bind to the target ligand of interest.

Alternatively, the polypeptides of the present invention may assume novel configurations which are not characteristic of known classes of biological proteins. In such cases, the polypeptides will be synthesized, either by recombinant techniques or by solid phase synthesis techniques, to provide a product having a desired sequence and structural configuration which will allow for binding of the polypeptide to the reactant, reactive intermediate, or transition state analog (target ligand) of interest.

Regardless of form, it is necessary that the polypeptide have a binding site with affinity for at least one reactant or reactive intermediate, or transition state analog of the chemical reaction of interest. The affinity will be at least about $10^{-3}$ $M^{-1}$, usually being at least about $10^{-4}$ $M^{-1}$, preferably being at least about $10^{-5}$ $M^{-1}$, and more preferably being at least about $10^{-6}$ $M^{-1}$ or higher. In the case of modified polypeptides, i.e., those which have changes in their amino acid sequence or active functionalities covalently bound proximate the binding site, there should be no substantial loss of binding affinity as a result of the modification, and the modified polypeptide should generally meet the affinity levels just set forth even if some loss of affinity has occurred.

Polypeptides having the desired affinity are most easily prepared by raising antibodies against a reactant, reactive intermediate, or transition state analog which is involved in the chemical reaction of interest. Conveniently, the reactant, reactive intermediate, or transition state analog is prepared and utilized as a hapten in preparing the antibodies having desired affinities. Methods for preparing antibodies to particular transition states are taught in Pollack and Schultz (1987) Cold Spring Harbor Symp. Quant. Biol. 52:97≅104; Jacobs et al. (1987) J. Am. Chem. Soc. 109:2174–2176; Tramontano et al. (1986) Science 234:1566–1570; Napper et al. (1987) Science 237:1041–1043; Jackson et al. (1988) J. Am. Chem. Soc. 110:4841–4842; and Janda et al. (1988) J. Am. Chem. Soc. 110:4835–4837, the disclosures of which are incorporated herein by reference.

The binding site of the polypeptide is defined by a grouping of amino acids which are capable of specifically attaching to the reactant or reactive intermediate of interest. The binding site will usually include from about 2 to 15 amino acids, more usually including from about 2 to 10 amino acids, where the amino acids may be contiguous or separated along the primary sequence of the polypeptide. When the amino acids are not contiguous, they will usually be brought together by the folding (secondary structure) of the polypeptide. The binding site will usually define a cavity or other three-dimensional structure which is complementary with a portion of the reactant or reactive intermediate which is being bound. In particular, the side chains of the amino acids within the binding site will interact with the particular structure (referred to as an epitope or determinant site in the case of antibody binding) on the reactant or reactive intermediate being bound.

An active functionality according to the present invention is a moiety or functional group which is covalently attached to the polypeptide proximate the binding site and which is capable of catalytically or reactively interacting with the bound reactant, reactive intermediate, or transition state analog to promote the reaction. The active functionality may be located within the three-dimensional structure of the binding site or may be located about the periphery of the binding site, but will be sufficiently close to the binding site to provide the necessary interaction with the reactant or reactive intermediate. The precise distance between the active functionality and the binding site is not critical but will usually be less than about 20Å, more usually being less than about 10Å, and preferably being less than about 5Å. The distance of the active functionality from the binding site, however, may be larger and it is important only that the active functionality on the polypeptide be sufficiently close to the bound reactant or reactive intermediate to provide the desired interaction and promotion of the reaction rate.

The polypeptides of the present invention will usually be able to promote a chemical reaction by two distinct mechanisms. By the first mechanism, the polypeptide binds to a transition state involved in the chemical reaction, stabilizing the transition state and thereby enhancing the reaction rate. By the second mechanism, the active functionality will provide a catalytic or reactive interaction with the bound reactant or reactive intermediate. Such interactions will further enhance or promote the reaction rate beyond the enhancement attributable to transition state stabilization alone. In some cases, however, the polypeptides of the present invention will provide only the second of these mechanisms.

The active functionalities of the present invention will be capable of catalytic interactions as well as reactive interactions where the functionality is consumed during the reaction. Such interactions include proton and hydrogen abstraction, Lewis acid catalysis, electron transfer, photosensitization, nucleophilic or electrophilic addition to substrate, general acid or base catalysis, specific or base catalysis, and the like. Catalytic or reactive groups include naturally-occurring cofactors and derivatives thereof, metal complexes (e.g., chelates), electrophiles, nucleophiles, basic and acidic groups (including Lewis acids), redox active molecules, photoactive molecules, alkylating agents, reactive radicals, and the like.

The active functionalities of the present invention include virtually any chemical group which may be attached to the polypeptide and which may be able to provide a desired catalytic or reactive interaction to promote or enhance chemical reaction rate. Generally, such functional groups will have a molecular weight in the range from about 80 to 1000 daltons (D), usually being in the range from about 100 to 500 D. The active functionalities may comprise the side chains-of the twenty naturally-occurring amino acids, the side chains of synthetic amino acids which may be incorporated in the polypeptides by recombinant DNA or other synthetic techniques as described hereinbelow, or a virtually unlimited variety of other functional groups which may be attached through the amino acid side chains by conventional protein linking techniques.

The naturally-occurring amino acid side chains include the distinct functionalities which are found in most biologic systems. Preferably, the amino acid side chains will be selected from the group of non-aliphatic side chains, more preferably being selected from the basic side chains (those of lysine, arginine, and histidine), the acidic side chains (aspartate and glutamate), the aliphatic hydroxyl side chains (serine and threonine), thiol (cysteine), sulfide (methionine), phenol (tyrosine) and aminoindole (trytophan). When employing the natural amino acid side chains as the active functionalities of the present invention, it will be necessary to arrange the side chains so that they specifically interact with the reactant or reactive intermediate in a manner which enhances the reaction rate beyond that which is attributable to any transition state stabilization which occurs. Usually, when the active functionalities are the amino acid side chains, they will be part of the amino acids which define the binding site, although it is possible for the amino acids outside of the binding site to assume a catalytic or reactive activity.

In addition to the natural amino acid side chains, synthetic amino acids having non-natural side chains (or other variations, e.g., D-isomers) may be incorporated in the polypeptide structure, either by recombinant DNA techniques or by solid phase synthesis techniques, as described in more detail hereinbelow. Such synthetic amino acids may have a wide variety of side chains which are not normally found in biologically-produced proteins, providing an array of reactive and catalytic capabilities which could not be found in natural enzymes.

Synthetic amino acid side chains which may be incorporated in the polypeptides of the present invention (either by employing synthetic amino acids or by covalent attachment to natural or synthetic amino acid side chains as described below) include both catalytic functionalities, such as acids, bases, enzyme cofactors, metal complexes, electrophiles, nucleophiles, photoactive molecules, redox active molecules, and the like, and reactive funtionalities, such as alkylating agents, oxidizing agents, reducing agents, hydrolytic agents, photoactive agents, and the like. Specific functionalities include thiols, primary and secondary amines, aldehydes, carboxylates, nitriles, aromatic amines, aromatic carboxylates, primary alcohols, and the like.

Active functionalities may also be covalently attached to the side chains of amino acids proximate the binding site. The choice of such covalently-attached active functionalities is virtually unlimited, although functionalities within the binding site will usually be sufficiently small so as not to interfere with the desired binding ability of the polypeptide. Often, the active functionalities must be capable of covalent attachment to amino acid side chains by suitable chemical synthesis techniques under conditions which do not denature the polypeptide.

Suitable active functionalities which may be covalently attached to the polypeptides of the present invention by binding to amino acid side chains include naturally-occurring cofactors and derivatives thereof, such as pyridoxamine (useful in transamination, racemization, or decarboxylation reactions), flavins and nicotinamides (useful in redox reactions), porphyrins (useful in hydroxylation or epoxidation reactions), thiamine (useful in decarboxylation and addition reactions), and folates (useful in redox reactions). Synthetic active functionalities include metal complexes, such as $Zn^{+2}$-phenanthroline derivatives (useful in hydrolytic and redox reactions), $Fe^{III}$-EDTA (ethylenediaminetetraacetic acid) derivatives (useful in redox reactions including hydroxylations), $Co^{II}$ and $Co^{III}$-polyamine derivatives (useful in hydrolytic reactions), $Cu^{+2}$-bipyridyl derivatives (useful in redox reactions including hydroxylations), $Rh^{II}$-phosphine and amine derivatives (useful in hydrogenation and hydrolytic reactions) and $Zn^{+2}$ cyclam derivatives photosensitizers, such as indoles, quinones, and benzophenones (useful in photocleavage, photoaddition, photorearrangement, photoisomerization, and singlet oxygen formation); nucleophiles, such as hydroxamates, hydroxylamines; hydrazines, and peroxides (useful in hydrolytic reactions); bases, such as pyridines, tetrazoles, alkylamines (useful in elimination, hydrolytic, and isomerization reactions); electrophiles, such as nitrogen and sulfur mustards, imines, aldehydes, alkyl halides, sulfates, sulfonates, and quinones (useful in addition reactions); and the like.

The distinction between active functionalities having catalytic activity and reactive activity is as follows. Catalytically active functionalities lower the free energy of activation for a reaction thereby accelerating the rate of reaction. The catalytically active functionality itself undergoes no net chemical or structural change at the completion of the reaction. Reactive functionalities, in contrast, cause a chemical transformation in one or more of the reactants and themselves will undergo a net chemical change at the completion of the reaction.

The catalytic and reactive polypeptides of the present invention may be prepared by a number of alternate techniques. The techniques include both synthetic and recombinant preparation methods where the polypeptide is produced to have a specific amino acid sequence (with the active functionality usually being a natural or synthetic amino acid side chain) as well as post-translational modification methods where the active functionality is covalently attached to an amino acid side chain of a previously-prepared polypeptide by chemical linking reactions in some cases, however, it will be desirable to combine the two approaches by first producing a polypeptide having a preselected natural or synthetic amino acid located at a desired position and then covalently attaching an active functionality to the side chain of the preselected amino acid by suitable post-translational chemical linking methods.

A third general approach involves the preparation of antibodies having a desired binding site configuration based on the geometry and electronic configuration of the hapten used to raise the antibody. In addition to mimicing the reactant or reactive intermediate, the hapten will be chosen to elicit the desired catalytic or reactive amino acid side chain within the antibody binding site. Specifically, the hapten may be a reactant, reactant analog, reactive intermediate, reactive intermediate analog, transition state analog, or multisubstrate analog which further possess structural and electronic features which generate at least one preselected amino acid proximate the antibody combining site. The side chain of that amino acid will be the active functionality, as defined above, in the resulting antibody molecules.

Synthetic and recombinant techniques for producing the catalytic and reactive polypeptides of the present invention will usually start with an exemplary amino acid sequence which is characteristic of a protein which is known to bind a reactant or reactive intermediate with the requisite affinity. Such exemplary amino acid sequences may be derived from enzymes which are known to catalyze the chemical reaction of interest or from antibodies which have been raised against reactants or transition state and multisubstrate analogs of the reaction of interest. The preparation of such antibodies is well described in the background art described above. In addition to the desired binding affinity, the exemplary protein may also possess catalytic activity as will frequently be the case with enzymes and antibodies which have been elicited against a hapten which mimics a transition state analog. In such cases, the present invention may be utilized to enhance the catalytic or reactive capability of the modified polypeptides relative to the exemplary proteins from which they are derived.

Once the amino acid sequence of the exemplary protein is obtained, it will be possible to examine the interaction between the protein and the reactant or reaction intermediate and determine the desired modification, i.e., locate where to introduce an active functionality. Conveniently, x-ray crystallography or other suitable analytic techniques may be used to study the orientations and interactions of the reactants or reactive intermediates with the exemplary protein in order to determine what modification would be beneficial.

In the case of amino acid substitutions or additions which will be modified post-translationally with catalytic or reactive groups, the desired modification will be made so as to place the catalytic or reactive group in close proximity to the bound substrate. If possible, unfavorable steric interactions between the catalytic or reactive group and the substrate will be minimized. In addition, orbital overlap between the catalytic or reactive group and the substrate will be optimized. The modification should also be made so as to facilitate post-translational modification of the amino acid.

In the case of substitution or addition of catalytic or reactive natural or synthetic amino acid side chains, modification will be made so as to minimize unfavorable steric interactions between the polypeptide and substrate so as to optimize orbital overlap between the side chain and the substrate. In all cases, it is important that the modification does not significantly decrease the binding affinity of the polypeptide to the substrate or significantly destabilize the polypeptide itself.

Synthetic methods may be utilized for preparing polypeptides having fewer than about 200 amino acids, usually having fewer than about 150 amino acids, and more usually having 100 or fewer amino acids. The synthetic preparation methods, as described in more detail below, are particularly convenient for allowing the insertion of synthetic (non-natural) amino acids at a desired location within the polypeptide, but suffer from low yields and lack of glycosylation when compared to biological synthesis techniques.

Suitable synthetic polypeptide preparation methods may be based on the well-known Merrifield solid-phase synthesis method where amino acids are sequentially added to a growing chain (Merrifield (1963) J. Am. Chem. Soc. 85:2149-2156). Automated systems for synthesizing polypeptides by such techniques are now commercially available from suppliers such as Applied Biosystems, Inc., Foster City, Calif. 94404; New Brunswick Scientific, Edison, N.J. 08818; and Pharmacia, Inc., Biotechnology Group, Piscataway, N.J. 08854.

For the preparation of larger and/or glycosylated polypeptides, recombinant preparation techniques are usually preferred. Such recombinant techniques involve the expression in cultured cells of recombinant DNA molecules encoding the desired polypeptide amino acid sequence. The DNA sequence may itself be synthetic or alternatively be modified from a natural source, i.e., the gene of an exemplary antibody or enzyme. Synthetic DNA sequences (polynucleotides) may be synthesized by well-known techniques. For example, short-single stranded DNA fragments may be prepared by the phosphoramidite method described by Beaucage and Carruthers (1981) Tett. Letters 22:1859-1862. A double-stranded fragment may then be obtained by either synthesizing a complementary strand and annealing the strands together under appropriate conditions or by adding the complementary strand using DNA polymerase with an appropriate primer sequence. Conveniently, automated equipment for preparing the synthetic DNA sequences are available from the suppliers listed above as providing synthetic polypeptide equipment. Alternatively, the desired DNA sequence may be obtained from a suitable cDNA or genomic library obtained from a cell line expressing the exemplary protein of interest. For example, the gene expressing a monoclonal antibody of interest may be isolated from the hybridoma cell line expressing such antibody. The gene may then be modified as described in more detail hereinbelow to substitute or add the amino acids providing the active functionality (or active functionality attachment site) of interest. The techniques for isolating antibody genes from hybridoma cell lines are well described in the scientific literature. See, for example, Gearhart et al. (1983) Proc. Natl. Acad. Sci. USA 80:3439-3443.

The natural or synthetic DNA fragments coding for the desired catalytic or reactive polypeptide will be incorporated in DNA constructs capable of introduction to and expression in an in vitro cell culture. The DNA constructs may be suitable for replication in a unicellular host, such as yeast or bacteria, but will frequently be intended for introduction into and integration within the genome of cultured mammalian or other eukaryotic cell lines. DNA constructs prepared for introduction into bacteria or yeast will include a replication system recognized by the host, the DNA fragment encoding the polypeptide of interest, transcriptional and translation initiation regulatory sequences joined to the 5'-end of the DNA sequence, and transcriptional and translational termination regulatory sequences joined at the 3'-end of the DNA sequence. The transcriptional regulatory sequences will include a heterologous promoter which is recognized by the host. Conveniently, available expression vectors which include replication system and transcriptional and translational regulatory sequences together with an insertion site for the DNA sequence to be expressed may be employed.

Of particular interest to the present invention are expression systems for the Fv and F(ab) regions of an antibody molecule. Such systems are described in Bird et al. (1988) Science 242:423; Houston et al. (1988) Proc. Natl. Acad. Sci- USA 85:5879; Skerra and Pluckthun (1988) Science 240:1028; and Bette et al. (1988) Science 240:1041. Polypeptides comprising these regions retain the binding specificity of the intact antibody from which they are derived, but are substantially smaller and may be produced in a variety of expression hosts, e.g., *E. coli*, which offers advantages over the production of intact monoclonal antibodies in hybridoma cell lines.

It will frequently be desirable to produce both the $V_L$ and $V_H$ chains of the Fv region as a single fusion protein joined by an appropriate linker which allows folding. Such single chain expression systems are described in Bird et al. (1988), supra, and Houston et al. (1988), supra. Alternatively, the $V_L$ and $V_H$ chains may be expressed and subsequently reconstituted under appropriate conditions. Such separate chain expression systems are described in Skerra and Pluckthun (1988), supra, and Bette et al. (1988) supra.

When starting with isolated genes encoding the exemplary protein, usually an antibody,--enzyme, or a fragment thereof, it is necessary to modify the gene to substitute or add amino acids within or near the binding site. A variety of methods for altering the natural gene sequence to provide such substitutions or additions are known and amply described in the patent and scientific literature. See, for example, *Molecular Cloning: A Laboratory Manual* (Maniatis et al., eds.) Cold Spring Harbor Laboratory, Cold Spring Harbor, New York (1982) and *Guide to Molecular Cloning Techniques* (Berger and Kimmel, eds.) Methods in Enzymology, Vol. 152, Academic Press, Inc., Orlando, Florida (1987). Particular techniques for providing such alterations in the gene include site-directed mutagenesis as described by Kunkel et al. (1985) Nucleic Acids Res. 13:8764 and cassette mutagenesis as described by wells et al. (1985) Gene 34:315-323. The altered gene may then be expressed in cell culture as described above and the modified polypeptide obtained by conventional purification techniques.

Site-directed mutagenesis is particularly useful for modifying the primary structure of antibodies and antibody fragments, where the antibodies or fragments possess binding regions which are capable of combining with the reactant(s) or reactive intermediate(s) of interest. Suitable antibody fragments will include at least a portion of one or more of the complementarity-determining regions (CDR's) of the variable region of the intact antibody, usually including at least one intact CDR, more usually including at least two intact CDR's, and preferably including all of the CDR's present in the corresponding intact antibody (where the number will vary depending on the species of origin of the intact antibody). Particularly useful will be F(ab) fragments, Fv fragments, $V_H$ fragments, and $V_L$ fragments.

Once a desired antibody is selected as a model for preparing the polypeptide of the present invention, the antibody or antibody gene is sequenced. Suitable methods for sequencing the amino acids of the antibody itself are described in Hochman et al. (1973) Biochem. 12:1130 while suitable methods for isolating and sequencing the antibody gene from a hybridoma cell line are described in Gearhardt et al. (1983), supra. When only a fragment of the antibody is to be employed, e.g., the F(ab), Fv, $V_L$ or $V_H$ fit will be necessary to sequence only the corresponding portion of the antibody or antibody gene, although frequently the entire molecule will be sequenced.

Once determined, the amino acid or DNA sequence of the antibody can be used to devise a DNA sequence encoding the desired catalytic or reactive polypeptide. The DNA sequence will normally utilize the preferred codons for the intended expression host and will further incorporate one or more unique restriction sites to facilitate cloning and subsequent mutagenesis of the synthetic gene.

When devising the DNA sequence, it will be possible to incorporate a variety of modifications intended to impart or enhance the catalytic or reactive activity of the polypeptide which is to be produced. As discussed above, it will be possible to substitute a variety of natural amino acids having active side chains at preselected locations proximate the CDR's. Additionally, it will be possible to substitute entire CDR's or portions thereof with regions derived from other proteins, e.g., metal binding sequences from metalloproteins, active regions from enzymes, CDR's from other antibodies, peptide hormone binding sites, and the like.

Site-directed mutagenesis will also be useful for introducing natural amino acids having side chains which may be used for covalent attachment of active functionalities. Particularly useful are cysteines having thiol side chains which can be covalently attached to thiols present on the active functionality, typically by disulfide exchange or alkylation reactions.

In addition to site-directed mutagenesis, random mutagenesis techniques may be employed to modify the primary structure of the antibodies and antibody fragments of the present invention. Typically, bacterial or other cell lines producing the antibodies will be exposed to known mutagens, such as sodium bisulfite, and the mutagenized antibodies screened or selected for catalytic or reactive activity using standard techniques. See, e.g., Youderian et al. (1983) Cell 35:777 and Das (1989) Proc. Natl. Acad. Sci. USA 86:496. Antibodies displaying enhanced activity may then be selected and further tested for suitability as catalytic or reactive polypeptides according to the present invention.

In some cases, it may be desirable to introduce specific substitutions using site-directed mutagenesis as described above, where the effect of such substitution is unpredictable. In those cases, the resulting antibodies and antibody fragments will have to be screened in order to determine whether there is an observable effect on catalytic activity or reactivity. This approach may be particularly suitable for identifying regions within the antibody or antibody fragment which have an effect on the activity. Once the region is identified, further modification can be effected in order to further enhance the catalytic activity or reactivity.

An alternative method may be employed for the substitution of synthetic (non-natural) amino acids in an exemplary protein encoded by an unmodified protein gene. The gene is altered, as described above, to replace an amino acid codon at the desired location proximate the binding site with a nonsense codon differing from the gene's termination codon, conveniently, oligonucleotide-directed mutagenesis can be employed for such substitution. A suppressor TRNA, directed against the nonsense codon, is chemically or enzymatically acylated with the desired synthetic amino acid and added to an in vitro transcription/translation system programmed to express the altered DNA sequence. The synthetic amino acid will be inserted at the location of the nonsense codon. The approach, of course, would work with natural amino acids as well, but would be more cumbersome than simple alteration of the DNA sequence to encode the desired natural amino acid.

The desired unique codon must not encode a natural amino acid insertion site (natural TRNA recognition site), and a suitable codon is a TAG termination or amber codon. Any mutation in a gene that generates a termination codon (TAG, TAA, or TGA) leads to premature termination of polypeptide synthesis as a consequence of the inability of the naturally-occurring tRNA to bind and compete with the release factors. Such altered genes will, of course, have to utilize one of the two alternate termination codons. This approach is particularly advantageous in that alternate amino acid substitutions can be obtained by preparation of different synthetic amino acids at the aminoacylation stage.

Mutations in the anti-codon loop of a number of tRNA molecules leads to an amber suppressor TRNA. See, e.g., Steege and Soll, in: *Biological Regulation and Development*, Vol. I, (Goldberger, ed.) Plenum Press (1978). Amber suppressors, characterized by a 5'-CUA-3'anti-codon loop, no longer respond to codons recognized by their wild-type counterparts, but instead insert amino acids only in response to amber codons (UAG).

The desired TRNA carrying a synthetic amino acid can be generated by anti-codon loop replacement, as described by Bruce et al. (1982) Proc. Natl. Acad. Sci. USA 79:7127-7131. Alternatively, a gene encoding the TRNA carrying the synthetic amino acid may be synthesized and expressed in a suitable expression system or the suppressor tRNA can be generated by runoff transcription. The chemically or genetically constructed suppressor TRNA must then be aminoacylated with the synthetic amino acid to be incorporated into the polypeptide of the present invention. A suitable chemical acylation method which utilizes N-blocked aminoacyl pCpA dinucleotide synthesized via carbonyldiimidazole mediated coupling of N-blocked amino acids with protected pCpA-OH, is condensed with an abbreviated TRNA in the presence of T4 RNA ligase. Heckler et al. (1984) Tetrahedron 40:87-94. A suitable prokaryotic in vitro transcription/translation system is described in Pratt, in: *Transcription and Translation, A Practical Approach* (Hames and Higgens, eds.) IRL Press, Washington (1984).

The recombinant production of antibodies (immunoglobulins) and their various modifications is taught in a number of recent patent applications, including EPO 8430268.0; EPO 85102665.8; EPO 85305604.2; PCT/GB85/00392; EPO 85115311.4; PCT/US86/002269; and Japanese application 85239543, the disclosures of which are incorporated herein by reference. See also U.S. Pat. No. 4,518,584, the disclosure of which is incorporated herein by reference, which describes site-directed mutagenesis of mammalian proteins.

Post-translational modification of exemplary proteins may be obtained by a novel technique employing cleavable affinity-labeling reagents. Such reagents are obtained by joining cleavable tethers or cross-links to affinity labels, e.g., haptens specific for the protein binding site. By binding the cleavable affinity label to the protein at the binding site, and subsequently covalently attaching the free end of the tether to an amino acid side chain proximate the binding site, the binding ligand can be cleaved and removed from the protein, leaving the label including a desired active functionality in place. Useful side chains for attachment include carboxylate (aspartate and glutamate), primary amine (lysine), imidazole (histidine), phenol (tyrosine), and thiol (cysteine). Specific methods for synthesizing such affinity labels and attaching them to an antibody combining site are taught in Example 1 in the Experimental section hereinafter. Such cleavable affinity labels are particularly suitable for selectively modifying polypeptides which have not been structurally characterized.

The introduction of thiols to the binding site of a polypeptide may be accomplished using affinity labels as follows. The cleavable affinity label may be a thiol ester or a disulfide, and cleavage of the label after site-specific derivatization will incorporate a free thiol at the binding site. A thiol ester can be cleaved with hydroxylamine while a disulfide can be reduced with dithiothreitol. The disulfides are reduced under mild conditions chosen to avoid disulfides buried within the protein. Another functionality suitable for cleavable linkage is acetal, which would lead to a protein-bound aldehyde that could be derivatized by reductive amination. However, the acidic conditions required for cleavage could lead to inactivation of acid-sensitive proteins. An azobenzene crosslink could be cleaved reductively to give an aromatic amine, which could then be selectively derivatized at low pH.

The choice of the reactive functionality in the affinity-labelling reagents is governed by a number of factors. The reactive group should react slowly enough so that it will react primarily at or near the binding site of the protein after equilibrium is established. The label may react with more than one type of amino acid residue, which is advantageous for maximizing the likelihood of successful derivatization. It is disadvantageous in that it can complicate the characterization of the labeled protein. Ideally, a unique residue on the polypeptide should be modified to give a homogeneous adduct. Another important consideration is the synthesis of the labeling reagents. It should be possible to easily vary the length of the reagent in order to optimize incorporation of label into the protein. The affinity label should also be easily synthesized in radiolabeled form, for ease in quantitating label incorporation. Finally, the label should be stable to subsequent protein manipulation conditions, including the degradative methods used in protein sequence determination.

Two preferred affinity reactive labeling groups are diazoketones and aromatic azides. These groups can be transformed into reactive species in the protein binding site by photochemical irradiation and therefore have the advantage that they can be specifically activated in the binding site of a protein. Several other reactive chemical functionalities are also suitable. Diazonium groups react specifically with the phenolic side chain of tyrosine. Epoxide groups react with nucleophilic side chains including primary amines (lysine) and carboxylates (aspartate and glutamate). Aldehydes react with the primary amine side chain of lysine to form Schiff base intermediates which can be reduced with sodium cyanoborohydride. The use of tritiated $NACNB^3H_3$ leads to tritium incorporation, facilitating the characterization of the labeled protein. Finally, a-bromoketones are versatile affinity-labeling reagents. Their reactivity is sufficiently slow that they can label proteins nearly stoichiometrically in their binding sites. Moreover, they react with a number of nucleophilic side chains, including carboxylate, primary amine (lysine), imidazole (histidine), and phenol (tyrosine).

The catalytic and reactive polypeptides of the present invention are utilized to promote the chemical reactions for which they have been prepared. In general, it is necessary that the polypeptides be exposed to a reaction mixture including the chemical reactants and/or reactive intermediates in such a manner that the binding sites of the polypeptides will be exposed to the system. In the case of polypeptides which are soluble in the reaction mixture of interest, it may be possible to simply dissolve a preselected concentration of the polypeptides in the reaction mixture. In other cases, it may be necessary to immobilize the polypeptides on a solid phase, such as a solid surface, porous beads, gels, and the like, or to dissolve or suspend the polypeptides in organic solvents, reverse micelles, or biphasic solvent systems.

According to the present invention, polypeptides with catalytic or reactive groups will have a host of applications. Catalytic polypeptides having active functionalities such as metal ligand complexes, nucleophiles, acids, and bases (or a combination thereof) can act as catalysts for the selective cleavage or formation of amides in polypeptide bonds (in peptides and proteins), glycosidic bonds (in sugars) or phosphodiester bonds (in RNA and DNA). Such catalysts would be useful for synthesizing biologically active polypeptides and sugars or modifying existing biologically active polypeptides, sugars or nucleic acids so as to increase or diminish their inherent biological activity. For example, a sequence specific peptidase could be generated which would enable us to selectively degrade polypeptides.

Polypeptides having metal ligand complexes, photosensitizers, natural cofactors, and redox active molecules as active functionalities can act as catalysts for the synthesis or modification of synthetic compounds or natural products, or for modifying biologically active molecules such as polypeptides, sugars or nucleic acids so as to increase or diminish their inherent biological activity. For example, DNA could be selectively cleaved by oxidation using an antibody having EDTA $Fe^{II}$ as an active functionality.

Incorporation of reactive groups such as alkylating agents (nitrogen or sulfur mustard) into antibodies or other polypeptides could lead to a reactive polypeptide capable of irreversibly binding and alkylating a receptor on the surface of an organism.

Active functionalities may be introduced to the polypeptides of the present invention by attachment to unique or rare amino acid side chains which have been introduced to the polypeptides. For example, it is possible to introduce unique synthetic amino acid side chains by the methods discussed above. By employing linking chemistry specific for such synthetic side chains, additional active functionalities may be coupled to the polypeptide. Alternatively, the introduction of amino acids having naturally reactive side chains, such as cysteine, histidine, lysine, and tyrosine, may also serve as the basis for covalent attachment of other functionalities. In some cases, however, care must be taken to prevent attachment of the functionalities to the amino acids located elsewhere in the polypeptide. Thus, it will often be preferable to utilize relatively rare amino acids, such as cysteine, rather than common amino acids, such as lysine. Suitable chemistries for attaching the functionalities to each of these side chains are well described in the chemical and patent literature.

The following examples are offered by way of illustration, not by way of limitation.

EXPERIMENTAL

Example 1

Introduction of Active Functionality to Antibody Using Affinity Label

The following studies were carried out on the IgA MOPC315, which binds substituted 2,4-dinitrophenyl (DNP) ligands with association constants ranging from $5 \times 10^4$ to $10^6 M^{-1}$ (Haselkorn et al. (1974) Biochemistry 13:2210). Although a three-dimensional structure is not available, the antibody combining site has been characterized by spectroscopic methods (UV, fluorometry, NMR), chemical modification, and amino acid sequencing of the variable region. Moreover, earlier affinity-labeling studies with reagents of varying structures (Givol and Wilcheck (1977) Meth. Enzy. 46:479; Givol et al. (1971) Biochemistry 10:3461; and Strausbauch et al. (1971) Biochemistry 10:4342) defined a number of reactive amino acid side chains in the vicinity of the combining site.

Cleavable tethers were incorporated into affinity labels specific for the MOPC315 combining site, as shown in FIG. 1. These affinity-labeling reagents contain the DNP group linked to electrophilic aldehyde or α-bromoketone groups via cleavable disulfide or thio- phenyl linkages. Covalent attachment of the label to the antibody, followed by cleavage of the crosslink and removal of the free ligand, results in site-specific incorporation of a free thiol into the antibody combining site. The geometry of affinity-labeling reagents 1-5 varies with regard to the distance between the DNP group and electrophilic moiety since the position of a nucleophilic lysine, histidine, or tyrosine side chain is not precisely known. The syntheses of affinity labels 1-5 are outlined in FIG. 2, and are described in detail hereinbelow.

(N-2,4-Dinitrophenyl)-2-aminoethyl 2-(1,3-dioxolanyl)-ethyl disulfide 6

Affinity labels 1 and 2 were prepared as follows:

To a suspension of N,N'-bis-(2,4-dinitrophenyl)-cystamine (Chan et al. (1979) Phosphorous Sulfur 7:41) (4.84 g, 10 millimoles) in dimethylformamide (200 ml) with triethylamine (50 μl) was added 2-(2-mercaptoethyl)-1,3-dioxolane (2.45 g, 18 millimoles), and the mixture was stirred at 60° C. for 24 hours. Hydrogen peroxide (2 ml of a 30% solution) was added and the dimethylformamide was removed in vacuo.

The residual oil was dissolved in methylene chloride (100 ml). The methylene chloride layer was washed with water (3×5 ml), dried over MGSO$_4$, and concentrated in vacuo to an oil. Silica gel column chromatography with 3:2 hexanes: ethyl acetate ($R_f$ 0.31) afforded 6 (1.37 g, 3.65 millimoles, 20%) as an orange oil. IR (thin film): 3353, 2923, 1623, 1525, 1342, 1138 cm$^{-1}$; $^1$H-NMR, CDCl$_3$: w 2.08 (m,2H) 2.82 (t,2H,j =7.1 Hz), 3.00 (t,2H,J =6.6 Hz), 3.8–4.0(m,6H), 4.95 (t,1H,J =4.3 Hz), 7.00(d, 1H,J=9.5 Hz), 8.30 (d, 1H,J =9.6 Hz), 8.80 (s, 1H), 9.16 (d, 1H, J=2.6 Hz); mass spectrum (EI) 375 (M+). Anal. Calcd. for C$_{13}$H$_{17}$N$_3$O$_6$S$_2$: C, 41.60; H, 4.53; N, 11.20; S, 17.07. Found: C, 41.57; H, 4.67; N, 11.10; S, 16.99.

(N-2,4-Dinitrophenyl)-2-aminoethyl 3-oxopropyl disulfide 1

A solution of dioxolane 6 (0.50 g, 1.33 millimoles) in water (2 ml), acetonitrile (2 ml) and acetic acid (8 ml) was heated at reflux for 20 h. At this time the mixture was cooled to room temperature and added slowly to 150 ml of cold saturated aqueous NaHCO$_3$. The aqueous layer was extracted with methylene chloride (3×50 ml). The combined extracts were dried over MgSO$_4$ and concentrated in vacuo to an orange oil. Silica gel chromatography using a gradient of 30 to 40% ethyl acetate in hexanes afforded 1 (0.30 g, 0.91 millimole, 68%) as an orange semi-solid: $R_f$=0.22 in 3:2 hexanes: ethyl acetate; IR (KBr pellet) 3353, 1722, 1623, 1525, 1504, 1426, 1342, 1131 cm$^{-1}$; $^1$H-NMR (CDCl$_3$) δ2.90–3.04 (m, 6H), 3.79 (t,2H,J =6.5 Hz), 7.01 (d,1H,J =9.5 Hz), 8.31 (d,1H,J =9.5 Hz), 8.80 (m,1H), 9.15 (d,1H,J =2.6 Hz) 9.83 (s, 1H); mass spectra (EI) 331 (M+). Anal. Calcd. for C$_{11}$H$_{13}$N$_3$O$_5$S$_2$: C,39.88; H, 3.93; N, 12.69; S, 19.34. Found: C, 40.01; H, 3.91; N, 12.66; S, 19.34.

(N-2,4-Dinitrophenyl)-2-aminoethyl 3-(I,3-dioxolanyl)-propyl disulfide 7

This compound was prepared as described above for 6, starting with N,N'-bis-(2,4-dinitrophenyl)cystamine (2.42 g, 5 millimoles) and 3-(3-mercaptopropyl)-1,3-dioxolane (1.48 g, 10 millimoles), to give 7 (0.60 g, 1.54 millimoles, 15%) as an orange oil: $R_f$=0.43 in 3:2 hexanes: ethyl acetate; IR (thin film) 3360, 2923, 1623, 1592, 1528, 1426, 1335, 1131 cm$^{-1}$; $^1$H-NMR (CDCl$_3$) δ1.80–1.95 (m, 6H), 2.78 (t,2H,J=7.0 Hz), 2.99 (t, 2H,J =6.7 Hz), 3.8–4.0 (m, 6H), 4.87 (t, 1H, J =4.2 Hz), 7.01 (d, 1H, J =9.5 Hz), 8.32 (d, 1H, J =9.5 Hz), 8.79 (s, 1H), 9.16 (d, 1H, J =2.6 Hz) ; mass spectrum (EI) 389 (M), 368, 359, 294, 279, 256, 225, 210, 196. Anal. Calcd. for C14H19N3O6s2: C, 43.19; H, 4.88; N, 10.80; S, 16.45. Found: C, 43.27; H, 4.65; N, 10.79; S, 16.40.

(N-2,4-Dinitrophenyl-2-aminoethyl 4-oxobutyl disulfide 2

This compound was prepared as described above for 1, starting with dioxolane 6 (389 mg, 1.0 millimole), to give 2 (340 mg, 0.99 millimole, 99%) as an orange solid: mp 64°–65° C.; R$_f$=0.25 in 3:2 hexanes: ethyl acetate; IR (KBr pellet) 3331, 3092, 2923, 2846, 1722, 1630, 1589, 1525, 1415, 1342, 1247, 1146 cm$^{-1}$; $^1$H-NMR (CDCl$_3$) δ2.06 (t,2H, J =7.3 Hz), 2.63 (t, 2H, J =7.0 Hz), 2.75 (t, 2H, J =7.1 Hz), 3.00 (t, 2H, J =6.6 Hz), 3.81 (t, 2H,J 6.1 Hz), 7.01 (d, 1H, J =9.5 Hz), 8.31 (d, 1H, J =9.5 Hz), 8.79 (s, 1H), 9.16 (d, 1H, J =2.6 Hz), 9.80 (s, 1H); mass spectrum (EI) 345 (M). Anal. Calcd. for C12H15N3O5S2: C, 41.74; H, 4.35; N, 12.17; S, 18.55. Found: C, 41.71; H, 4.38; N, 12.11; S, 18.49.

Affinity labels 3, 4, and 5 were prepared as follows:

3-(S-DNP)-Mercaptopropanoic acid 8

To a solution of 3-mercaptopropanoic acid (1.59 g, 15 millimoles) in 70 ml of 2.0 M aqueous sodium acetate (pH 5.2) was added a solution of 2,4-dinitrofluorobenzene (3.32 g, 18.0 millimoles) in 50 ml of absolute ethanol over 15 min with stirring at room temperature under nitrogen. After 24 hours, the pale yellow solid precipitate was collected and washed with water to give 8 (3.40 g, 12.5 millimoles, 83%): mp 154.5°–157.5° C.; IR (KBr) 3630,3476 (br), 3113, 3082, 1718, 1589, 1511,1344,1055,922 cm$^{-1}$; $^1$H-NMR (acetone-d$_6$) δ2.71 (t, 2H, J =7.5 Hz), 3.40 (t, 2H, J =7.5 Hz), 3.40 (t, 2H, J =7.4 Hz), 3.40 (s, 1H), 7.87 (d, 1H, J =9.1 Hz), 8.32 (dd, 1H, J =2.5, 9.0 Hz), 8.76 (d, 1H, J =2.5 Hz); mass spectrum (FAB$^-$) 271 (M-H)$^-$, 249, 199, 183, 141, 113, 109. Anal. Calcd. for C9H8N2O6S: C, 39.71; H, 2.96; N, 10.29; S, 11.78. Found: C, 39.92; H, 2.96; N, 10.15; S, 11.64.

To a solution of 8 (0.70 g, 2.5 millimoles) in dry dioxane (10 ml) was added thionyl chloride (5 ml). The mixture was stirred under nitrogen for 12 hours. The volatiles were removed in vacuo and the yellow residue was dissolved in dry dioxane (25 ml). A solution of diazomethane (0.6 M) in diethyl ether (25 ml) was added. The mixture was stirred at 0° C. for 4 hours after which the volatiles were removed in vacuo. The residue was purified by silica gel chromatography using 9:1 methylene chloride: ethyl acetate as the eluent to give 9 (0.29 g, 0.92 millimoles, 36%) as a yellow solid: mp 117°–119° C.; R$_f$=0.52 in above eluent; IR (KBr pellet) 3458 (br), 3090, 2111, 1637, 1583, 1508, 1340, 1096 cm$^{-1}$; $^1$H-NMR (CDCl$_3$) δ2.75 (t, 2H, J =7.1 Hz), 3.35 (t, 2H, J =7.3 Hz), 5.32 (s, 1H), 7.61 (d, 1H,J 9.0 Hz), 8.48 (dd, 1H, J =2.5, 9.0 Hz), 9.07 (d, 1H, J 2.5 Hz); mass spectrum (FAB$^-$) 296(M$^-$), 199, 183, 141, 109. Anal. Calcd. for C10H8N4O5S: C, 40.54; H, 2.72; N, 18.91; S, 10.82. Found: C, 40.81, H, 2.89; N, 18.59; S, 10.79.

1-Brozo-2-oxo-4-(S-DNP)-mercaptobutane 3

To a solution of 9 (95 mg, 0.32 millimoles) in dry dioxane (5 ml) at 25° C. under nitrogen was added a saturated solution of HBr in dioxane (2 ml). The mixture was stirred for 10 minutes at which time the volatiles were removed completely in vacuo to give pure 3 (130 mg, 0.373 millimoles, 86%) as a yellow solid: mp 99°–101° C.; R$_f$=0.78 in 9:1 methylene chloride: ethyl acetate; IR (KBr) 3106, 3097, 3012, 2958, 1724, 1592, 1510, 1339, 1068, 1053 cm$^{-1}$;$^1$H- NMR (acetone-d$_6$) δ3.24 (t, 2H, J =7.0 Hz), 3.46 (t, 2H, J =7.0 Hz), 4.28 (s, 2H), 7.98 (d, 1H, J =9.0 Hz), 8.48 (dd, 1H, J =2.5, 9.0 Hz); mass spectrum (FAB$^-$) 268 (M - HBr)$^-$, 233,199,183,109. Anal. Calcd. for C10H9BrN2O5S: C, 34.40; H, 2.60; Br,22.89; N, 8.02; S, 9.18. Found C, 34.50; H, 2.60; Br, 22.70; N, 7.88; S, 9.04.

4-(S-DNP)-mercaptobutanoic acid 10

This compound was prepared as described above for 8, starting with 4-mercaptobutanoic acid (1.80 g, 15 millimoles) giving 10 (3.21 g, 11.2 millimoles, 75%) as a pale yellow solid: mp 126.5°–130° C.; IR (KBr) 3528 (br), 3117, 3090, 2948, 1709, 1587, 1518, 1341 cm$^{-1}$; $^1$H-NMR (DMSO-d$_6$) δ1.85 (m, 2H), 2.34 (t, 2H, J =7.0 Hz), 3.18 (t, 2H, J =7.5 Hz), 3.78 (s, 1H), 7.95 (d, 1H, J =9.1 Hz), 8.41 (dd, 1H, J =2.4, 9.0 Hz), 8.84 (d, 1H, J =2.4 Hz); mass spectrum (FAB$^-$) 285 (M - H)$^-$, 249,199,139. Anal. Calcd. for C10H10N2O6S: C, 41.96; H, 3.52; N, 9.79; S, 11.20. Found: C, 41.94; H, 3.50; N, 9.60; S, 10.97.

1-Diazo-2-oxo-5-(S-DNP)-mercaptopentane 11

This compound was prepared as described above for 9, starting with 10 (1.00 g, 3.49 millimoles), to give 11 (0.68 g, 2.20 millimoles, 63%) as a yellow solid: mp 84°–86° C.; R$_f$=0.52 in 9:1 methylene chloride: ethyl acetate; IR (KBr) 3106, 2939, 2866, 2104, 1626, 1589, 1513, 1343 cm$^{-1}$; $^1$H- NMR (CDCl$_3$ δ2.10 (m, 2H), 2.55 (t, 2H, J =5.7 Hz), 3.10 (t, 2H, J =7.5 Hz), 5.29 (s, 1H), 7.74 (d, 1H, J =9.0 Hz), 8.38 (dd, 1H, J =2.5, 9.0 Hz), 9.06 (d, 1H, J =2.4 Hz) ; mass spectrum (FAB$^-$) 310 (M$^-$) , 249, 199, 139, 107. Anal. Calcd. for C11H10N4O5S: C, 42.58; H, 3.25; N, 18.06; S, 10-33. Found: C, 42.79; H, 3.39; N, 17.93; S, 10.14.

1-Bromo-2-oxo-5-(S-DNP)-mercaptopentane 4

This compound was prepared as described above for 3, starting with 11 (101 mg, 0.326 millimoles) to give 4 (116 mg, 0.32 millimoles, 98%) as a yellow solid: mp 87°–90° C.; Rf =0.78 in 9:1 methylene chloride: ethyl acetate; IR (KBr) 3113, 3009, 2953, 1723, 1592, 1512, 1343 cm$^{-1}$; $^1$-H- NMR (DMSO-d$_6$) δ1.89 (m, 2H), 2.79 (t, 2H, J =7.1 Hz), 3.17 (t, 2H, J =7.4 Hz), 4.36 (s, 2H), 7.88 (d, 1H, J =9.1 Hz), 8.43 (dd, 1H, J =2.5, 9.0 Hz), 8.85 (d, 1H, J =2.6 Hz) ; Anal. Calcd. for C11H11BrN2O5S: C, 36.38; H, 3.05; Br, 2.00; N, 7.71. S, 8.83. Found: C, 36.57; H, 3.17; Br, 21,83; N, 7.49; S, 9.01.

5-(S-DNP)-mercaptopentanoic acid 12

This compound was prepared as described above for 8, starting with 4-mercaptopentanoic acid (2.00 g, 15 millimoles) giving 12 (4.20 g, 14.0 millimoles, 93%) as a pale yellow solid: mp 159°–161° C.; IR (KBr) 3117, 2948, (br), 1707, 1587, 1587, 1517, 1341 cm$^{-1}$; $^1$H- NMR (acetone-d$_6$) δ1.83 (m, 4H), 2.39 (t, 2H, J =6.8 Hz), 2.83 (s, 1H) 3.26 (t, 2H, J =7.0 Hz), 7.95 (d, 1H, J 9.0 Hz), 8.45 (dd, 1H, J =2.5, 9.0 Hz), 8.96 (d, 1H, J 2.5 Hz); mass spectrum (FAB−) 299 (M-H)−, 199,183,141,113,109. Anal. Calcd. for $C_{11}H_{12}N_2O_6S$: C, 44.00; H, 4.03; N, 9.33. S, 10.68. Found: C, 43.83; H, 3.92; N, 9.42; S, 10.59.

1-Diazo-2-oxo-6-(S-DNP)-mercaptohexane 13

This compound was prepared as described above for 9, starting with 12 (1.00 g, 3.33 millimoles), to give 13 (0.70 g, 2.15 millimoles, 65%) as a yellow solid: mp 120°–122° C.; $R_f$=0.50 in 9:1 methylene chloride: ethyl acetate; IR (KBr) 3093, 2937, 2110, 1637, 1584, 1508, 1336, 1109 cm−1; 1H-NMR (CDCl3) δ1.83 (m, 4H) , 2.39 (t, 2H, J =5.8 Hz), 3.04 (t, 2H, J 7.4 Hz), 5.25 (s, 1H), 7.53 (d, 1H, J =9.0 Hz), 8.37 (dd, 1H, J =2.5, 9.0 Hz), 9.07 (d, 1H, J =2.5 Hz) ; mass spectrum (FAB−) 324, 307, 267, 199, 183, 141, 109. Anal. Calcd. for $C_{11}H_{12}N_4O_5$ S: C, 44.44; H, 3.73; N, 17.28. S, 9.89. Found: C, 44.60; H, 3.74; N, 16.99; S, 9.65.

1-Bromo-2-oxo-6-(S-DNP)-mercaptohexane 5

This compound was prepared as described above for 3, starting with 13 (119 mg, 0.366 millimoles) to give 5 (0.127 g, 0.336 millimoles, 92%) as a yellow solid: mp 80°–83° C.; $R_f$=0.78 in 9: 1 methylene chloride: ethyl acetate; IR (KBr) 3121, 2937, 2872, 1719, 1586, 1513, 1339, 1095, 1053; 1H-NMR (acetone-d6) δ1.81 (m, 4H), 2.79 (t, 2H, J=6.6Hz), 3,24 (t, 2H, J=6.8Hz), 4.18 (s, 2H), 7.93 (d, 1H, J=9.0 Hz), 8.45 (dd, 1H, J=2.5, 9.0 Hz), 8.95 (d, 1H, J=2.5Hz); mass spectrum (FAB−) 378 (M−),307, 263, 199, 183, 141, 109. Anal. Calcd. for $C_{12}H_{13}BrN_2O_5S$: C,38.21; H,3.47; Br,21.18; N,7.43; S,8.50. Found: C,38.40; H, 3.45; Br,21.34; N,7.34; S,8.46.

Antibody Modification

Affinity Labeling

The strategy for introducing a thiol into the binding site of MOPC315 is outlined in FIG. 3. These steps were carried out with the Fab fragment, generated by treating the reduced and alkylated IgA with papain followed by affinity chromatography on DNP-coupled Sepharose 4B (Goetzl (1970) Biochemistry 9:1267). The Fab fragment (at 10 μl) was treated with either 1.5 equivalents of aldehydes 1 or 2 for one hour followed by 7.5 equivalents of NACNBH3, in 0.2 M sodium phosphate; pH 7.0, at 37° C. for 20 hours, or with 1.3 equivalents of α-bromoketones 3, 4, or 5 in 0.1 m sodium bicarbonate, pH 9.0; at 37° C. for 16 hours. In both cases, the labeled Fab was purified by chromatography on Sephadex G-50 in 0.1 M sodium phosphate, pH 7.3, and, after lyophilization, subsequent affinity chromatography on DNP-coupled Sepharose 4B (Goetzl, supra.) to remove unlabeled or non-specifically labeled Fab. The extent of derivatization was quantitated spectrophotometrically (for labels 1 and 2, $\lambda_{max}$=360 nm, ε=12,800 M−1 cm−1) and additionally, for labels 1 and 2, by incorporation of tritium from NACNB3H3 (using 12 mCi/millimole NACNB3H3). With labels 2 and 4, over 90% of the label was incorporated (85% yield after affinity chromatography) (Table 1). In both cases, less than 10% non-specific labeling occurred in the presence of 10 mM of the competitive inhibitor DNP-glycine.

TABLE 1

| | Incorporation of Affinity Labels into Fab | |
|---|---|---|
| compd | % Fab labeled (without DNP-glycine) | % Fab labeled (with DNP-glycine) |
| 1 | 22 | 5 |
| 2 | 95 | 10 |
| 3 | 0 | 0 |
| 4 | 85 | 0 |
| 5 | 15 | 0 |

Cleavage of Labels and Isolation of Stable S-Thiopyridyl Adducts

Cleavage of the Fab affinity-labeled with 2 or 4 (2.0 mg) with 50 mM dithiothreitol in 2 mM EDTA, 0.1 M sodium phosphate, pH 8.0 (2 ml) for 12 hours at 37° C. afforded the free thiol The thiol-containing Fab was collected by fast-desalting chromatography using a Pharmacia FPLC column in 0.1 M sodium phosphate, pH 7.3, directly into 1.0 ml of a 4.5 MB solution of 2,2′-dithiodipyridine (0.1 M sodium phosphate, pH 5.5, containing 15% adetonitrile). This mixture (final volume of 10 ml) was allowed to react at 20° C. for 12 hours after which excess 2,2′-dithiodipyridine was removed by exhaustive dialysis. The thiolated antibody was derivatized in greater than 90% yield (65% recovery in the case of 2) based on the absorbance of thiopyridine at 343 nm (ε=7060 M−1 cm−1) (Grassetti et al. (1967) Arch. Biochem. Biophys. 119:41) after cleavage with 10 m-M dithiothreitol, and the protein absorbance at 280 rm ($E_{0.1\%}$=1.37, MW=50,000 for Fab).

Determination of Modified Site

Fab fragments labeled with 2 or 4 were subjected to tryptic digestion and peptide mapping in order to determine the selectivity of thiol incorporation. Fab was affinity-labeled in the presence of label 2 and NACNB3H3 (12 mci/millimole) or with 3H-labeled 4 (4 mci/millimole) as described above. 3 H-labeled 4 was prepared as described for 4, starting with 3,5-3H-2,4-dinitrofluorobenzene. The labeled Fab (1.0 mg/,ml) was then denatured in 8 M urea, 0.1 p Tris-HCl, pH 8.0, reduced with 20 mM dithiothreitol (1 hour at 37° C.) and alkylated with 60 mM iodoacetamide (1 hour at 37° C.). After dialysis against 7 M urea, 20 mg Tris-HCl, pH 8.0, the heavy and light chains were separated by anion exchange chromatography on a Pharmacia Mono Q FPLC column. Separation was achieved at 1.0 ml/min in 7 M urea, 20 mM Tris-HCl, pH 8.0, with a linear gradient of 40 mg to 200 mg sodium chloride over 30 min.

In the case of Fab labeled with 2, the heavy chain was found to contain over 95% of the incorporated tritium; with Fab labeled with 4, over 95% of the tritium label was on the light chain. In each case, the radiolabeled chain was dialyzed against 2 M urea/100 mM ammonium bicarbonate, pH 8.2, and then treated with trypsin (1:25 w/w trypsin:protein) in the presence of 1 mM $CaCl_2$ at 37° C. in the dark. After 8 hours, the reactions were quenched with 104 v/v acetic acid. The radiolabeled peptides were purified by reverse phase HPLC with a 70 min. linear gradient from 0 to 50% acetonitrile in water at 1.0 mi/min; (0.1% and 0.06% (v/v) trifluoroacetic acid was added to the water and acetonitrile, respectively.) Peptides were detected by their absorbance at 214 nm, fractions were collected at 1.0 ml intervals, and aliquots were counted for radioactivity (FIG. 4). Fractions containing radioactivity were rechromatographed using a 70 min. linear gradient from 0 to 50% 2-propanol in water at 0.75 ml/min. The water and the 2-propanol contained 0.1% and 0.06% trifluoroacetic acid, respectively.

The amino acid sequences of the pure peptides were determined on an Applied Biosystems 477A Protein Sequencer. With heavy chain obtained from Fab labeled with 2, all of the detectable derivatization was on lysine 52H. With the light chain from Fab labeled with 4, all of the detectable derivatization was on tyrosine 34L. These residues are identical to those labeled by Givol and coworkers (Haimovich et al. (1972) Biochemistry 11:2389) with the reagents bromoacetyl-N$^\epsilon$-DNP-L-lysine and N-bromoacetyl-N'-DNP-ethylenediamine.

Ester Cleavage Using Thiol-Derivatized Antibody

In addition to modifying the thiolated antibody selectively with catalytic and other groups, the thiol itself can act as a nucleophile in the thiolysis of appropriate substrate. DNP-containing esters 14 and 15 (FIG. 5) were chosen as substrates for the reaction with thiolated Fab labeled with 2 or 4, respectively. The position of the cleavable linkage in affinity label 2 approximates that of the ester in the corresponding substrate 14, ensuring that the thiol is positioned appropriately in the combining site to attack the ester. Likewise, the thiol in Fab labeled with 4 should be positioned to attack ester 15. Moreover, these substrates contain fluorescent coumarin leaving groups, which can readily be detected at nanomolar concentrations.

Synthesis of Substrates (N-DNP)-3-Aminopropanoic acid 7-hydroxycoumarin ester 14

A mixture of N-DNP-3-aminopropanoic acid (1.28g, 5 millimoles) and 7-hydroxycoumarin (0.81 g, 5 millimoles) in phosphorus oxychloride (8 ml) was heated at reflux under nitrogen for 2 hours. The mixture was cooled to room temperature and added to 60 ml of cold water. The brown solid was filtered, washed with cold water and dried in vacuo. Trituration with acetone gave 14 (0.79 g, 2.0 millimoles, 40%) as a light brown solid; mp 155°-156° C., IR (KBr pellet) 3374, 3107, 2368, 1750, 1722, 1624, 1532, 1426, 1349, 1159, 1127 cm$^{-1}$; $^1$H-NMR (DMSO-d$_6$) δ3.04 (t, 2H, J=6.7Hz), 3.90 (t, 2H, J=6.5Hz), 6.48 (d, 1H, J =9.6 Hz), 7.17 (d, 1H, J=8.4Hz), 7.30 (s, 1H), 7.37 (d, 1H, J=9.7Hz), 7.78 (d, 1H, J=8.5Hz), 8.07 (d, 1H, J=9.3Hz), 8.29 (d, 1H, J=9.6Hz), 8.87 (s, 1H), 8.99 (m, 1H) ; mass spectrum (FAB+) 400 (MH+) . Anal. Calcd. for C$_{18}$H$_{13}$N$_3$O$_8$: C, 54,14; H, 3.26; N, 10.53. Found: C, 54.05; H, 3.26; N, 10.23.

2,4-Dinitrobenzoic acid, 7-hydroxycoumarin ester 15

A mixture of 2,4-dinitrobenzoic acid (1.06 g, 5.0 millimoles) and 7-hydroxycoumarin (0.81 g, 5.0 millimoles) in phosphorus oxychloride (4 ml) was heated at reflux with a calcium sulfate drying tube for 40 min. The mixture was cooled to room temperature and added to water (40 ml). The brown solid was filtered, washed with cold water and dried in vacuo to give 15 (1.32 g, 3.7 millimoles, 74%) as a red-brown solid: mp 200°-205° C.; IR (KBr) 3107, 3057, 2364, 1736, 1619, 1544, 1348, 1246, 1122 cm$^{-1}$; $^1$H-NMR (DMSO-d$_6$) δ6.53 (d, 1H, J=9.6 Hz), 7.34 (dd, 1H, J=2.2, 8.5Hz), 7.47 (d, 1H, J=2.1 Hz), 7.89 (d, 1H, J=8.5Hz), 8.12 (d, 1H, J=9.6Hz), 8.44 (d, 1H, J=8.4Hz), 8.78 (dd, 1H, J=2.2, 8.4Hz), 8.93 (d, 1H, J=2.2Hz); mass spectrum (EI) 356 (M+), 195, 162, 134, 122. Anal. Calcd. for C$_{16}$H$_8$N$_2$O$_8$: C, 53.94; H, 2.26; N, 7.86. Found: C, 52.18; H, 2.29; N, 7.51.

Ester Cleavage Assays

Cleavage of DNP coumarin esters 14 and 15 by the thiol-containing antibodies was assayed in the presence of 0.1 M NaCl, 50 mM sodium phosphate, pH 7.0, with 24 μM dithiothreitol at 10° C. The release of free coumarin was quantitated fluorometrically, exciting at 355 nm and measuring emission at 455 nm. The S-thiopyridyl Fab was first dialyzed against assay buffer, 30 min. prior to the assays, an aliquot of the thiopyridyl Fab (0.15 mg in 0.19 ml) was reduced with 3.8 mM dithiothreitol at 20° C. For each assay, reduced, thiolated Fab (15 μg in 18.8 μl) was diluted with assay buffer (2.95 ml) so that the net concentrations of thiolated Fab and of dithiothreitol were 0.1 μM and 24 μM, respectively. After equilibrating, the substrate was added (30 μl of a stock solution in acetonitrile) and the solution mixed for 10 sec. before monitoring fluorescence change. Antibody rates were corrected by subtracting the rate of cleavage in the absence of Fab.

The antibody affinity-labeled with 2 was found to accelerate the cleavage of ester 14 by a factor of 6×10$^4$ over the cleavage reaction in equimolar dithiothreitol. The reaction kinetics are consistent with the formation of a Michaelis complex (FIG. 6). The kinetic constants $k_{cat}$ and $K_m$ for the reaction are 0.87 min$^{-1}$ and 1.2 μM, respectively. The thiolysis reaction was competitively inhibited

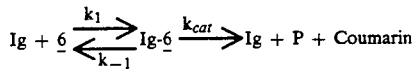

by DNP-glycine with a $K_i$ of 8 μM. Neither the uncleaved affinity-labeled antibody nor the iodoacetamide-alkylated antibody accelerated the rate of the thiolysis reaction above the background rate. The stoichiometry of product release corresponded to 1.0 coumarin to 1.0 Fab-SH. Addition of hydroxylamine to the reaction buffer did not lead to multiple turnovers. However, the introduction of both a thiol and a general base into the label may lead to a catalytic system (Bruice (1959) J. Am. Chem. Soc. 81:5444 and Street et al. (1985) J. Am. Chem. Soc. 107:7669). Interestingly, thiolated Fab labeled with bromoketone 4 did not hydrolyze DNP-acetate. Fluoroescence quenching experiments revealed that the derivatized Fab did not bind the substrate with appreciable affinity, presumably as a result of steric congestion of the antibody combining site.

Example 2

Introduction of Active Functionality by Linkage to Reactive Side Chain Previously Introduced to Antibody Using Affinity Label The following experiment describes the post-translational introduction of a catalytic group into an antibody in close proximity to the antibody combining site. The catalytic group was covalently attached to a thiol in the antibody MOPC 315 which was introduced as described in Example 1 by the use of cleavable affinity label. The thiolated antibody described in Example 1 was derivatized with an imidazole group providing a specific catalyst for ester hydrolysis.

The antibody MOPC 315 binds substituted 2,4-dinitrophenyl (DNP) ligands with association constants ranging from 533 $10^4$ to $1 \times 10^6 M^{-1}$. In order to site-specifically incorporate a derivatizable thiol into the combining site of MOPC 315, a series of cleavable affinity labels was synthesized. These labels consist of the DNP group linked to electrophilic aldehyde or bromoketone groups through cleavable disulfide or thiophenyl linkages. Covalent attachment of the label to the antibody, followed by cleavage of the crosslink and removal of free ligand, results in site-specific incorporation of a free thiol into the antibody combining site (FIG. 3). It was determined that antibody affinity labeled with an aldehyde labeling reagent in the presence of $NACNBH_3$ provides, after cleavage of the disulfide linkage, homogeneous antibody containing a free thiol at its binding site.

In order to derivatize this thiolated antibody with imidazole, the thiopyridyl disulfide adduct of the antibody (2.5 mg, 0.05 μmol) was treated with 4-mercaptomethylimidazole (Street et al. (1985) J. Am Chem. Soc. 107:7669) (0.5 μmol) in 10 mM sodium phosphate, 150 mM NaCl, pH 7.4 (PBS) at 20° C. (FIG. 8). Incorporation of imidazole (FIG. 8) was assayed by monitoring thiopyridone release spectrophotometrically at 343 nm ($\epsilon = 7060$ $M^{-1}cm^{-1}$). After 30 minutes, the reaction was complete, with quantitative release of thiopyridone. The mixture was dialyzed exhaustively against PBS and once against assay buffers. To verify imidazole incorporation, a sample of the imidazole-antibody adduct (1.0 mg) was reduced with 20 mM dithiothreitol and subjected to C18 analytical reverse phase high performance liquid chromatography. (A linear gradient was used from 0 to 20% acetonitrile in aqueous 0.1 M thiethylammonium acetate, pH 7.5 over 20 min., monitoring absorbance at 230 nm. Under these conditions, a retention time of 4.6 min. was observed for 4-mercaptomethylimidazole). A peak in the elution profile was observed with identical retention time to that for an authentic sample of 4-mercaptomethylimidazole.

The hydrolysis of coumarin esters 1a-1d (FIG. 9) by the semisynthetic antibody was assayed in the presence and absence of 1 μM derivatized Fab at varying pH, at 30° C. (Morpholineethanesulfonic acid (100 mM) as used as the buffer in the range of pH 5 to 7. Sodium phosphate (100 mill) was used in the range of pH 6 to 8 and tris-HCl (100 mill) was used in the range of pH 7 to 9.) The release of free coumarin was quantitated fluorometrically, exciting at 355 nm and measuring emission at 455 nm. Antibody rates were corrected by subtracting the rate of cleavage in the absence of antibody. From an Eadie-Hofstee plot of initial rate data, the kinetic constants, $K_m$ and $k_{cat}$, for the hydrolysis of ester 1b were determined to be 1.9% 0.2 μM and 0.051% 0.005 $min^{-1}$, respectively (pH 7.0). The hydrolysis reaction is competitively inhibited by N-DNP-glycine with a $K_i$ of 4% 1 mM (pH 7.0). This value is almost identical to the $K_D$ (5 μM) for the binding of N-DNP-glycine to underivatized MOPC 315, (determined by fluorescence quenching in PBS). The catalytic activity of the imidazole-derivatized antibody shows a pH dependence consistent with a titratable residue with pKa 7.7% 0.2, which is similar to the pKa of 4-methylimidazole, 7.5. At pH > 8, the unmodified Fab slightly accelerates the cleavage of ester 1b in a stoichiometric reaction, presumably involving modification of an amino acid side chain near the binding site. However, this reaction is not observed in the catalysis by the imidazole-derivatized antibody, where the reactive antibody side-chain is probably inaccessible. The catalytic activity of the semisynthetic antibody is destroyed by treatment with diethylpyrocarbonate, an imidazole-specific reagent. These data are consistent with the presence of a catalytic imidazole acting either as a general base or directly as a nucleophile in the hydrolysis of ester 1b. The rate of the antibody-catalyzed reaction decreased when shorter or longer esters were used as substrates (FIG. 9), presumably due to steric constraints in the binding site with the shorter substrates and higher entropic barriers with the longer esters. The second-order rate constant for the antibody-catalyzed reaction, $k_{cat}/K_m$, was compared to the rate constant for the reaction catalyzed by 4-methylimidazole at pH 7. The ratio $[k_{cat}/K_m]/k_{4-methylimidazole}$ gives an acceleration factor of 1.3% $0.1 \times 10^3$ for hydrolysis by the antibody.

SYNTHESIS OF SUBSTRATES

N-2,4-Dinitrophenyl (DNP) glycine, 7-hydroxycoumarin ester 1a

A mixture of N-DNP-glycine (603 mg, 2.5 mmol) (Sigma) and thionyl chloride (1.0 mi) in dry THF was stirred at room temperature under nitrogen for 12 h. The volatiles were removed in vacuo. Twice, dry THF (10 mi) was added and removed in vacuo to ensure complete removal of excess thionyl chloride. The residue was dissolved in dry THF (10 mi) and treated with 7-hydroxycoumarin (405 mgg, 2.5 mmol) followed by triethylamine (0.70 mL, 5.0 mmol). The mixture was stirred at room temperature for 6 h when the solvent was removed in vacuo. The residue was washed with cold water and dried in vacuo to give 1a (390 mg, 1.01 mmol, 41%) as a yellow solid: mp 220°-222° C.; IR (KBr pellet) 3349, 3100, 1729, 1624, 1525, 1398, 1349, 1237, 1117 $cm^{-1}$; $^1H$-NMR (DMSO-$d_6$) δ4.75 (d, 2H, J =4.1 Hz), 6.50 (d, 1H, J =9.6 Hz), 7.23 (d, 1H, J =8.4 Hz), 7.30 (s, 1H), 7.37 (d, 1H, J =9.7 Hz), 7.78 (d, 1H, J=8.5 Hz), 8.07 (d, 1H, J =9.3 Hz), 8.29 (d, 1H, J =9.6 Hz), 8.87 (s, 1H), 9.10 (m, 1H); mass spectrum (FAB+) 386 (MH+). Anal. Calcd. for $C_{17}H_{11}N_3O_8$: C, 52.99; H, 2.86; N, 3.64. Found C, 52.81; H, 2.92; N, 3.50.

N-DNP-3-aminopropanoic acid,7-hydroxycounarin ester 1b

A mixture of N-DNP-3-aminopropanoic acid (1.28 g, 5 mmol) and 7-hydroxycoumarin (0.81 g, 5 mmol) in phosphorous oxychloride (8 mi) was heated at reflux under nitrogen for 2 h. The mixture was cooled to room temperature and added to 60 mL of cold water. The brown solid was filtered, washed with cold water and dried in vacuo. Trituration with acetone gave 1b (0.79 g, 2.0 mmol, 40%) as a light brown solid: mp 155°-156° C., IR (KBr pellet) 3374, 3107, 2368, 1750, 1722, 1624, 1532, 1426, 1349, 1159, 1127 $cm^{-1}$; $^1H$-NMR (DMSO-$d_6$) d 3.04 (t, 2H, J=6.7 Hz), 3.90 (t, 2H, J =6.5 Hz), 6.48 (d, 1H, J =9.6 Hz)M 7.17 (d, 1H, J =8.4 Hz), 7.30 (s, 1H, 7.37 (d, 1H, J =9.7 Hz), 7.78 (d, 1H, J =8.5 Hz), 8.07 (d, 1H, J =9.3 Hz) , 8.29 (d, 1H, J =9.6 Hz) , 8.87 (s, 1H) , 8.99 (m, 1H) ; mass spectrum (FAB+) 400 (MH+). Anal. Calcd. for $C_{18}H_{13}N_8O$: c, 54.14; H, 3.26; N, 10.53. Found: C, 54.05; H, 3.26; N. 10.23.

N-DNP-aminovaleric acid, 7-hydroxycounarin ester 1c

A mixture of N-DNP-aminovaleric acid (566 mg, 2.0 mmol) (Sigma) and 7-hydroxycoumarin (324 mg, 2.0 mmol) in methylene chloride (20 mi) was cooled to 0° C. Dicyclohexylcarbodiimide (454 mg, 2.2 mmol) was added. The mixture was stirred under nitrogen at 0° C. for 2 h and at room temperature for 24 h. The dicyclohexyl urea was filtered off and the filtrate concentrated in vacuo. Trituration from 1:1 hexanes:ethyl acetate afforded 1c (384 mg, 0.90 mmol, 454) as a yellow solid: mp 124°-125° C.: IR (KBr pellet) 3340, 3107, 2831, 1729, 1624, 1525, 1504, 1419, 1349, 1258, 1159, 1124 cm$^{-1}$; $^1$H-NMR (CDCl$_3$) δ1.60 (m, 2H), 1.95 (m, 2H), 2.73 (t, 2H, i =6.7 Hz)m 3.50 (t, 2H, J =6.5 Hz), 6.41 (d, 1H, J =9.5 Hz), 6.94 (d, 1H, J =9.5 Hz), 7.04 (d, 1H, J =8.4 Hz), 7.26 (s, 1H), 7.50 (d, 1H, J =8.4 Hz), 7.70 (d, 1H, J =9.5 Hz), 8.29 (d, 1H, J =9.5 Hz), 8.59 (m, 1H)m 9.15 (s, 1H); mass spectrum (FAB+) 428 (MH+). Anal. Calcd. for C$_{20}$H$_{17}$N$_3$O$_8$: C, 56.21; H, 3.98; N, 9.84. Found: C, 55.88; H, 3.88; N, 9.50.

N-DNP-aminocaproic acid, 7-hydroxycoumarin ester 1d

This compound was prepared as described above for 1c, starting with N-DNP-aminocaproic acid (Sigma), to give 1d (36%) as a yellow solid: mp 110°-112° C.; IR (KBr pellet) 3339, 3107, 2931, 1735, 1624, 1525, 1426, 1335, 1278, 1117 cm$^{-1}$; $^1$H-NMR (CDCl$_3$) δ1.60 (m, 2H), 1.85 (m, 4H), 2.67 (t, 2H, J =7.2 Hz), 3.48 (t, 2H, J =6.4 Hz), 6.41 (d, 1H, J =9.5 Hz), 6.94 (d, 1H, J =9.5 Hz), 7.04 (d, 1H, J =8.4 Hz), 7.26 (s, 1H), 7.50 (d, 1H, J =8.4 Hz), 7.70 (d, 1H, J =9.5 Hz), 8.29 (d, 1H, i =9.5 Hz), 8.59 (m, 1H) , 9.15 (s, 1H) ; mass spectrum (FAB+) 442 (MH+). Anal. Calcd. for C$_{21}$H$_{19}$N$_3$O$_8$: C, 57.14; H, 4.31; N, 9.52. Found: C, 56.99; H, 4.40; N, 9.36.

Example 3

Hapten-dependant Preparation of Antibody Having Active Functionality in Binding Site The following example demonstrates the preparation of an antibody having a catalytic side chain in the binding site elicited by an antigen having structural features complementary to the desired side chain. In particular, antibodies are generated which catalyze the photocleavage of thymine cyclobutane dimers, the predominant DNA photolesion produced by UV light (Patrick (1977) Photochem. Photobiol. 25:357-372 and Patrick (1977) Photochem. Photobiol. 25:373-384).

Organisms have evolved a number of mechanisms for the repair of pyrimidine dimers, including the photoreactive enzyme DNA photolyase which cleaves thymidine dimers upon irradiation with visible light (Sutherland (1981) The Enzymes 14:481-515). Although the mechanism of enzymatic repair remains unclear, photosensitizers such as indoles, quinones, and flavins appear to reversibly transfer an electron to or accept an electron from the dimer, resulting in facile cleavage of the intermediate thymine dimer radical (Rokita et al. (1984) J. Am. Chem. Soc. 106:4589-4595 and Jorns (1987) J. Am. Chem. Soc. 109:3133-3136).

The intent of the following experiment was to provide a photoreacting agent by preparing an antibody combining site specific for a thymine dimer and containing an appropriately positioned photosensitizer. Antibodies were generated against the polarized π system of a pyrimidine dimer and were found to contain a complementary tryptophan residue in the combining site.

Antibodies were generated against a cis,syn-thymine dimer 2 (FIG. 10). The stereochemistry of the photocyclization reaction leading to 2 was controlled via dimerization of the N-1-carboxymethyl derivative, as the ethylene glycol diester (Leonard et al. (1969) J. Am. Chem. Soc. 91:5855-5862). Hapten 2 was synthesized by alkylation of thymine with chloroacetic acid in aqueous potassium hydroxide (Jones et al. (1973) Tetrahedron 29:2293-2296). Carboxymethylthymine was treated with one equivalent of N,N'-carbonyldiimidazole (CDI) in dimethylformamide (DMF) followed by addition of one-half equivalent of ethylene glycol. Removal of solvent and trituration with water yielded the ethylene glycol diester. The diester was dissolved in minimal DMF and photolyzed in degassed 10% aqueous acetone (1 g/750 mi) through a Pyrex filter for 2 hours using a 450 watt Hanovia medium pressure Hg immersion lamp. Removal of solvent and trituration with water afforded the thymine dimer ethylene glycol diester as a single isomer (cis,syn). Basic hydrolysis and subsequent acidification to pH 2 gave crystalline carboxymethylthymine-(cis,syn)cyclobutane dimer 1. Activation with CDI in DMF followed by addition of glycine ethyl ester yielded the bis[ethylglycinate] adduct after removal of solvent and trituration with water. Basic hydrolysis and removal of solvent gave hapten 2. N,N'-dimethylcarboxy-methylthymine(cis,syn)-cyclobutane dimer was prepared by alkaline dimethylsulfate treatment (Wulff et al. (1961) Biochem. Biophys. Acta 51:332-339) of the carboxymethylthymine ethylene glycol diester photoproduct followed by adjustment of the pH to 11 for 1 hour and subsequent acidification to pH 2 to induce crystallization.

Dimer 2 was coupled via its N-hydroxysuccinimide ester to the carrier proteins bovine serum albumin (BSA) and keyhole limpet hemocyanin (KLH) and exhaustively dialyzed against 150 MM NaCl, 10 mM phosphate buffer, pH 7.5. Epitope densities ranged between 5 and 15. Balb/c mice were immunized with the KLH conjugate of 2 and antibodies were generated by standard protocols (Jacobs et al. (1987) J. Am. Chem. Soc. 109:2174-2176). IgG was purified from ascites fluid by affinity chromatography on protein A-coupled Sepharose 4B and judged homogeneous by sodium dodecyl sulfate polyacrylamide gel electrophoresis (Laemmli (1970) Nature 227:680-685).

Solutions of carboxymethylthymine dimer 1 were irradiated with 300 nm light in the presence of antibody; and dimer cleavage was assayed spectrophotometrically as follows. Deoxygenated solutions of thymine dimer (5-300 MM) and antibody (3 AM) in 100 MM NaCl, 10 mM phosphate buffer, pH 7.5 were irradiated at 18°-20° C. in a 1 mL quartz cuvette. All photolysis experiments were performed with a 1000 W high pressure Hg-Xe lamp equipped with a Photon Technologies International, Inc. Model Q5001 Quantacount electronic actinometer and a diffraction grating monochromator blazed at 500 nm. A bandpass of 3 nm was used for both kinetic and photon counting experiments. Kinetic experiments were performed at 300 nm with an incident flux of $1.26 \times 10^{-7}$ einsteins min$^{-1}$. Monomer formation was assayed spectrophotometrically at fixed time intervals ($\lambda_{max}$=272 nm, log ε=3.90). Protein molarity was determined by absorbance at 280 nm by using $\epsilon^{0.1\%} = 1.37$ and a molecular weight of 150 kD for IgG.

Five out of six antibodies (IgG) were found to sensitize the photocleavage. one of these, antibody 15F1-3B1 was studied further. High pressure liquid chromatography confirmed that the reaction product was thymine monomer. The absorption and fluorescence spectra of the antibody remained unchanged upon photolysis, indicating that photodegradation of the protein was negligible. The kinetics of the antibody-catalyzed reaction are consistent with the Michaelis-Menten rate expression (FIG. 11):

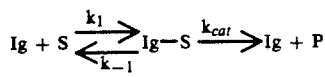

The kinetic constants $k_{cat}$ and $K_m$ are 1.2 min$^{-1}$ and 6.5 μM, respectively ($k_{cat}/K_m = 1.8 \times 10^5 M^{-1} min^{-1}$). The $k_{cat}$ value observed is comparable to the turnover number for *Escherichia coli* DNA photolyase of 3.4 min$^{-1}$ (Jorns et al. (1985) Biochemistry 24:1856-1851). The reaction is first order in light between incident intensities of $5 \times 10^{-8}$ and $1.6 \times 10^{-7}$ einsteins min$^{-1}$. Consequently, the $k_{cat}$ obtained is not optimal, and irradiation at higher flux should increase $k_{cat}$ until light saturation occurs (Eker et al. (1986) Photochem. Photobiol. 44:197-205). The first-order rate constant for unsensitized dimer cleavage is $5.5 \times 10^{-3}$ min$^{-1}$. Hapten 2 is also readily cleaved by the antibody; however the $K_m$ for this substrate is too low to be conveniently measured by direct spectrophotometric assay (<1 μl). The photocleavage of the corresponding N,N'-dimethyl substrate is not sensitized by the antibody at substrate concentrations of up to 1.8 mm, which is consistent with the high specificity of antibody-ligand binding. In addition, the dinitrophenyl specific IgA MOPC 315, which contains a binding-site tryptophan, and the phosphorylcholine specific IgA MOPC 167 do not catalyze the photocleavage of thymine dimer under identical reaction conditions (FIGS. 11(a) and 11(b).

The wavelength dependence of the quantum yield of the antibody-sensitized photolysis of hapten 2 reveals a shoulder at 300 nm (FIG. 12(a)). Antibody fluorescence is also quenched in the presence of thymine dimer (FIG. 12(b)). It should be noted that the percentage of fluorescence quenched upon ligand binding does not reflect the total number of tryptophan residues in the protein due to environmental effects on $\Phi_F$. These observations indicate that a combining site tryptophan is photosensitizing dimer cleavage.

The quantum yield of the antibody-catalyzed reaction ($\Phi_{R, 300}$) is 0.08. The antibody was oxidized with N-bromosuccinimide in 8 M urea, pH 4.5, revealing 10 tryptophan residues per Ig (Spande et al. (1967) Methods in Enzymology 11:498-506). Assuming that each binding site contains only one tryptophan allows the calculation of an approximate quantum yield of 0.4 for photocleavage of bound dimer (based on formation of monomer). Pulse radiolysis experiments have shown that dimethyl and tetramethylthymine dimer radical anions decay to monomer with a frequency of 0.05 (Lamola (1974) Mol. Photochem. 4:107-133). Since the quantum yield of the antibody-sensitized reaction is significantly higher than 0.05, the antibody appears to partition the breakdown of the intermediate radical anion.

Example 4

Hapten-dependent Preparation of Antibody Having Active Functionality in Binding Site The following example demonstrates the preparation of an antibody having a catalytic side chain in the binding site elicited by an antigen having structural features complementary to the desired side chain. In particular, antibodies are generated which catalyze the elimination of hydrogen fluoride from a β-fluoroketone.

The intent of the following experiments was to provide an antibody containing a catalytic side chain (such as a glutamate or aspartate) capable of abstracting a proton from a β-fluoroketone substrate bound in the antibody combining site. It has been demonstrated that haptens with either a positive or negative charge will elicit a complementary negatively charged or positively charged amino acid side chain, respectively, in an antibody combining site. Nisinoff et al. (1975) The Antibody Molecule, Academic Press, pp 23-27. In order to introduce a carboxylate in the combining site of an antibody to the fluoroketone substrate (FIG. 13), antibodies were generated to the corresponding hapten which contains an ammonium ion. This ammonium ion is positioned so as to elicit a carboxylate in the antibody that will be in close proximity to the abstractable proton in the fluoroketone substrate. In addition, the pKa of the carboxylate should increase when the substrate is bound (the carboxylate is no longer stabilized by a salt-bridge) thereby making it a better base for proton abstraction. Antibodies were generated against benzylamine.

Synthesis of Hapten and Substrate

N(p-nitrobenzyl)δ-aminovaleric acid 1.55 g (10 mmol) of 6-aminovaleric acid potassium salt was dissolved in 40 ml of methanol and adjusted to pH 6-7 with conc. methanolic HCl. The precipitated potassium chloride was filtered off and washed with 10 ml of methanol. To the filtrate was added 1.51 g (10 mmol) of p-nitrobenzaldehyde and 437 mg (7 mmol) of sodium cyanoborohydride. The mixture was stirred for 16 h at rt. The reaction was quenched by adding 5 ml of conc. HCl. The mixture was evaporated, redissolved in 100 ml of water and extracted with 2×50 ml of dichloromethane (extraction of unreacted or reduced aldehyde). The aqueous phase was concentrated and loaded on a DEAE-sephadex column (3×30 cm, conditioned with 0.5M triethylammonium bicarbonate pH 8.2 and subsequently washed with water). The product was eluted with a gradient of A) water and B) 0.5 M triethylammonium bicarbonate pH 8.2, B =0-50% (500 ml). The fractions were monitored by tlc (silicagel/n-BuOH:AcOH:H$_2$O)=4:1:1). The fractions containing pure product were combined and evaporated. The residue was freed from triethylammonium bicarbonate by ion exchange chromatography on Dowex 50 (H$^+$-form). After washing the adsorbed product with 100 ml water, it was eluted with 1M ammonia (100 ml). Evaporation and crystallization from water/acetone afforded 799 mg (32%) of pure product mp. 123°-125°; 1H-NMR (200 MHz,D$_2$O):8.11 (d, J =8.8/2H), 7.52 (d, J =8.8/2H), 4.19 (s/2H), 2.97 (m(t)/2H), 2.05 (t, J 7/2H), 1.57-1.45 (m/4H); 13C-NMR (50 MHz, D$_2$O+DMSO=37.9): 181.6, 175.7, 147.2, 137.2, 129.9, 123.3, 49.1, 46.4, 35.8, 24.4, 21.7; FAB+-MS: 253 (M+1)+; UV (H$_2$O) 263 nm (=10100) ; EA (C$_{12}$H$_{16}$N$_2$O$_4$) calc: C 57.13 H 6.39 N 11.10, found: C 56.93 H 6.46 N 10.99.

N-methyl-N-(p-nitrobenzyl)δ-aminovaleric acid

To a solution of 300 mg (1.19 mmol) of N-(p-nitrobenzyl)δ-aminovaleric acid in 6 ml of water were added 450 μl of a 37% aqueous formaldehyde solution (6.1 mmol) and 123 mg of sodium cyanoborohydride (1.96 mmol). This mixture was stirred for 45 min at rt. After quenching with 6 ml of 1 M hydrochloric acid the solution was directly adsorbed on a Dowex 50 ($H^+$-form) ion exchange column (2×10 cm). The column was subsequently washed with 150 ml water and the product eluted with 0.7 M ammonia. After evaporation, the remaining oil was further purified by silicagel chromatography (1×15 cm, methanol:dichloromethane=1:1). The product containing fractions (Rf =0.22) were collected and the solvent removed in vacuo. 270 mg (85% of product in form of a colorless oil was isolated. Attempts at crystallization failed. 1H-NMR (200 MHz,$D_2O$):8.10 (d,J =8.7/2H), 7.46 (d, J =8.7/2H), 3.83 (s/2H), 2.59 (m(t)/2H), 2.28 (s/3H), 2.03 (m(t)/2H), 1.49–1.39 (m/4H); 13C-NMR (50 MHz, $d^6$-DMSO): 175.3, 147.8, 146.4, 129.4, 123.3, 60.6, 56.6, 41.8, 34.1, 26.3, 22.5; FAB+-MS:267 $(M+1)^+$. EA ($C_{13}H_{18}N_2O_4 \cdot 0.H_2O$) calc. C 55.26 H 7.06 N 9.91, found: C 55.34 H 6.88 N 9.89.

BSA-conjugate of 2

A solution of 27 mg (0.1 mmol) N-methyl N-)p-nitrobenzyl)δ-aminovaleric acid in 1 ml water was adjusted to pH 2 by addition of 6 drops of 1M aqueous HCl. This solution was subsequently lyophylized and dried on HV for 72 h at rt. The residue was dissolved in 1.5 ml DMF and 62 mg (0.54 mmol) N-hydroxysuccinimide and 166 μl 1,3-dicyclohexylcarbodiimide were added. After 20 h stirring at rt, the mixture was centrifuged and the supernatant added to a solution of 30 mg BSA in 4 ml 0.75 mM aqueous sodium carbonate pH 9.3. The pH was periodically controlled and adjusted to 9.3 by addition of 0.1 M aqueous sodium hydroxide. After 20 h stirring at rt the solution was extensively dialyzed against 150 mm sodium chloride, 10 mM sodium phosphate buffer pH 7.4 (3×2 lt). All precipitated material was centrifuged. The protein concentration of the final solution was determined to be 3.41 mg/ml. The grade of derivatization with hapten was assayed by measuring selectively the remaining free lysine amino groups on an aliquot of the protein solution. Calculating with 59 lysines in BSA an epitope density of 5 was measured.

KLH-conjugate of N-methyl N-(p-nitrobenzyl)δ-aminovaleric acid

This was achieved in an analogous way as for the BSA-conjugate, using KLH as the carrier protein. The concentration of the final protein solution (Lowry) was determined to be 0.62 mg/ml with an epitope density (Habeeb assay, calculating for 34 lysines in KLH) of 18.

(R,S) 4-Hydroxy-4-p-nitrophenylbutan-2-one

To a 250 mL round-bottom flask cooled in an ice bath, 120 mL of acetone and 10 g (66.2 mmol) of p-NO2 benzaldehyde were added. Dropwise addition of 12 mL of a 1% NAOH solution effected a change in color from yellow to deep orange. Stirring was continued at 0° C. for 15 minutes followed by addition of 0.5 N HCl to pH 7.00. Volatiles were removed by rotary evaporation leaving a black oil containing water. The oil was dissolved in water and extracted several times with diethyl ether. The ether extracts were combined and dried with $MgSO_4$. The ether was removed by rotary evaporation and the orange oil was purified by flash chromatography on 300 g of silica gel, eluting with 1:1 hexanes:ethyl acetate. The fractions containing product ($R_f$=0.4) were combined and the solvent was removed by rotary evaporation to afford 10.23 g (74%) of product:mp 59°–61° C.; 1H-NMR (250 MHz, $CDCl_3$) : δ2.23 (s, 3H) ; 2.88 (d, 2H, J 6.2) ; 3.90 (d, 1H, 3.4); 5.27 (m, 1H); 7.54 (d, 2H, J 8.7); 8.16 (d, 2H, J =8.7); UV $\lambda_{max}$=275 (log $\epsilon$=5.00) mass spectrum (EI) 209 (mt) , 191 (M-$H_2O$) Anal. calcd. for $C_{10}H_{11}N_1O_4$: C, 57.44, H, 5.26, N, 6.69. Found: 57.23, 5.26, 6.79.

(R,S) 4-Fluoro-4-p-nitro phenylbutan-2-one

To a 3-neck 100 mL round-bottom flask 1.42 g (6.79 mmol) of 4-hydroxy-4-p-nitrophenyl-butan-2-one and 70 mL of freshly distilled methylene chloride were added. At −78° C. 0.90 mL (6.79 mmol) of diethylaminosulfurtrifluoride was added dropwise over 10 minutes stirring was continued for an additional 10 min. after which the reaction was quenched with aqueous 0.1 M citrate pH 5.00 buffer. The organic layer was quickly separated and dried over $MGSO_4$. The $MgSO_4$ was removed by filtration and the methylene chloride was removed by rotary evaporation affording 0.99 g (69%) of an orange oil. 'H NMR (250 MHz, $CDCl_3$): δ2.23 (s, 3H); 2.85 (m, 1H); 3.22 (m, 1H); 6.15 (m, 1H); 7.52 (d, 2H, J =8.9); 8.23 (d, 2H, J =8.3). UV $\lambda_{max}$=282 (log $\epsilon$=3.99). Mass spectrum (EI) 211 (mt), 196 (m-methyl). Anal. calcd. for $C_{10}H_{10}N_{/1}O_3F_1$: C, 56.87; H, 4.74; N, 6.61. Found: 56.74, 4.83, 6.54.

Hapten (N-methyl N-(p-nitrobenzyl)δ-aminovaleric acid) was coupled to the carrier proteins bovine serum albumin (BSA) and keyhole limpet hemocyanin (KLH) and exhaustively dialyzed against 150 mm NACL, 10 mM phosphate buffer, pH 7.5. Epitope densities ranged between 5 and 15. Balb/c mice were immunized with the KLH conjugate of N-methyl N-(p-nitrobenzyl)δ-aminovaleric acid and antibodies were generated by standard protocols (Jacobs et al. (1987) J. Am. Chem. Soc. 109:2174–2176). Ig was purified from ascites fluid by SDS polyacrylamide gel electrophoresis (Laemmli (1970) Nature 227:680–685).

Solutions of (R,S) 4-fluoro-4-p-nitrophenylbutan-2-one were incubated with 2 μM Ig at 37° C. in 10 mM Bis-tris-HCl; 100 mM NaCl pH 6.0, at substrate concentration between 50 and 500 μM. Protein molarity was determined by absorbance at 280 nm using $\epsilon^{0.1\%}$=1.37 and a molecular weight of 150 kD for IgG. Elimination was followed spectrophotometrically. Four out of the six antibodies isolated (IgG) were found to catalyze the elimination above the background rate. One of these antibodies was characterized further. Eadie-Hofstee plots of initial rate data afforded a $k_{cat}$ value of 0.188 $min^{-1}$ and Km value of 182 μM. The kinetics of the reaction are consistent with the simple Michaelis-Menten rate expression:

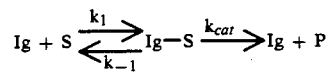

These values afford a $k_{cat}/k_{uncat}$ of 1480 at pH 6.0.

It was also demonstrated that the antibody-catalyzed reaction is competitively inhibited by hapten. Values of $K_i$ were determined at 10 mM Bis-tris-HCl 100 mM NaCl, pH 6.0 (37° C.). Substrate concentrations were 200 and 500 μM, Ig concentration was 2 μM, hapten concentration was 200 MM to 1 μM. Inhibition was demonstrated to be competitive with a $K_i$=290 nM.

The pH dependence of $k_{cat}$ was also determined under the same reaction conditions. Values of $k_{cat}$ are as follows: $k_{cat}$=0.083 min$^{-1}$ at pH 5.5, $k_{cat}$=0.11 at pH 5.75, $k_{cat}$=0.188 at pH 6.0, $k_{cat}$=0.3 at pH 6.5 and $k_{cat}$=0.43 at pH 7.5. A plot of $k_{cat}$ vs. $k_{cat}$ [H$^+$] gives a pKa of 6.1 for the active site base. It is very likely that this corresponds to a high pKa carboxylate based on the strategy for generating the antibody. Chemical modification experiments with diazoacetamide support this hypothesis.

Example 5

Modification of Antibody S107 by Site-Directed Mutagenesis

Monoclonal antibody S107, which is specific for choline phosphodiesters, is modified by site-directed mutagenesis to introduce active functionalities, including nucleophiles, chelated metals, and cofactors, as follows.

Antibody S107 has a number of features which make it useful as a catalytic antibody. First, S107 has been demonstrated to catalyze aryl choline carbonate hydrolysis by transition state stabilization. Second, the x-ray crystal structure of a homologous antibody McPC603 has been solved (Padlan et al. (1985) Ann. Instit. Pasteur Paris 136:271-290). Third, a wide variety of substances to test hydrolytic and redox reactions are easily synthesized, and fourth, the entire heavy and light chain genes have been cloned and are available on the eukaryotic expression vector pSV2-S107 (Tucker et al. (1979) Science 206:1303-1306).

Antibody S107 includes an arginine residue at position 52 in the heavy chain (Arg 52$_H$) and a tyrosine residue at position 33 in the heavy chain (Tyr33$_H$). The crystal structure of the antibody shows that both residues appear to participate in stabilizing the tetrahydral negatively-charged transition state in ester hydrolysis.

Tyrosine 33$_H$ is changed to histidine, aspartate, and glutamate to act as general bases. Arginine 52 is replaced by cysteine which could potentially participate directly in catalysis or be modified with another active group via disulfide exchange.

In order to carry out mutagenesis, pSV2-S107 was initially digested with the restriction enzyme BAM H1 in an attempt to directly isolate the 1.2 kilobasepair (kb) fragment containing the VW1 gene (FIG. 14). Due to the multiple Bam H1 sites present in the plasmid, however, the fragment could not be cleanly isolated. To circumvent this problem, the plasmid PSV2-S107 was digested with Eco R1 and Pvu 1 and the resulting 5 kb fragment was isolated via agarose gel electrophoresis. This fragment which contains the heavy chain variable region coding sequences was subcloned into the plasmid pT7-3. Restriction mapping confirmed that the desired insert was present in the pT7-S107 DNA. Plasmid pT7-S107 was digested with Bam H1 and the 1.2 kb fragment was isolated via agarose gel electrophoresis. This fragment containing the VW1 gene was now reduced to a suitable size for cloning into bacteriophage M13. Clear plaques were grown on 2YT growth medium and single stranded M13-S107 DNA was isolated by a standard bacteriophage preparation. The sequence of the VW1 gene was determined using the dideoxy chain termination sequencing method developed by Sanger. Oligonucleotide directed mutagenesis was performed using the method developed by Eckstein. Mutants were sequenced to be sure that the desired mutations had occurred. Double stranded DNA was digested with Bam H1 and the mutant 1.2 kb fragments were inserted into pT7-S107.

The final step in the cloning strategy is to isolate the mutant heavy chain gene (VW1) from the pT7-S107 plasmid and insert it into the parent vector PSV2. The resulting clones will possess mutant antibody genes which will be expressed in appropriate eukaryotic cells, and the mutant antibodies isolated. These antibodies will have the ability to catalyze the cleavage of p-nitrophenylcarbonate esters. Potential catalytic groups can be introduced via selective derivatization of the cysteine 52 mutant.

The Cys 52$_H$ mutant are further derivatized with the catalytic and chemically-reactive functionalities shown in FIG. 15. These derivatives are capable of promoting redox reactions, hydrolytic reactions, and transamination reactions.

A Cys 52 mutant derivatized with a thiol containing-pyridoxamine provides a catalytic antibody for promoting chiral transamination reactions on a keto acid choline substrate.

A Cys S107 mutant derivatized with redox active metals such as the rhodium phosphine ligand promotes hydrogenation reactions on a choline substrate. The rhodium phosphine complex is stable in aqueous buffered solutions.

Derivatizations are carried out by disulfide exchange reactions using either thiopyridyl activated antibodies or thiopyridyl activated catalytic or reactive groups. Alternatively, thiol-containing antibodies will be derivatized by selective alkylation by a catalytic or reactive group containing an electrophile such as an aldehyde or a bromoketone.

Example 6

Preparation of Hybrid Fv Fragment Based on MOPC315

A hybrid Fv fragment of the dinitrophenyl-binding immunoglobulin A, MOPC315, was produced by reconstituting recombinant $V_L$ produced in E. coli with $V_H$ derived from the antibody. A His residue was substituted for a Tyr at position 34 of $V_L$, in order to introduce a catalytic imidazole into the combining site for the hydrolysis of esters. The His mutant Fv accelerates hydrolysis of the 7-hydroxycoumarin ester of 5-(2,4-dinitrophenyl)-aminopentanoic acid 90,000-fold compared to the reaction with 4-methyl imidazole at pH 6.8. The initial rate of ester cleavage catalyzed by the mutant Fv is forty-five times faster than that of the wild type Fv. The hydrolysis of aminopropanoic and aminohexanoic homologs are not significantly accelerated. These results demonstrate that a single deliberate amino acid change can introduce significant catalytic activity into an antibody combining site and that chemical modification data can be used to locate potential sites for the introduction of catalytic residues.

The well characterized antibody MOPC315 is secreted by a mineral-oil induced reurine myeloma cell line of the same designation, and binds a variety of DNP ligands with association constants of 10$^3$-10$^7$ M$^{-1}$. MOPC315 IgA can be proteolyzed with pepsin to yield functional Fab' or Fv fragments. The Fv fragment (26 kD) is a heterodimer consisting of two peptides, $V_H$ (14 kD) and $V_L$ (12 kD), and contains all the sequences necessary for folding of the binding domain and recognition of the DNP hapten. Although the atomic coordinates for MOPC315 have not been determined, magnetic resonance spectroscopy (Dower et al., in *Biological Applications of Magnetic Resonance* (R. G. Schulman, ed., Academic Press, New York, 1979) p.271; Dwek et al. (1977) Nature 266:31; Leatherbarrow et al. (1982) Biochemistry 21:5124; and Gavish et al. (1979) Molecular Immunology 16:957) and affinity labelling (Haimovich et al. (1972) Biochemistry 11:2389) studies have provided some information concerning binding site structure.

Imidazole catalyzes the hydrolysis of carboxylate esters in aqueous solutions. The objective of this example is to substitute a His residue (having an imidazole side chain) at the appropriate position in the combining site of MOPC315 to produce a catalytic antibody with specific hydrolytic activity towards DNP-containing esters. In the absence of a crystal structure for MOPC315, data from chemical modification experiments were used to target residues for substitution with His. In spite of the fact that there are 14 potentially reactive side chains in the hypervariable region (2 His, 2 Lys, 3 Arg and 7 Tyr), DNP-containing affinity labels alkylate primarily two residues, Tyr $34_L$ and Lys $52_H$ (Pollack et al. (1988) Science 242:1038 and Haimovich et al. supra). The reactivity of each residue strongly depends on the number of atoms between the DNP ring and the electrophilic carbon of the affinity reagent; Tyr $34_L$ is alkylated most efficiently by 4, while Lys $52_H$ reacts with 5 (FIG. 16). Cleavable cross-linking agents were used to introduce a thiol (Example 1), and subsequently a catalytically active imidazole (Example 5) into the MOPC315 combining site at position $52_H$ Tyr $34_L$ was chosen for mutagenesis since it appeared that a His $34_L$ side chain would be well situated to catalyze the hydrolysis of esters 1-3 (FIG. 16) (Pollack et al. (1988) supra, and Pollack et al. (1989) J. Am. Chem. Soc. 111:1929). The role of Tyr $34_L$ in DNP binding has not been clearly established. Affinity labelling of the Tyr hydroxyl to form the 2-keto-5-thiol-pentyl ether prevents binding of ligands (Pollack et al. (1988) supra), perhaps by blocking the entrance to the site, while nitration has no effect (Leatherbarrow et al. (1982) supra, Gavish et al. (1979) supx-a) . Tyr $34_L$ is conserved in murine λ light chains and is found frequently in κ chains, and in heavy chains at the analogous position (position 33). Phenylalanine (Phe) was also substituted at position $34_L$ to assess the contribution of the Tyr hydroxyl group to hapten binding.

In order to generate mutant MOPC315 combining sites, the $V_L$ portion of the Fv domain of the antibody was expressed in *E. coli*. A hybrid Fv was then produced in which recombinant $V_L$ produced in *E. coli* was reconstituted with $V_H$ derived from MOPC315 IgA. The protein sequence of the $V_L$ peptide (residues 1-115 (Hochman et al. (1973) Biochemistry 12:1130; Hochman et al. (1977) ibid 15:2706)) was derived from a CDNA sequence of MOPC315 light chain MRNA (Kabat et al. *Sequences of Proteins of Immunological Interest*, 4th Edition (U.S. Dept. of Health and Human Services, 1987); Bothwell et al. (1982) Nature 298:380). The protein sequences was converted to a DNA sequence and restriction enzyme recognition sites were incorporated. Otherwise, the most frequently occurring *E. coli* codons were used. A gene consisting of these sequences was constructed from four restriction fragments (EcoRI-BstEII, BstEII-AvaII, AvaII-BssHII, BssHII-HindIII, denoted by the arrows above the sequence in FIG. 17). Complementary synthetic oligonucleotides 78 to 99 bases in length were phosphorylated, annealed, and ligated into a derivative of M13mpl8, either singly or as a pair. The cloned segments were sequenced and assembled into the full length gene in several steps. Cassette and primer mutagenesis (Nakamaye et al. (1986) Nucl. Acid Res. 14:9679; Kunkel (1985) Proc. Natl. Acad. Sci. USA 82:488) were used to make subsequent modifications, which resulted in the deletion of the EcoRI site.

The synthetic $V_L$ genes were expressed as a fusion with the cII gene of coliphage λ (Nagai, et al. (1984) Nature 309:810; Nagai et al. (1987) Meth. Enzymol. 153:461) as illustrated in FIG. 18. A synthetic duplex encoding the Factor Xa recognition and cleavage sequence, IleGluGlyArg, was inserted in-frame at the 5' end of the $V_L$ gene in M13. The β-globin gene in the expression vector pLcIIFXβ (nic−) (Nagai et al. supra) was excised by digestion with BamHI and HindIII and replaced by the hybrid FXVL sequence. The Tyr 34 mutations (Tyr34(TAT)→His(CAT), Phe(TTT) were made in the $V_L$ gene in M13 by the method of Kunkel (Nakamaye et al. supra) and then transferred into pLcIIFXVL by substitution of the BstEII-HindIII fragment.

The N-terminal extension of the CII-$V_L$ hybrid was removed by site-specific cleavage with Factor Xa (Fujikawa et al. (1972) Biochemistry 11:4882). The liberated $V_L$ peptide was reconstituted with antibody-derived $V_H$, and the resulting Fv was purified by gel filtration and affinity chromatography. Antibody-derived $V_H$ was prepared by denaturing ion exchange chromatography of authentic MOPC315 Fv, obtained from pepsin digestion of purified IgA and subsequent affinity chromatography. Pepsin treatment affords two major $V_H$ peptides and a small amount of incompletely digested $V_H$-containing fragments with copurify. Reconstitution experiments carried out in the absence of $V_L$ peptide afforded no DNP-binding or ester hydrolysis activity.

SDS-PAGE analysis of various stages in the production of mutant Fv proteins was performed. The results are presented in FIG. 19. Lanes 1 and 2: induced *E. coli* MZ1(pLcIIFXVL(Y34F) and (Y34H)); lanes 3 and 4: solubilized inclusion bodies; lanes 5 and 6: purified fusion proteins; lanes 7 and 8: Factor Xa cleaved and partially purified $V_L$ peptides; lanes 9 and 10: reconstituted and affinity purified Fv(Y34F$_L$) and Fv(Y34H$_L$); lane 11: Fv from proteolysis of MOPC315 IgA. The bands above $V_L$ and $V_H$ are completely digested V-containing heavy chain fragments which copurify with $V_H$.

Gel filtration analysis of Fv(Y34H L) was performed. The results are presented in FIG. 20. Inclusion bodies were obtained from induced *E. coli* MZ1 harboring pLcIIFXLV(Y34H or Y34F) (Nagai et al. supra), solubilized in 8 M urea, reduced with 20 mM dithiothreitol overnight at 4° C., and chromatographed on a 1×30 cm column of S-sepharose in 8 M urea, 20 mM NA-MES, pH 6.0, using a 0 to 200 mM NaCl gradient (yield: 10 to 30 mg of purified protein per liter of induced cells ($\epsilon_{280}$(1 mg/ml)=1.0 (Hochman et al. supra)). The purified fusion proteins were oxidized in air 30 hours, 4° C. in 2.5 M urea, 20 mM tris-Cl, pH 8.4, and then exhaustively dialyzed against 20 mM tris-Cl, pH 8.4, at 4° C. Three mg of fusion protein in 15 ml of 20 mM tris-Cl, pH 8.4, 1 mM CaCl$_2$, 30 lag/ml kanamycin sulfate, was incubated for 30 hours, 37° C. with 600 micrograms (Mg) of bovine Factor X (prepared from the BASO₄ eluate of bovine plasma (Nagai et al. (1984) supra; Nagai et al. (1987) supra; Fujikawa et al. (1972) supra)(Sigma)) activated in situ with 2.5 μg crude Russell's viper venom (Sigma). Crude $V_L$ was made 100 mM in NaCl and passed through a 2 ml bed of Q-sepharose, dialyzed against distilled water, lyophilized, and dissolved in 8 M urea, 20 mM potassium phosphate, pH 6.0. Fv(315) was purified from ascites fluid from MOPC315 myeloma grown in Balb/c mice as previously described (Eisen et al. (1968) Biochemistry 7:4126; Hochman et al. (1973) supra; Hochman et al. (1977) supra) except the gel filtration step after pepsin cleavage was omitted. $V_H$ peptide was separated from $V_L$ by ion exchange chromatography (Pharmacia mono Q 10/10 column) in 20 mM tris-Cl, pH 8.0, 8 M urea, using a 0 to 250 mm NaCl gradient. Cleaved $V_L$ (0–1 to 1 Mg) and equimolar $V_H$ were rapidly diluted ten-fold from 8 M urea into 100 mM potassium phosphate, pH 6.0 (final protein concentration =50 μg/ml) and allowed to stand 30 minutes 25° C. Active Fv was adsorbed onto DNP-lysine sepharose (Hochman et al. (1973) supra; Hochman et al. (1977) supra; Inbar et al. (1971) J. Biol. Chem. 246:6272), washed with 100 MM NaCl, 50 mM tris-Cl, pH 8.0 and eluted with a small volume of 30 mM DNP-glycine, pH 8.0. The eluate was dialyzed against 100 mM potassium phosphate, pH 6.8. Overall yield from the fusion protein is 5–20%. The yield of reconstitution is 20–30% based on $V_H$. Residual $V_L$ dimer of DNP-glycine was removed by gel filtration FPLC on a Superose 12 column in 100 mM potassium phosphate, pH 6.8. Hybrid Fv reconstituted in this fashion has the same affinity for DNP-L-lysine as Fv purified from pepsin treated MOPC315 IgA that was not reconstituted (data not shown). Because of convenience, myeloma-produced Fv(315) was used in this study. Protein purity was assessed by electrophoresis through 14% polyacrylamide SDS gels (Laemmli (1970) Nature 227:680) followed by coomassie staining and by FPLC gel filtration analysis using a Superose 12 column (flow rate of 0.5 mi/min, sample size of 100 micrograms).

The binding of ε-2,4-DNP-(L)-lysine (DNP Lys) by mutant wild type Fv proteins was assessed by titration of the intrinsic fluorescence of MOPC315 Fv (Hochman et al. (1973) supra; Hochman et al. (1977) supra), as shown in FIG. 21. Wild type Fv (Fv(315)) and the Phe mutant (Fv(Y34F$_L$) )bind DNP Lys with similar affinities at pH 6.8 ($K_D$=0.27±0.03 μM), while the His mutant (Fv(Y34H$_L$) binds this ligand 6-fold less tightly ($K_D$=1.4±0.3 μM) (FIG. 4a) (values are reported ±SE). These data suggest that the Tyr hydroxyl group is not important for recognition of the DNP moiety. DNP-aminoalkyl carboxylic acids of different lengths 6–9 (FIG. 16) were used to probe the location of the positively charged imidazole ring with respect to the DNP site in Fv(Y34H$_L$) at pH 6.0. The relative affinities of Fv(Y34H$_L$) for these ligands (7>8>9>6) is different than that of the Fv(315) (9>7>8>6). In general, Fv(Y34H L binds 6–9 two-to 8-fold less tightly than Fv(315), consistent with its lower affinity for DNP Lys at pH 6.8. In contrast to Fv(315), Fv(Y34H$_L$) binds 7 and 8 most tightly, suggesting a compensating charge interaction between the negatively-charged carboxylate of the ligand and the protonated imidazolium side chain.

The ability of wild type and mutant Fvs to hydrolyze esters 1–3 was assayed by measuring the rate of couinarin release fluorimetrically at pH 6.8 (Pollack et al. (1988) supra; Pollack (1989) supra). Fv(Y34H$_L$) efficiently hydrolyzes 1 in a manner consistent with Michaelis-Menten Kinetics ($K_m$=2.2±0.2 μM, $k_{cat}$=0.18±0.03 min$^{-1}$, $k_{cat}/K_m$=8.2×10$^4$ M$^{-1}$ min$^{-1}$, pH 6.8) (FIG. 22, Table 2). Under these conditions, Fv(Y34H$_L$) turns over at least 11 times and still retains 44% of its activity. The loss of activity is likely due to the accumulation of the inhibitory reaction product 8. The Fv-catalyzed reaction was competitively inhibited with DNP-L-lysine ($l_i$=3.8±1.5 μM). Ester 2 was a poor substrate ($k_{cat}$(2)=0. 015 min$^{-1}$); and the hydrolysis of 3 was not accelerated ($k_{cat}$ (3)<0. 005 min$^{-1}$). The fact that only the hydrolysis of 1 is significantly accelerated by Fv(Y34H$_L$) is consistent with the preference for ligands 7 and 8, and the affinity labelling data. The initial rate of hydrolysis of 1 by Fv(Y34H$_L$) at pH 6.8 is approximately 45-fold faster than the reaction with either Fv(Y34H$_L$) or Fv(315) (Table 2). At pH 8.7, the reactivity of Fv(Y34H$_L$) and Fv(315) both increase, but differentially (v(Fv(Y34H$_L$)/v(Fv(315)]=3.3, at 10 μM 1). Under these conditions FV(Y34H$_L$) catalytically hydrolyzes 1 while Fv(315) reacts stoichiometrically. The increased reactivity of Fv(315) at higher pH may be due to deprotonation of the tyrosine hydroxyl and subsequent transesterification to form a relatively stable phenol ester.

TABLE 2

| | Substrate Specificity$^{a,b}$ of Fv(Y34F$_L$) | | |
|---|---|---|---|
| | Fv(Y34H$_L$) | Fv(315) | Fv(Y34F$_L$) |
| 1 | 0.18 ± .03$^c$ | 0.004 | 0.004 |
| 2 | 0.015 | 0.005 | — |
| 3 | <0.005 | — | — |

$^a$·Expressed as $k_{cat}$.min$^{-1}$
$^b$·Assay conditions as in FIG. 4b.
$^c$SE (n = 3)

The imidazole acylating agent diethylpyrocarbonate rapidly and completely inhibits the hydrolysis of 1 at pH 6.0 (Pollack et al. (1989) supra; Holbrook (1973) Biochem. J. 131:729), supporting a catalytic role for His 34. The imidazole side chain of His 34 could catalyze the hydrolysis of ester by three mechanisms: i) nucleophilic attack on the ester carbonyl to form a labile imidazolide intermediate which is then rapidly hydrolyzed; ii) activation of an attacking water molecule; iii) electrostatic stabilization of the negatively-charged transition-state created by hydroxide ion attack on the ester carbonyl. The $V_{max}$ of Fv(Y34H$_L$) hydrolysis of 1 increases linearly by only a factor of three from pH 5.6 to 8.6. This suggests that the rate limiting step of hydrolysis does not involve simple hydroxide ion attack, since such a reaction should be first order in hydroxide ion concentration. Combined with the fact that Fv(Y34H$_L$) is more active at higher pH (where the neutral form of imidazole predominates), it seems unlikely that the observed rate acceleration is due simply to electrostatic stabilization. We presently have no evidence supporting either of the other mechanisms although imidazole derivatives hydrolyze active esters primarily by the nucleophilic pathway in aqueous solution.

In order to assess the contributions of the binding-site to hydrolysis of 1, the Fv(Y34H$_L$) catalyzed reaction was compared to the reaction with 4-methylimidazole under the assay conditions (Pollack et al. (1989) supx-a). The ratio of the biomolecular rate constants ($k_{cat}/K_m$)/$k_{4-MeIm}$ is 9±3×10$^4$. This rate acceleration is similar to that of an antibody that contains an active site carboxylate which acts as a specific base in the catalysis of an elimination reaction (Shokat (1989) Nature 338:269). The rate of hydrolysis of I by Fv(Y34H$_L$) can also be compared to that of MOPC315 Fab that has been chemically derivatized with an imidazole at Lys 52$_H$ by a flexible tether 7 atoms in length (Example 2, above). Under similar conditions, the imidazole-derivatized Fab hydrolyzes 1 approximately 16 times less rapidly than Fv(Y34H$_L$) ($k_{cat}$=0.011 min$^{-1}$, pH 7.0). The greater reactivity of Fv(Y34H$_L$) is likely due to the fewer number of degrees of freedom of the His 34 side chain allowed by the protein backbone and surrounding side chains. In addition, the His imidazole may be better aligned for attack on the ester carbonyl of 1, or for activation of a water molecule.

Although the foregoing invention has been described in some detail by way of illustration and example for purposes of clarity of understanding, it will be obvious that certain changes and modifications may be practiced within the scope of the appended claims.

What is claimed is:

1. A method for enhancing the rate of a chemical reaction involving the conversion of one or more reactants to one or more products, said method comprising exposing a reaction mixture including said one or more reactants to a modified polypeptide selected from the group consisting of antibodies and antibody fragments, said modified polypeptide having a binding site capable of forming a complex with said one or more reactants or with a reaction intermediate including said one or more reactants, wherein an active functionality is present in the modified polypeptide proximate the binding site, said active functionality being an amino acid side chain other than a naturally-occurring amino acid side chain, and said active functionality being capable of promoting the conversion of said one or more reactants to one or more products.

2. A method for enhancing the rate of a chemical reaction involving the conversion of one or more reactants to one or more products, said method comprising exposing a reaction mixture including said one or more reactants to a modified polypeptide selected from the group consisting of antibodies and antibody fragments, said modified polypeptide having a binding site capable of forming a complex with said one or more reactants or with a reaction intermediate including said one or more reactants, wherein an active functionality is present in the modified polypeptide proximate the binding site, said active functionality being covalently attached to a side chain of an amino acid proximate the binding site, and said active functionality being capable of promoting the conversion of said one or more reactants to one or more products.

3. A method for enhancing the rate of a chemical reaction involving the conversion of one or more reactants to one or more products, said method comprising exposing a reaction mixture including said one or more reactants to a modified polypeptide selected from the group consisting of antibodies and antibody fragments, said modified polypeptide having a binding site capable of forming a complex with said one or more reactants or with a reaction intermediate including said one or more reactants, wherein an active functionality is present in the modified polypeptide proximate the binding site, said active functionality being a catalytic functionality selected from the group consisting of acids, bases, enzyme cofactors, metal complexes, photoactive molecules, nucleophiles, electrophiles, and redox active molecules, and said active functionality being capable of promoting the conversion of said one or more reactants to one or more products.

4. A method for enhancing the rate of a chemical reaction involving the conversion of one or more reactants to one or more products, said method comprising exposing a reaction mixture including said one or more reactants to a modified polypeptide selected from the group consisting of antibodies and antibody fragments, said modified polypeptide having a binding site capable of forming a complex with said one or more reactants or with a reaction intermediate including said one ore more reactants, wherein an active functionality is present in the modified polypeptide proximate the binding site, said active functionality being a reactive functionality selected from the group consisting of alkylating agents, oxidizing agents, reducing agents, hydrolytic agents, photosensitizers, electrophiles, nucleophiles, acids, and bases, and said active functionality being capable of promoting the conversion of said one or more reactants to one or more products.

5. A method as in claims 1, 2, 3 or 4, wherein the antibody has been prepared against a hapten which is a reactant, a reactant analog, a transition state analog, or a multisubstrate analog.

6. A method as in claim 3, wherein the reaction is ester hydrolysis and the active functionality is an imidazole derivative.

7. A method as in claim 4, wherein the reaction is thiolysis and the active functionality is alkyl mercaptan.

* * * * *

UNITED STATES PATENT AND TRADEMARK OFFICE
CERTIFICATE OF CORRECTION

PATENT NO. : 5,302,516  
DATED : April 12, 1994  
INVENTOR(S) : Peter Schulz

Page 1 of 8

It is certified that error appears in the above-indentified patent and that said Letters Patent is hereby corrected as shown below:

column 2, line 22, please delete "Acet." and substitute therefor --Acct.--.

line 39, delete "Acet." and substitute therefor --Acct.--

Column 4, line 68, delete "2" and substitute therefor --$\underline{2}$--.

Column 5, line 23, delete "15F1-3B 1[▲]" and substitute therefor --15F1-3B1 [▲]--, line 30, delete "2" and substitute therefor --$\underline{2}$--.

line 31, delete "[▲]or" and substitute therefor --[▲] or--.

line 39, delete "1" and substitute therefor --$\underline{1}$--.

line 67, delete "(0)(400)" and substitute therefor --(0) (400)--.

Column 6, line 11, delete "(115 ra$^4$)" and substitute therefor --(115 nm)--.

line 61, delete ",however,," and substitute therefor --,however,--.

Column 7, line 35, delete "52:97≅104" and substitute therefor --52:97-104--.

Column 8, line 49, delete "chains-of" and substitute therefor --chains of--.

UNITED STATES PATENT AND TRADEMARK OFFICE
CERTIFICATE OF CORRECTION

PATENT NO. : 5,302,516

DATED : April 12, 1994

INVENTOR(S) : Peter Schulz

It is certified that error appears in the above-indentified patent and that said Letters Patent is hereby corrected as shown below:

Column 12, line 66, delete "--enzyme," and substitute therefor --enzyme,--.

Column 13, line 13, delete "wells" and substitute therefor --Wells--.

Column 14, line 36, delete "condon, conveniently," and substitute therefor --condon. Conveniently,-- line 38, delete "TRNA" and substitute therefor --tRNA--.

line 49, delete "TRNA" and substitute therefor --tRNA--.

line 62, delete "TRNA" and substitute therefor --tRNA--.

Column 15, line 1, delete "TRNA" and substitute therefor --tRNA--.

line 5, delete "TRNA" and substitute therefor --tRNA--.

line 9, delete "TRNA" and substitute therefor --tRNA--.

line 16, delete "TRNA" and substitute therefor --tRNA--.

Column 18, line 29, "($R_f$0.31)" and substitute therefor --($R_f$-0.31)--.

line 29, delete "6" and substitute therefor --$\underline{6}$--.

line 32, delete "(t,2H,j" and substitute therefor --(t,2H,J--.

line 42, delete "6" and substitute therefor --$\underline{6}$--.

UNITED STATES PATENT AND TRADEMARK OFFICE
CERTIFICATE OF CORRECTION

PATENT NO. : 5,302,516
DATED : April 12, 1994
INVENTOR(S) : Peter Schulz

Page 3 of 8

It is certified that error appears in the above-indentified patent and that said Letters Patent is hereby corrected as shown below:

line 51, delete "1 (0.30 g," and substitute therefor --$\underline{1}$ (0.30g--.

line 62, delete "3-(I,3-dioxolanyl)" and substitute therefor --3-(1,3-dioxolanyl)--.

Column 19, lines 7-8, delete "C14H19N306s2:" and substitute therefor --$C_{14}H_{19}N_3O_6S_2$:--.

line 37, delete "8" and substitute therefor --$\underline{8}$--.

line 48, delete "8" and substitute therefor --$\underline{8}$--.

Column 20, line 1, delete "1-Brozo" and substitute therefor --1-Bromo-- line 43, delete "(M-) ," and substitute therefor --($M^-$),--.

line 44, delete "10-33." and substitute therefor --10.33.--.

line 51, delete "Rf=" and substitute therefor --$R_f$=-- line 53, delete "$^1$-H-" and substitute therefor --$^1$H- --.

Column 21, line 11, delete "654" and substitute therefor --65%--.

line 15, delete "J 7.4 Hz)" and substitute therefor --J=7.4 Hz)--.

line 25, delete "5" and substitute therefor --$\underline{5}$--.

line 49, delete "NACNBH$_3$" and substitute therefor --NaCNBH$_3$--.

line 52, delete "0.1 m" and substitute therefor --0.1 $\underline{M}$--.

UNITED STATES PATENT AND TRADEMARK OFFICE
CERTIFICATE OF CORRECTION

PATENT NO. : 5,302,516                           Page 4 of 8
DATED      : April 12, 1994
INVENTOR(S): Peter Schulz It is certified that error appears in the above-indentified patent and that said Letters Patent is hereby corrected as shown below:

line 63, delete "NACNB$^3$H$_3$" and substitute therefor --NaCNB$^3$H$_3$--.

line 64, delete "NACNB$^3$H$_3$" and substitute therefor --NaCNB$^3$H$_3$--.

Column 22, line 21, delete "MB" and substitute therefor --m$\underline{M}$--.

line 28, delete "2)" and substitute therefor --$\underline{2}$--.

line 31, delete "m-M" and substitute therefore --m$\underline{M}$--.

line 32, delete "rm" and substitute therefor --nm--.

line 39, delete "NACNB$^3$H$_3$ (12 mci/millimole)" and substitute therefor --NaCNB$^3$H$_3$ (12 mCi/millimole)--.

line 42, delete "," after "mg/".

line 43, delete "0.1 p" and substitute therefor --0.1 $\underline{M}$--.

line 46, delete "20 mg" and substitute therefor --20 m$\underline{M}$--.

line 51, delete "40 mg to 200 mg" and substitute therefor --40 m$\underline{M}$ to 200 m$\underline{M}$--.

Column 23, line 9, delete "2" and substitute therefor --$\underline{2}$--.

line 25, delete "2approximates" and substitute therefor --$\underline{2}$ approximates--.

line 44, delete "14" and substitute therefor --$\underline{14}$--.

UNITED STATES PATENT AND TRADEMARK OFFICE
CERTIFICATE OF CORRECTION

PATENT NO. : 5,302,516
DATED : April 12, 1994
INVENTOR(S) : Peter Schulz

Page 5 of 8

It is certified that error appears in the above-indentified patent and that said Letters Patent is hereby corrected as shown below:

Column 25, line 5, delete "533 $10^4$" and substitute therefor --$5 \times 10^4$--.

line 17, delete "NACNBH$_3$" and substitute therefor --NaCNBH$_3$--.

Column 26, line 27, delete "1.0 mi" and substitute therefor --1.0 mL--.

line 30, delete "10 mi" and substitute therefor --10 mL--.

line 32, delete "10 mi" and substitute therefor --10 mL--.

line 54, delete "8 mi" and substitute therefor --8 mL--.

line 63, delete "M 7.17" and substitute therefor --m 7.17--.

line 67, delete "$C_{18}H_{13}N_8O$" and substitute therefor --$C_{18}H_{13}N_3O_8$--.

Column 27, line 1, delete "7-hydroxycounarin" and substitute therefor --7-hydroxycoumarin--.

line 5, delete "20 mi" and substitute therefor --20 mL--.

line 11, delete "454" and substitute therefor --45%--.

line 15, delete "2H,i=6.7 Hz" and substitute therefor --2H,j=6.7 Hz--.

line 34, delete "i=9.5" and substitute therefor --J=9.5--.

Column 28, line 18, delete "750 mi" and substitute therefor --750 mL--.

line 41, delete "150 MM" and substitute therefor --150 mM--.

UNITED STATES PATENT AND TRADEMARK OFFICE
CERTIFICATE OF CORRECTION

PATENT NO. : 5,302,516
DATED : April 12, 1994
INVENTOR(S) : Peter Schulz

Page 6 of 8

It is certified that error appears in the above-indentified patent and that said Letters Patent is hereby corrected as shown below:

line 55, delete "5-300 MM" and "100 MM" and substitute therefor --5-300 $\mu$M-- and --100 mM--.

Column 29, line 33, delete "1$\mu$l" and substitute therefor --1$\mu$M--.

line 36, delete "1.8 mm" and substitute therefor --1.8 mM--.

Column 30, line 66, delete "(M + 1)+" and substitute therefor ----(M + 1)$^+$--.

Column 31, line 23, delete "FAB+" and substitute therefor --FAB$^+$--.

line 28, delete "N-)p-" and substitute therefor --N-(p- --.

line 41, delete "150 mm" and substitute therefor --150 mM--.

line 61, delete "p-NO2" and substitute therefor --p-NO$_2$--.

Column 32, line 32, delete "$C_{10}H_{10}N_{f1}O_3F_1$" and substitute therefor --$C_{10}H_{10}N_1O_3F_1$--.

line 37, delete "150 mm" and substitute therefor --150 mM--.

line 48, delete "HCI" and substitute therefor --HCl--.

Column 33, line 3, delete "200 MM" and substitute therefor --200 mM--.

line 49, delete "VW1" and substitute therefor --VDJ1--.

UNITED STATES PATENT AND TRADEMARK OFFICE
CERTIFICATE OF CORRECTION

PATENT NO. : 5,302,516
DATED : April 12, 1994
INVENTOR(S) : Peter Schulz

It is certified that error appears in the above-indentified patent and that said Letters Patent is hereby corrected as shown below:

line 61, delete "VW1" and substitute therefor --VDJ1--.

line 65, delete "VW1" and substitute therefor --VDJ1--.

Column 34, line 7, delete "VW1" and substitute therefor --VDJ1--.

line 62, delete "reurine" and substitute therefore --murine--.

Column 36,      line 26, delete "CII" and substitute therefor --cII--.

line 52, delete "Fv(Y34HL)" and substitute therefor --Fv($Y34H_L$)-- line 58, delete "NA-MES" and substitute therefor --Na-MES--.

line 66, delete "30 lag" and substitute therefor --30 $\mu$g--.

line 68, delete "(Mg)" and substitute therefor --($\mu$g)--.

Column 37, line 1, delete "BASO$_4$ eluate" and substitute therefor --BaSO$_4$ eluate--.

line 16, delete "250 mm" and substitute therefor --250 mM--.

line 17, delete "0-1 to 1 Mg" and substitute therefor --0.1 to 1 mg--.

line 23, delete "100 MM" and substitute therefor --100 mM--.

line 59, delete "Fv(Y34H L" and substitute therefor --Fv($Y34H_L$)--.

UNITED STATES PATENT AND TRADEMARK OFFICE
CERTIFICATE OF CORRECTION

PATENT NO. : 5,302,516
DATED : April 12, 1994
INVENTOR(S) : Peter Schulz

It is certified that error appears in the above-indentified patent and that said Letters Patent is hereby corrected as shown below:

Column 38, line 9, delete "($i$=3.8" and substitute therefor --($K_i$=3,8--.
line 19, delete "(v(Fv(Y34H$_L$]/v(Fv(315)]" and substitute therefor --v[Fv(Y34H$_L$]/v[Fv(315)]--.
line 63, delete "supx-a" and substitute therefor --supra--.

Column 39, line 1, delete "I" and substitute therefor --1--.

Column 40, line 30, delete "ore" and substitute therefor --or--.

Signed and Sealed this

Twenty-ninth Day of November, 1994

Attest:

BRUCE LEHMAN

Attesting Officer

Commissioner of Patents and Trademarks